US010314652B2

(12) United States Patent
Brannan

(10) Patent No.: US 10,314,652 B2
(45) Date of Patent: Jun. 11, 2019

(54) FLEXIBLE MICROWAVE CATHETERS FOR NATURAL OR ARTIFICIAL LUMENS

(71) Applicant: COVIDIEN LP, Mansfield, MA (US)

(72) Inventor: Joseph D. Brannan, Lyons, CO (US)

(73) Assignee: Covidien LP, Mansfield, MA (US)

( * ) Notice: Subject to any disclaimer, the term of this patent is extended or adjusted under 35 U.S.C. 154(b) by 350 days.

(21) Appl. No.: 15/161,382

(22) Filed: May 23, 2016

(65) Prior Publication Data

US 2016/0278859 A1    Sep. 29, 2016

Related U.S. Application Data

(63) Continuation of application No. 14/110,652, filed as application No. PCT/US2012/032818 on Apr. 9, 2012, now Pat. No. 9,358,066.

(Continued)

(51) Int. Cl.
*A61B 18/18* (2006.01)
*A61N 5/02* (2006.01)
(Continued)

(52) U.S. Cl.
CPC .... *A61B 18/1815* (2013.01); *A61B 17/00234* (2013.01); *A61B 18/1492* (2013.01);
(Continued)

(58) Field of Classification Search
CPC .......... A61B 2018/00023; A61B 2018/00077; A61B 2018/1846; A61B 2018/1861;
(Continued)

(56) References Cited

U.S. PATENT DOCUMENTS 4,154,246 A    5/1979    LeVeen
4,583,556 A    4/1986    Hines et al.
(Continued)

FOREIGN PATENT DOCUMENTS

CN    1819802 A    8/2006
CN    1943523 A    4/2007
(Continued)

OTHER PUBLICATIONS

Australian Examination Report No. 1 from Appl. No. AU2015243789 dated Aug. 16, 2016.
(Continued)

*Primary Examiner* — Michael F Peffley
(74) *Attorney, Agent, or Firm* — Carter, DeLuca & Farrell LLP

(57) ABSTRACT

A microwave delivery device, including a coaxial feedline having an inner conductor, an inner dielectric insulator coaxially disposed about the inner conductor, and an outer conductor coaxially disposed about the inner dielectric, and a radiating portion operably coupled to a distal end. The radiating portion includes a radiating portion inner conductor operable coupled to and extending from a distal end of the coaxial feedline inner conductor, a shielding outer conductor helically wrapped about the radiating portion inner conductor and operably coupled to the coaxial feedline outer conductor; and a shielding dielectric positioned between the radiating portion inner conductor and the shielding outer conductor wherein the width of the shielding outer conductor varies according to the longitudinal position thereof along the coaxial feedline inner conductor, and a cap operably coupled to a distal end of the radiating portion inner conductor and the shielding outer conductor to provide an electrical connection therebetween.

13 Claims, 45 Drawing Sheets

Related U.S. Application Data

(60) Provisional application No. 61/473,564, filed on Apr. 8, 2011.

(51) Int. Cl.
    *A61B 17/00*     (2006.01)
    *A61B 18/14*     (2006.01)
    *A61B 18/00*     (2006.01)
    *A61B 90/10*     (2016.01)

(52) U.S. Cl.
CPC .............. *A61B 18/18* (2013.01); *A61N 5/022* (2013.01); *A61B 90/10* (2016.02); *A61B 2017/00323* (2013.01); *A61B 2018/0022* (2013.01); *A61B 2018/00023* (2013.01); *A61B 2018/00077* (2013.01); *A61B 2018/00172* (2013.01); *A61B 2018/00226* (2013.01); *A61B 2018/00232* (2013.01); *A61B 2018/00267* (2013.01); *A61B 2018/00273* (2013.01); *A61B 2018/00285* (2013.01); *A61B 2018/00345* (2013.01); *A61B 2018/00434* (2013.01); *A61B 2018/00511* (2013.01); *A61B 2018/00577* (2013.01); *A61B 2018/00791* (2013.01); *A61B 2018/00875* (2013.01); *A61B 2018/1846* (2013.01); *A61B 2018/1861* (2013.01); *A61B 2018/1884* (2013.01); *A61B 2018/1892* (2013.01)

(58) Field of Classification Search
CPC .... A61B 2018/1884; A61B 2018/1892; A61B 2018/00577; A61B 2018/00285; A61B 2018/00511; A61B 2018/00345; A61B 18/18; A61B 18/1815; A61B 18/1492
See application file for complete search history.

(56) References Cited

U.S. PATENT DOCUMENTS

| | | | |
|---|---|---|---|
| 4,841,988 A * | 6/1989 | Fetter .................. | A61B 18/18 219/712 |
| 5,026,959 A | 6/1991 | Ito et al. | |
| 5,057,106 A | 10/1991 | Kasevich et al. | |
| 5,129,396 A | 7/1992 | Rosen et al. | |
| 5,370,644 A | 12/1994 | Langberg | |
| 5,397,320 A | 3/1995 | Essig et al. | |
| 6,139,527 A | 10/2000 | Laufer et al. | |
| 6,161,049 A | 12/2000 | Rudie et al. | |
| 6,210,367 B1 | 4/2001 | Carr | |
| 6,283,987 B1 | 9/2001 | Laird et al. | |
| 6,325,796 B1 * | 12/2001 | Berube ................. | A61B 18/18 606/33 |
| 6,582,426 B2 * | 6/2003 | Moorman ......... | A61B 10/0233 600/562 |
| 6,663,625 B1 | 12/2003 | Ormsby et al. | |
| 7,797,056 B2 | 9/2010 | Forde et al. | |
| 7,998,139 B2 | 8/2011 | Rossetto et al. | |
| 8,617,153 B2 | 12/2013 | Lee et al. | |
| 9,358,066 B2 | 6/2016 | Brannan | |
| 2002/0091427 A1 | 7/2002 | Rappaport et al. | |
| 2002/0111613 A1 | 8/2002 | Berube | |
| 2003/0073988 A1 | 4/2003 | Berube et al. | |
| 2004/0133254 A1 | 7/2004 | Sterzer et al. | |
| 2005/0215942 A1 | 9/2005 | Abrahamson et al. | |
| 2007/0027385 A1 | 2/2007 | Brister et al. | |
| 2007/0129717 A1 | 6/2007 | Brown | |
| 2007/0185554 A1 | 8/2007 | Appling et al. | |
| 2007/0219544 A1 | 9/2007 | Gowda et al. | |
| 2008/0161890 A1 | 7/2008 | Lafontaine | |
| 2008/0266203 A1 | 10/2008 | Rossetto et al. | |
| 2009/0187180 A1 * | 7/2009 | Brannan .............. | A61B 18/18 606/33 |
| 2009/0222002 A1 | 9/2009 | Bonn et al. | |
| 2009/0299360 A1 | 12/2009 | Ormsby | |
| 2010/0137857 A1 | 6/2010 | Shroff et al. | |
| 2010/0217251 A1 | 8/2010 | Rossetto et al. | |
| 2010/0217361 A1 | 8/2010 | Kulstad et al. | |
| 2010/0268219 A1 | 10/2010 | Ormsby | |
| 2011/0077634 A1 | 3/2011 | Brannan | |

FOREIGN PATENT DOCUMENTS

| | | |
|---|---|---|
| EP | 0245790 A1 | 11/1987 |
| EP | 0648515 A1 | 4/1995 |
| EP | 2060239 A1 | 5/2009 |
| EP | 2147651 A1 | 1/2010 |
| EP | 2322113 A1 | 5/2011 |
| JP | 58-54853 | 4/1983 |
| JP | S59135070 A | 8/1984 |
| JP | H01221177 A | 9/1989 |
| JP | H02134170 A | 5/1990 |
| JP | H09506808 A | 7/1997 |
| JP | H09313619 A | 12/1997 |
| JP | 2002035004 A | 2/2002 |
| JP | 2002532132 A | 10/2002 |
| JP | 2004500957 A | 1/2004 |
| JP | 2005058750 A | 3/2005 |
| JP | 2006520622 A | 9/2006 |
| JP | 2007516795 A | 6/2007 |
| JP | 2007520245 A | 7/2007 |
| JP | 2008272472 A | 11/2008 |
| JP | 2009537271 A | 10/2009 |
| JP | 2009539565 A | 11/2009 |
| JP | 2010110579 A | 5/2010 |
| JP | 2011036674 A | 2/2011 |
| JP | 5763263 B2 | 8/2015 |
| WO | 9416632 A1 | 8/1994 |
| WO | 0047283 A2 | 8/2000 |
| WO | 01/87169 A1 | 11/2001 |
| WO | 0245790 A2 | 6/2002 |
| WO | 2004004586 A1 | 1/2004 |
| WO | 2004087249 A2 | 10/2004 |
| WO | 2011063061 A2 | 5/2011 |

OTHER PUBLICATIONS

Australian Examination Report No. 2 from Appl. No. AU2015202149 dated Aug. 17, 2016.
Chinese Office Action from Appl. No. CN201510184518.X dated Aug. 22, 2016.
European Examination Report from Appl. No. EP 15 195 087.0 dated Nov. 7, 2016.
European Examination Report from Appl. No. EP 12 865 090.0 dated Nov. 25, 2016.
EP Examination Report issued in Appl. No. EP 15195087.0 dated Jul. 14, 2017.
Canadian Office Action from Application No. 2,832,595 dated Mar. 27, 2015.
Canadian Office Action from Application No. 2,832,586 dated Mar. 30, 2015.
Canadian Office Action from Application No. 2,832,593 dated Mar. 27, 2015.
Australian Examination Report dated May 17, 2015 from Appl. No. AU 2012364792.
Australian Examination Report dated Aug. 4, 2014, Application No. 2012239878.
Supplementary European Search Report dated May 20, 2014, Application No. 12768651.
Chinese Office Action and English translation dated Aug. 26, 2014, Application No. 201280025173.8.
Supplementary European Search Report dated Jan. 8, 2015, Application No. 12865169.
Japanese Office Action dated Mar. 5, 2014, Application No. 2014-504084.
Supplementary European Search Report dated Nov. 19, 2014, Application No. 12865090.
Japanese Laid-Open Publication No. 2002-35004 with English Abstract.

(56) References Cited

OTHER PUBLICATIONS

Japanese Laid-Open Publication No. 2004-187703 with English Abstract.
Japanese Office Action, Application No. JP 2014-504085 dated Jan. 13, 2015.
International Search Report dated Aug. 20, 2013 in PCT/US2012/032820.
International Search Report dated Aug. 20, 2013 in PCT/US2012/032821.
International Search Report dated Oct. 23, 2012 in PCT/US2012/032818.
Chinese Office Action dated Jul. 9, 2015 from Appl. No. CN 201280024841.5.
European Search Report, Application No. EP 12 76 8651 dated May 20, 2014.
Australian Examination Report Application No. 2012364794 dated Jan. 22, 2015.
Canadian Office Action from Appl. No. 2,845,795 dated Nov. 30, 2015.
Extended European Search Report from European Appl. No. EP 15195087.0 dated Mar. 4, 2016.
Canadian Office Action issued in Appl. No. CA 2,832,595 dated Mar. 21, 2016.
Japanese Office Action and English language translation from Application No. JP 2015-117544 dated Apr. 26, 2016.
Japanese Office Action, and English language translation, issued in Appl. No. JP 2017-002436 dated Nov. 7 2017 (6 pages).
First Office Action and English language translation issued in Chinese Appl. No. 201610052796.4 dated Jun. 8, 2017.
Decision of Rejection issued in Japanese Appl. No. JP 2017-002436 dated Feb. 20, 2018, together with English translation (5 pages).
European Examination Report issued in Appl. No. EP 15195087.0 dated Mar. 6, 2018 (4 pages).
Extended European Search Report from Appl. No. EP 16171295.5 dated Feb. 7, 2017.
Japanese Office Action issued in corresponding Appl. No. JP 2018-115304 dated Apr. 23, 2019, together with English language translation (5 pages).

\* cited by examiner

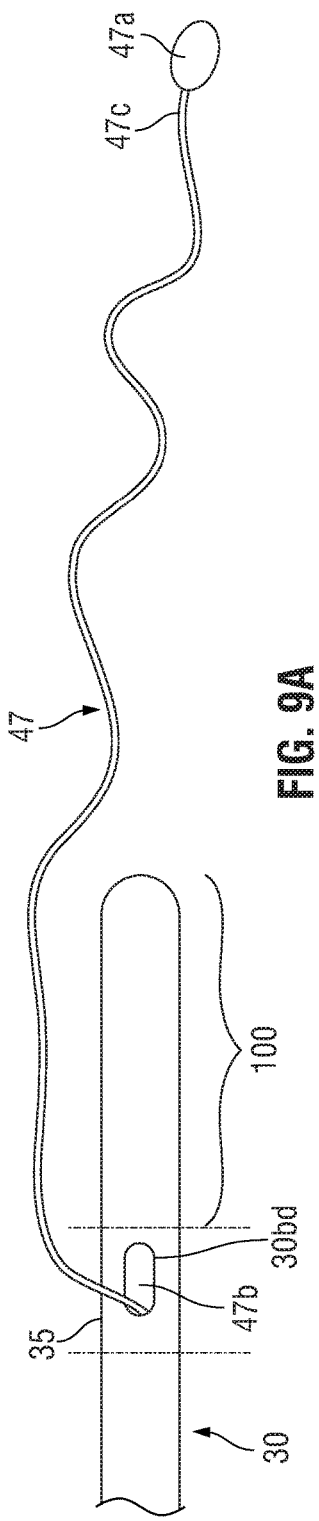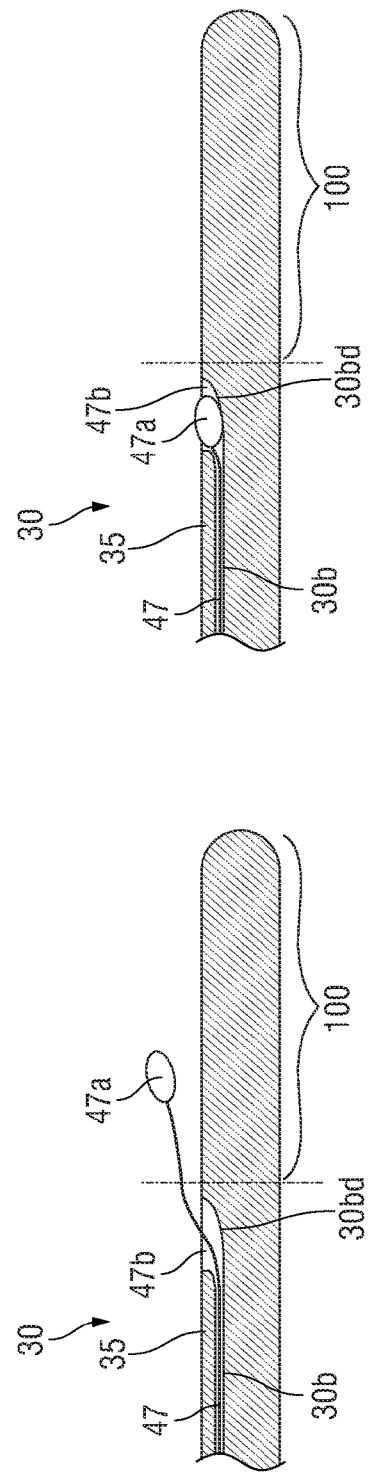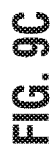
FIG. 9A
FIG. 9B
FIG. 9C

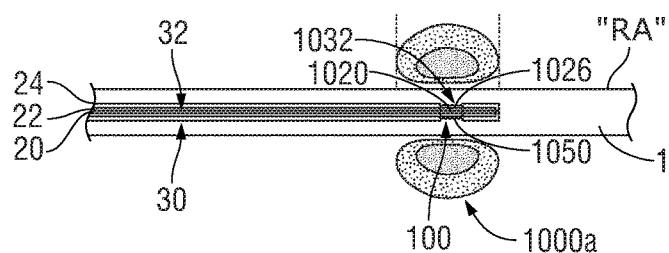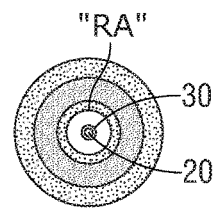
FIG. 10A  FIG. 10B
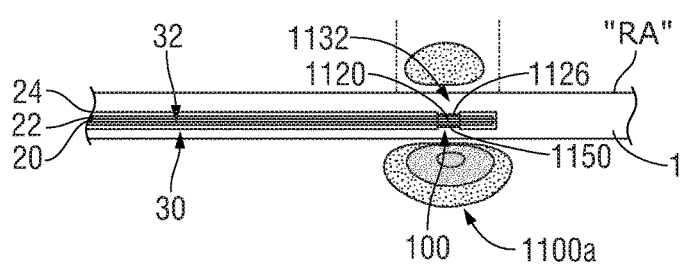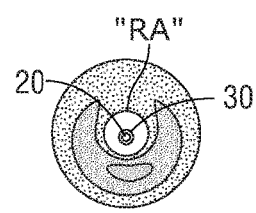
FIG. 11A  FIG. 11B
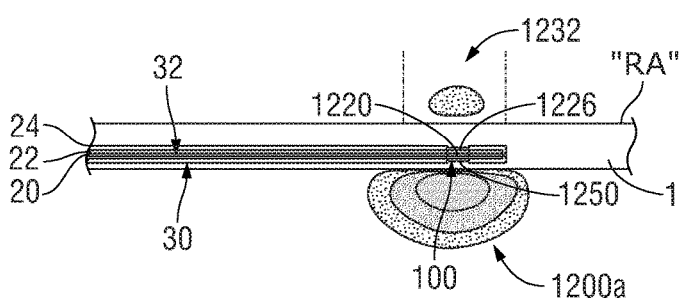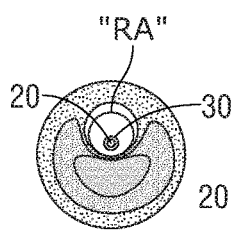
FIG. 12A  FIG. 12B

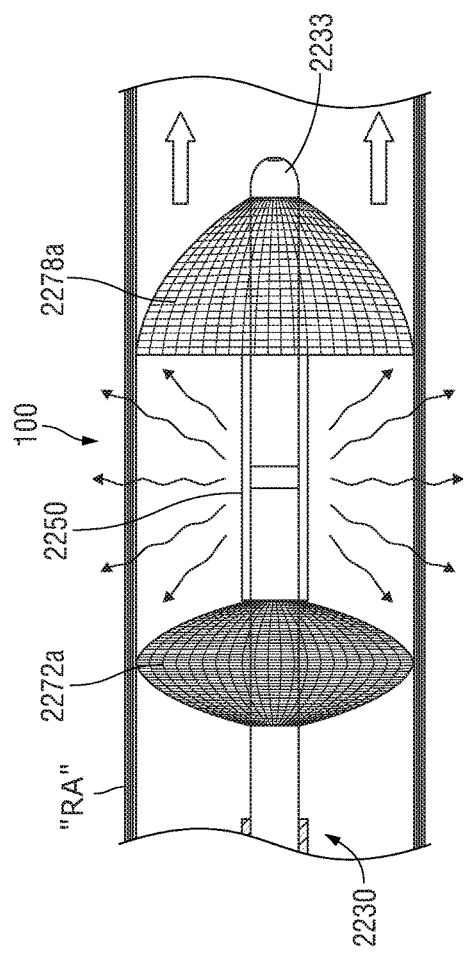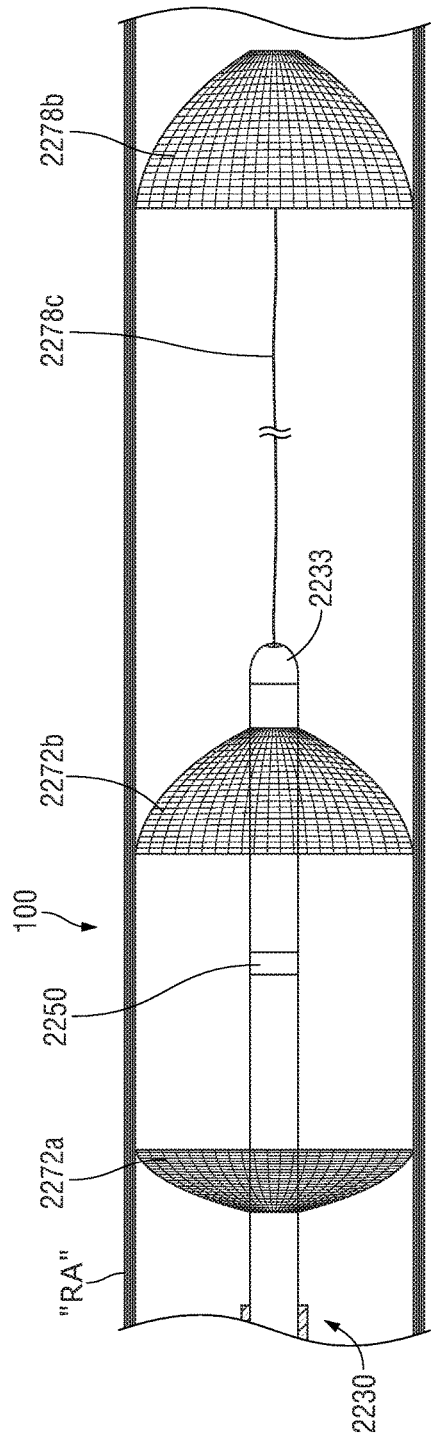

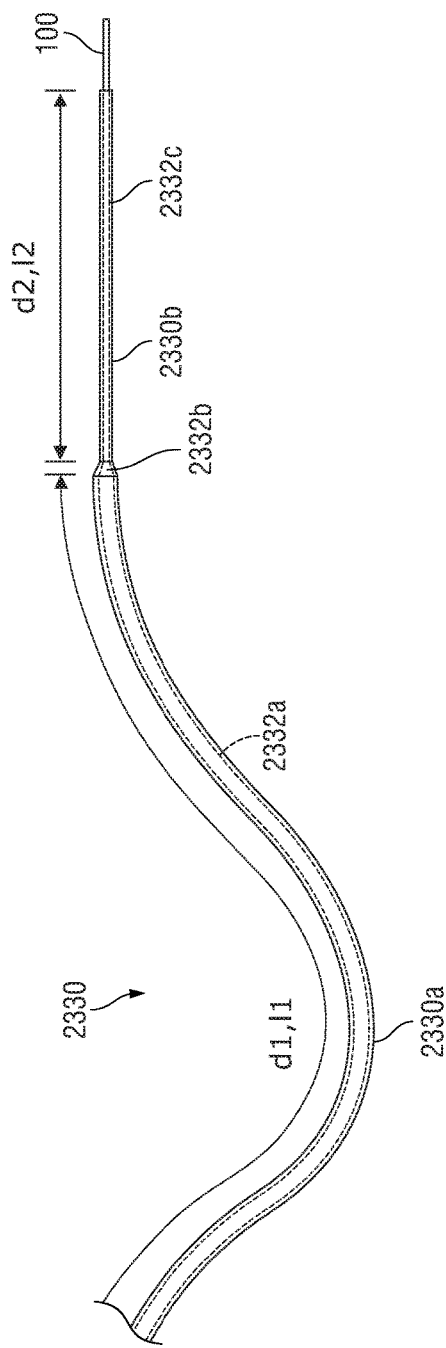
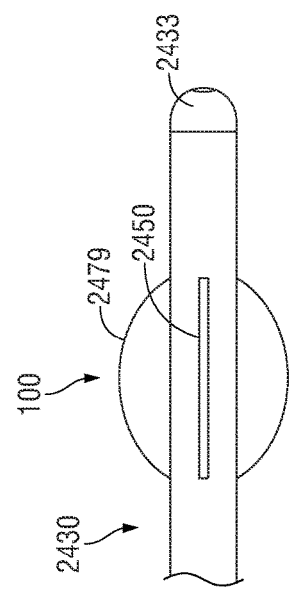
FIG. 23
FIG. 24

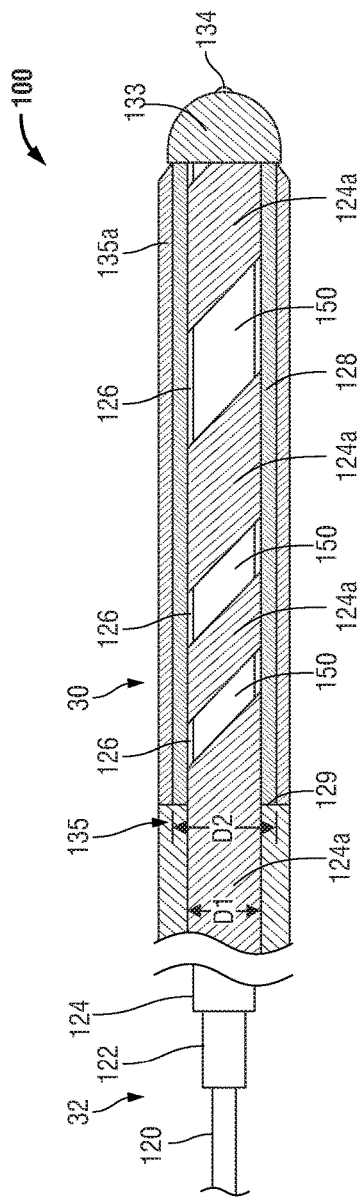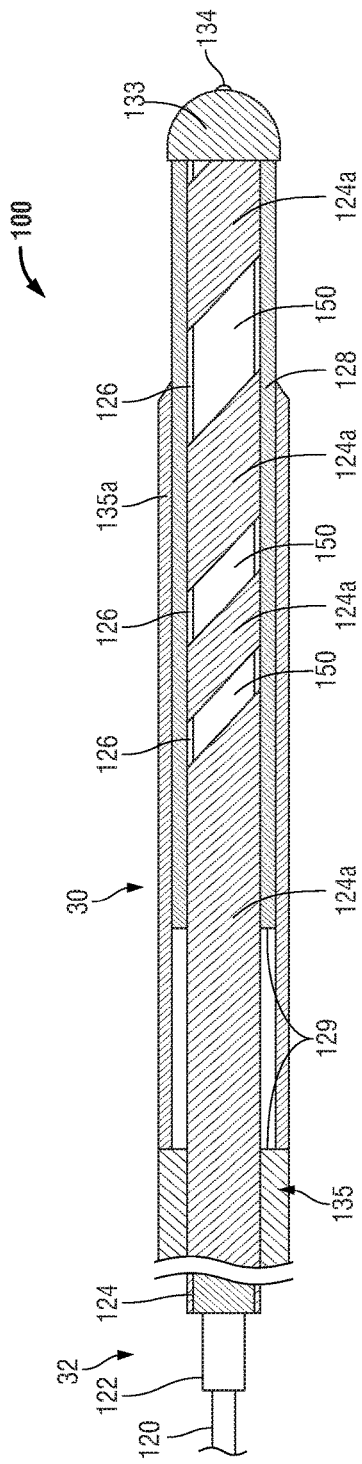
FIG. 42
FIG. 43

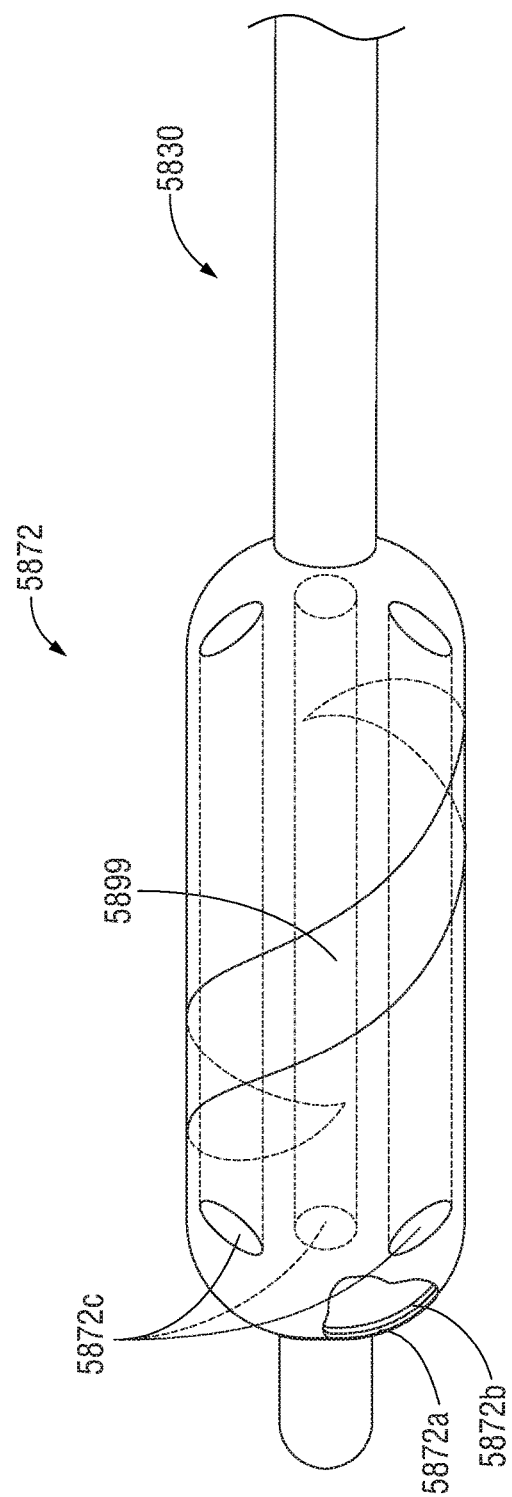

FLEXIBLE MICROWAVE CATHETERS FOR NATURAL OR ARTIFICIAL LUMENS

CROSS-REFERENCE TO RELATED APPLICATIONS

This application is a continuation application of U.S. application Ser. No. 14/110,652, filed on Oct. 8, 2013, now U.S. Pat. No. 9,358,066, which is a national stage entry of PCT/US2012/32818, filed on Apr. 9, 2012, which claims the benefit of and priority to U.S. Provisional Application Ser. No. 61/473,564, filed on Apr. 8, 2011, the entire contents of each which are incorporated herein by reference.

BACKGROUND

1. Technical Field

The present disclosure relates generally to flexible microwave catheters for natural or artificial lumens, and related methods of assembly and use.

2. Background of Related Art

Energy-based tissue treatment is known in the art. Various types of energy (e.g., electrical, ultrasonic, microwave, cryogenic, thermal, laser, and so forth) are applied to tissue to achieve a desired result. Disclosed are microwave catheters that enable microwave energy to be effectively delivered within a natural lumen within a body, to a location accessible through a natural or artificial lumen within a body, and/or a body structure such as, for example, an internal organ or body structure.

One such family of natural lumens includes lumens related to the gastrointestinal system (e.g., mouth, pharynx, esophagus, stomach, pancreatic structures, small and large bowel, bile duct, rectum and anus). Another such family of natural lumens includes lumens related to the auditory system (e.g., auditory canal and Eustachian tube). Yet another such family of natural lumens includes lumens related to the respiratory system (e.g., nasal vestibules, nasal cavity, sinus, trachea and the main and lobar bronchus). Another such family of natural lumens includes lumens related to the urinary system (e.g., urethra, bladder, ureter, prostate, and kidney). Another such family of natural lumens includes lumens related to the female reproductive system (e.g., vagina, cervix, uterus, fallopian tubes, and ovaries). Another such family of natural lumens includes lumens related to the male reproductive system (e.g., urethra, ejaculatory duct, vas deferens, and testis). Other natural lumens may require access via other means, such as common intravascular procedures to gain access to the lumens associated with the vascular system (aorta, arteries, veins, chambers of the heart). Additionally, the lumens associated with the vascular system may provide a pathway and/or access to all internal organs/body structures (e.g., access to the heart, lungs, kidneys, liver, stomach, intestine, colon, spleen, gall bladder and appendix).

It is believed that renal sympathetic nerve activity initiates, and sustains, the elevation of blood pressure. Chronic elevated blood pressure, or hypertension, is a significant cause of heart disease and death and afflicts millions worldwide. Generally, one having chronic blood pressure of over 140 mm Hg systolic and 90 mm Hg diastolic is classified as suffering from hypertension. Renal denervation has been found to reduce blood pressure. The renal nerves are bundled around the renal artery, which is readily accessible via the femoral artery. Targeting the renal nerves result in additional beneficial outcomes beyond blood pressure reduction which may become primary motivations for the procedure such as metabolic syndrome, heart failure, sleep apnea syndrome, renal insufficiency and diabetic nephropathy

SUMMARY

In an aspect of the present disclosure, a flexible microwave catheter is provided. The disclosed flexible microwave catheter includes a flexible coaxial cable having an inner conductor, an inner dielectric coaxially disposed about the inner conductor, and an outer conductor coaxially disposed about the inner dielectric. The disclosed flexible microwave catheter includes at least one feedpoint defining a microwave radiating portion of the flexible coaxial cable. A mesh structure having a collapsed configuration and an expanded configuration and disposed about the microwave radiating portion of the flexible coaxial cable is provided, wherein the mesh structure expands radially outward from the flexible microwave catheter thereby positioning the at least one feedpoint at the radial center of the mesh structure. In some aspects, the mesh structure of the flexible microwave catheter includes a conductive material that reduces propagation of denervation energy from the microwave radiating portion in an axial direction.

In some aspects, the mesh structure comprises an elastomeric balloon having a conductive pattern disposed on an inner surface thereof. In some aspects, the elastomeric balloon in an expanded configuration positions the at least one feed point at the radial center of the mesh structure. In some aspects, the conductive pattern defines a window on the inner surface of the elastomeric balloon, wherein the window is characterized by a lack of the conductive pattern. In some aspects, the mesh structure and the at least one feed point form a circumferentially balanced resonating structure. In some aspects, the mesh structure further includes a distal conductive end-cap mesh, a proximal conductive end-cap mesh, and a tubular mesh body formed between the distal end-cap mesh and the proximal end-cap mesh, wherein the distal conductive end-cap mesh and proximal conductive end-cap mesh reduce propagation of microwave energy from the microwave radiating portion in an axial direction. In some aspects, the tubular mesh body defines a window that radiates energy over 360 degrees along a longitudinal span of about 2 cm to about 3 cm.

In another aspect of the present disclosure, a flexible microwave catheter is provided having a flexible coaxial cable having an inner conductor, an inner dielectric coaxially disposed about the inner conductor, and an outer conductor coaxially disposed about the inner dielectric. At least one feed gap defines a microwave radiating portion of the flexible coaxial cable. A centering structure is disposed adjacent to the microwave radiating portion of the flexible coaxial cable and has a collapsed configuration and an expanded configuration wherein the centering structure extends radially outward from the flexible microwave catheter thereby positioning the at least one feedpoint at the radial center of the centering structure.

In some aspects, the centering structure of the flexible microwave catheter includes a stent-like expandable element that expands to a tubular shape when distally advanced from the confides of an outer sheath of the flexible microwave catheter. In some aspects, the stent-like expandable element defines a plurality of windows that radiate energy over 360 degrees along a longitudinal span. In some aspects, the centering structure includes a plurality of centering devices, at least one of the plurality of centering devices being disposed distal each of the at least one feed gaps and at least one of the plurality of centering devices being disposed proximal each of the at least one feed gaps. In some aspects, the plurality of centering devices reduces propagation of microwave energy from each of the at least one feed gaps in an axial direction. In some aspects, the at least one feed gap includes a first feed gap and a second feed gap and the centering structure further includes a first centering device operably associated with the first feed gap, and a second centering device operably associated with the second feed gap, wherein in the expanded configuration the first feed gap is at the radial center of the first centering device and the second feed gap is at the radial center of the second centering device. In some aspects, the first centering device and the second centering device each define a window therein that radiates microwave energy therethrough.

In some aspects, the centering structure includes an inflatable balloon housing, and a plurality of lobes formed on the inflatable balloon housing, wherein in an expanded configuration, a channel is formed between adjacent lobes of the plurality of lobes. In some aspects, the centering structure includes a plurality of fins equally spaced about the circumference of the flexible microwave catheter, wherein in a collapsed configuration the plurality of fins is restrained within an outer sheath of the flexible microwave catheter and in an expanded configuration the plurality of fins extends radially outward from the flexible microwave catheter. In some aspects, the plurality of fins is dimensioned to self-center the flexible microwave catheter in a fluid flow lumen via fluid/hydrodynamic forces generated by fluid flowing through the fluid flow lumen.

In some aspects, the centering structure includes a centering basket. The centering basket includes a first receiver for engaging the flexible microwave catheter, a second receiver for engaging the flexible microwave catheter, and a plurality of bands extending between the first receiver and the second receiver, each of the plurality of bands bowing outwardly and forming an arcuate path between the first receiver and the second receiver. In the collapsed configuration, the plurality of bands is compressed radially inwardly thereby elongating the centering basket. In an expanded configuration, the plurality of bands is uncompressed and extends radially outwardly. In some aspects, the first receiver fixedly engages the flexible microwave catheter and the second receiver slidably engages the flexible microwave catheter.

In some aspects, the centering structure includes at least two centering baskets. Each of the at least two centering baskets includes a first receiver for engaging the flexible microwave catheter, a second receiver for engaging the flexible microwave catheter, and a plurality of bands extending between the first receiver and the second receiver, each of the plurality of bands bowing outwardly and forming an arcuate path between the first receiver and the second receiver. In the collapsed configuration, the plurality of bands is compressed radially inwardly thereby elongating the centering basket and in an expanded configuration the plurality of bands is uncompressed and extends radially outwardly. In some aspects, the first receiver fixedly engages the flexible microwave catheter and the second receiver slidably engages the flexible microwave catheter. In some aspects, one of the at least one feed gaps is located between a first and a second of the at least two centering baskets.

In some aspects, the centering structure includes a plurality of paddles equally spaced about the circumference of the flexible microwave catheter. Each of the plurality of paddles is hingedly attached to the flexible microwave catheter, wherein in a collapsed configuration the plurality of paddles is adjacent and parallel the flexible microwave catheter and in expanded configuration the plurality of paddles extends perpendicular to, and extending radially outwardly from, the flexible microwave catheter.

In some aspects, the centering structure includes a plurality of helical ribs connected to the outer surface of the flexible microwave catheter an extending about the outer surface of the flexible microwave catheter in a helical-like fashion, wherein in collapsed configuration the plurality of helical ribs is compressed between the flexible coaxial cable and an inner surface of the outer sheath of the flexible microwave catheter and in an expanded configuration, the plurality of helical ribs extends radially from the flexible coaxial cable.

In yet another aspect of the present disclosure, a coupler for coupling a coaxial flexible cable, a fluid cooling system, and the outer sheath of a catheter, is provided. The coupler includes a fluid coupler body having a fluid inlet formed in the fluid coupler body and configured to operably couple to a source of cooling fluid and receive fluid therefrom, a fluid outlet formed in the fluid coupler body and configured to operably couple to a fluid discharge, a bypass bulb forming an aperture for slidably coupling with a coaxial cable, and an outer sheath coupler forming an aperture for coupling with an outer sheath of a catheter while forming a fluid-tight seal therewith. The coupler includes a fluid sealing system housed in the fluid coupler body having a distal sealing diaphragm configured to form a fluid-tight seal about an outer surface of an inflow lumen and a fluid-tight seal with an interior surface of the fluid coupler body defining an outflow plenum in fluid communication with the fluid outlet, the outflow plenum formed between a distal interior surface of the fluid coupler body, the outer surface of the inflow lumen, a distal side of the distal sealing diaphragm and the outer sheath coupler. The coupler includes a proximal sealing diaphragm configured to form a fluid-tight seal about an outer surface of the coaxial cable and a fluid-tight seal with an interior surface of the fluid coupler body thereby forming an inflow plenum in fluid communication with the fluid inlet, the outflow plenum formed between a proximal interior surface of the fluid coupler body, and a proximal side of the distal sealing diaphragm, a proximal side of the proximal sealing diaphragm.

In some aspects, the catheter is coaxially formed about the inner lumen, the inner lumen is coaxially formed about the coaxial cable, and the inflow plenum is in fluid communication with a fluid passageway formed between the outer surface of the coaxial cable and the inner surface of the inflow lumen. In some aspects, the catheter is coaxially formed about the inner lumen, the inner lumen is coaxially formed about the coaxial cable, the outflow plenum is in fluid communication with a fluid passageway formed between the outer surface of the inflow lumen and the inner surface of the outer sheath.

In some aspects, the catheter is coaxially formed about the inner lumen, the inner lumen is coaxially formed about the coaxial cable, the inflow plenum is in fluid communication with a fluid passageway formed between the outer surface of the coaxial cable and the inner surface of the inflow lumen, and the outflow plenum is in fluid communication with a fluid passageway formed between the outer surface of the inflow lumen and the inner surface of the outer sheath. In some aspects, the fluid coupler body slidably engages the coaxial cable.

In yet another aspect of the present disclosure, a microwave energy delivery device is provided. The microwave energy delivery device includes a coaxial feedline having an inner conductor, an inner dielectric insulator coaxially disposed about the inner conductor, and an outer conductor coaxially disposed about the inner dielectric. The microwave energy delivery device includes a radiating portion operably coupled to a distal end of the coaxial feedline. The radiating portion includes a radiating portion inner conductor operably coupled to and extending from a distal end of the coaxial feedline inner conductor; a shielding outer conductor helically wrapped about the radiating portion inner conductor and operably coupled to the coaxial feedline outer conductor, and a shielding dielectric positioned between the radiating portion inner conductor and the shielding outer conductor. The width of the shielding outer conductor varies according to the longitudinal position thereof along the coaxial feedline inner conductor. A cap operably couples to a distal end of the radiating portion inner conductor and the shielding outer conductor, and provides an electrical connection therebetween.

In some aspects, the microwave energy delivery device includes a temperature sensor disposed at a distal end thereof. In some aspects, a radiation pattern generated by the radiating portion is related to at least one of the variable width of the shielding outer conductor, or a variable helix angle of the shielding outer conductor.

In some aspects, the microwave energy delivery device includes a feed gap defined by a void formed between adjacent wraps of the shielding outer conductor. In some aspects, a feed gap ratio, defined by the ratio of a feed gap circumference and a shielding outer conductor circumference along a cross section, changes linearly from a proximal end of the shielding outer conductor to a distal end of the shielding outer conductor. In some aspects, the feed gap ratio changes non-linearly from a proximal end of the shielding outer conductor to a distal end of the shielding outer conductor. In some aspects, the feed gap ratio varies between 0% at the proximal end of the radiating portion and about 50% at the distal end of the radiating portion. In some aspects, the feed gap ratio varies between 0% on the proximal end of the radiating portion and about 100% on the distal end of the radiating portion.

In some aspects, the microwave energy delivery device generates a helical-shaped electromagnetic field that extends along the longitudinal length of the radiating portion. In some aspects, the helical-shaped electromagnetic field is related to a void formed between the individual wraps of the shielding outer conductor. In some aspects, the shielding outer conductor includes at least two helix turns. In some aspects, the cap provides an electrical connection between the radiating portion inner conductor and the shielding outer conductor.

In yet another aspect of the present disclosure, a microwave energy delivery device is provided that includes a coaxial feedline having an inner conductor, an inner dielectric insulator coaxially disposed about the inner conductor, and an outer conductor coaxially disposed about the inner dielectric. The microwave energy delivery device includes a radiating portion operably coupled to a distal end of the coaxial feedline that includes a radiating portion inner conductor operably coupled to and extending from a distal end of the coaxial feedline inner conductor, a shielding outer conductor helically wrapped about the radiating portion inner conductor and operably coupled to the coaxial feedline outer conductor, a shielding dielectric positioned between the radiating portion inner conductor and the shielding outer conductor. The helix angle of the shielding outer conductor varies according to the longitudinal position thereof along the coaxial feedline inner conductor. A cap operably couples to a distal end of at least one of the radiating portion inner conductor and the shielding outer conductor.

In some aspects, the microwave energy delivery device includes a feed gap defined by a void formed between adjacent wraps of the shielding outer conductor. In some aspects, a feed gap ratio, defined by the ratio of a feed gap circumference and a shielding outer conductor circumference along a cross section, change linearly from a proximal end of the shielding outer conductor to a distal end of the shielding outer conductor. In some aspects, the feed gap ratio changes non-linearly from a proximal end of the shielding outer conductor to a distal end of the shielding outer conductor. In some aspects, the feed gap ratio varies between 0% at the proximal end of the radiating portion and about 50% at the distal end of the radiating portion. In some aspects, the microwave energy delivery device generates a helical-shaped electromagnetic field that extends along the longitudinal length of the radiating portion. In some aspects, the helical-shaped electromagnetic field is related to a void formed between the individual wraps of the shielding outer conductor. In some aspects, a cap provides an electrical connection between the radiating portion inner conductor and the shielding outer conductor.

In still another aspect of the present disclosure, a microwave energy delivery device is provided that includes a coaxial feedline having an inner conductor, an inner dielectric insulator coaxially disposed about the inner conductor, and an outer conductor coaxially disposed about the inner dielectric. The disclosed microwave energy delivery device includes a radiating portion operably coupled to a distal end of the coaxial feedline. The radiating portion includes a radiating portion inner conductor operably coupled to and extending from a distal end of the coaxial feedline inner conductor, a shielding outer conductor helically wrapped about the radiating portion inner conductor and operably coupled to the coaxial feedline outer conductor, and a shielding dielectric positioned between the radiating portion inner conductor and the shielding outer conductor. The pitch of the helix angle of the shielding outer conductor varies according to the longitudinal position thereof along the coaxial feedline inner conductor. A cap is operably coupled to a distal end of at least one of the radiating portion inner conductor and the shielding outer conductor.

In some aspects, the microwave energy delivery includes a feed gap defined by a void formed between adjacent wraps of the shielding outer conductor. In some aspects, a feed gap ratio, defined by the ratio of a feed gap circumference and a shielding outer conductor circumference along a cross section, changes linearly from a proximal end of the shielding outer conductor to a distal end of the shielding outer conductor. In some aspects, the feed gap ratio changes non-linearly from a proximal end of the shielding outer conductor to a distal end of the shielding outer conductor. In some aspects, the feed gap ratio varies between 0% at the proximal end of the radiating portion and about 50% at the distal end of the radiating portion. In some aspects, the microwave energy delivery device generates a helical-shaped electromagnetic field that extends along the longitudinal length of the radiating portion. In some aspects, the helical-shaped electromagnetic field is related to a void formed between the individual wraps of the shielding outer conductor. In some aspects, the cap provides an electrical connection between the radiating portion inner conductor and the shielding outer conductor.

In yet another aspect of the present disclosure, a method for forming a resonating structure within a body lumen is provided. The method includes advancing a flexible microwave catheter with a body lumen of a patient, the flexible microwave catheter including a radiating portion on the distal end of the flexible microwave catheter, the radiating portion configured to receive a microwave energy signal at a microwave frequency, and at least one centering device adjacent the radiating portion and configured to deploy radially outward from the flexible microwave catheter. The radiating portion is positioning adjacent a targeted tissue. At least one centering device is deployed radially outward from the flexible microwave catheter and within the body lumen to position the radiating portion at the radial center of the body lumen. A circumferentially balanced resonating structure is formed within the body lumen via the radiating portion, and a microwave energy signal at the microwave frequency is delivered from the radiating portion, and resonates the body lumen at the microwave frequency.

In some aspects, the circumferentially balanced resonating structure radiates energy over 360 degrees along a longitudinal span of about 2 cm to about 3 cm. In some aspects, body lumen is the renal artery. In some aspects, the targeted tissue is the renal nerve and the circumferentially balanced resonating structure generates an electromagnetic field that denervates the targeted tissue.

In some aspects, the method further including the steps of providing a continuous fluid flow with the body lumen, and cooling at least a portion of the body lumen. In some aspects, the method further includes the step of continuing the delivery of the microwave energy signal until a sufficient amount of energy has been delivered to effectively damage the targeted tissue while preserving the critical structure of the body lumen.

In some aspects, the method further includes the steps of monitoring the temperature of the continuous fluid flow, and terminating the delivery of microwave energy if the monitored temperature exceeds a threshold temperature.

In some aspects, the body lumen is selected from at least one of a gastrointestinal lumen, an auditory lumen, a respiratory system lumen, urinary system lumen, a female reproductive system lumen, a male reproductive system lumen, a vascular system lumen, and an internal organ.

In some aspects, the method further includes expanding the body lumen to form a structure related to the microwave frequency.

In some aspects, the method further includes selecting the microwave frequency to resonate the body lumen based on the anatomical structure of the body lumen.

In some aspects, the method further includes monitoring a temperature within the body lumen, and terminating the delivery of the microwave energy signal when the temperature exceeds a threshold temperature.

In some aspects, the radiating portion includes a feed gap forming an open circuit in the flexible microwave catheter. In some aspects, the radiating portion includes a first feed gap and a second feed gap wherein the first and second feed gaps each form open circuits in the flexible microwave catheter.

In still another aspect of the present disclosure, a method for forming a resonating structure within a body lumen is presented. The presented method includes advancing a flexible microwave catheter with a body lumen of a patient. The flexible microwave catheter includes a radiating portion on the distal end of the flexible microwave catheter that is configured to receive a microwave energy signal at a microwave frequency, an electrically conductive mesh adjacent the radiating portion, and a retractable sheath configured to deploy the electrically conductive mesh about the radiating portion. The method includes positioning the radiating portion adjacent a targeted tissue, retracting the retractable sheath, deploying the electrically conductive mesh radially outward from the flexible microwave catheter and within the body lumen thereby centering the radiating portion at the radial center of the body lumen, forming a circumferentially balanced resonating structure within the body lumen via the radiating portion, and delivering the microwave energy signal at the microwave frequency to resonate the body lumen at the microwave frequency.

In some aspects, the method includes forming a window in the electrically conductive mesh, the window being characterized by a lack of material, and heating a region of the body lumen related to the window. In some aspects, the body lumen is a renal artery, the targeted tissue is a renal nerve, and heating the region of the body lumen related to the window at least partially denervates the kidney.

In some aspects, the method includes the step of cooling at least a portion of the renal artery.

In some aspects, the method includes the steps of providing a fluid cooling structure to enhance energy delivery and reduce heating of a least a portion of the flexible microwave catheter. The body lumen may be selected from at least one of a gastrointestinal lumen, an auditory lumen, a respiratory system lumen, urinary system lumen, a female reproductive system lumen, a male reproductive system lumen, a vascular system lumen, and an internal organ. In some aspects, the circumferentially balanced resonating structure radiates energy over 360 degrees along a longitudinal span of about 2 cm to about 3 cm.

In yet another aspect of the present disclosure, a method for implementing a microwave ablation waveguide is provided. The method includes the steps of selecting a lumen adapted to convey a fluid and formed from living biological tissue, longitudinally introducing an elongate inner conductor into the lumen, positioning a distal end of the elongate inner conductor at a location within the lumen adjacent to an anatomical feature of interest, centering at least a portion of the elongate inner conductor along the longitudinal axis of the lumen, energizing the elongate inner conductor with microwave ablation energy, and electrically shielding, with the lumen, the elongate inner conductor to reduce propagation of microwave ablation energy proximally of the anatomical feature of interest. In some aspects, the lumen is selected in accordance with a dielectric property of the fluid conveyed therein.

In some aspects, the centering step includes providing a centering member which facilitates the flow of the conveyed fluid therethrough. In some aspects, the method further includes the step of altering a dielectric property of the conveyed fluid. In some aspects, the method further includes the step of introducing a fluid amendment into the conveyed fluid. In some aspects, the fluid amendment is introduced into the conveyed fluid in response to a sensed electrical parameter. The sensed electrical parameter may be selected from the group consisting of a VSWR, a power factor, an impedance, a capacitance, an inductance, and a resistance. In some aspects, the fluid amendment is introduced into the conveyed fluid in response to a sensed biological parameter. The sensed biological parameter may be selected from the group consisting of a tissue temperature, a blood pressure, a heart rate, a respiratory rate, a tissue impedance, a blood oxygenation, and a neural response. In some aspects, the fluid amendment may be introduced into the conveyed fluid at continuous rate. In some aspects, the fluid amendment is introduced into the conveyed fluid at variable rate. The fluid amendment may be introduced into the conveyed fluid at a rate selected in response to a sensed electrical parameter and/or a sensed biological parameter.

In still another aspect of the present disclosure, a method of using a microwave ablation instrument having a radiation pattern is provided. The method includes selecting a lumen adapted to convey a fluid and formed from living biological tissue, longitudinally introducing the microwave ablation pattern into the lumen, positioning the radiation pattern of the microwave ablation instrument at a location adjacent to an anatomical feature of interest, energizing the microwave ablation instrument with microwave ablation energy, and electrically shielding, with the lumen, the microwave ablation instrument to reduce propagation of microwave ablation energy along the lumen proximally of the anatomical feature of interest.

In some aspects of the method, the lumen is selected in accordance with a dielectric property of the fluid conveyed therein. In some aspects, the method includes altering a dielectric property of the conveyed fluid. In some aspects, the method includes introducing a fluid amendment into the conveyed fluid. In some aspects, the fluid amendment is introduced into the conveyed fluid in response to a sensed electrical parameter. In some aspects the sensed electrical parameter is selected from the group consisting of a VSWR, a power factor, an impedance, a capacitance, an inductance, and a resistance. In some aspects, the fluid amendment is introduced into the conveyed fluid in response to a sensed biological parameter. In some aspects, the sensed biological parameter is selected from the group consisting of a tissue temperature, a blood pressure, a heart rate, a respiratory rate, a tissue impedance, a blood oxygenation, and a neural response.

In yet another aspect of the present disclosure, a method for implementing a microwave ablation waveguide is provided. The method includes the steps of selecting a lumen adapted to convey a fluid and formed from living biological tissue, introducing an elongate inner conductor into the lumen, positioning at least a portion of the elongate inner conductor within the lumen such that a longitudinal axis of the elongate inner conductor is positioned substantially parallel to and at a desired distance from a longitudinal axis of the lumen and proximate an anatomical feature of interest, and transferring microwave energy along the elongate inner conductor such that the lumen shields the inner conductor and allows a predetermined amount of microwave energy to propagate through the anatomical feature of interest. In some aspects of the method, the lumen is selected in accordance with a dielectric property of the fluid conveyed therein. In some aspects, the method includes altering a dielectric property of the conveyed fluid. In some aspects, the method includes introducing a fluid amendment into the conveyed fluid. In some aspects, the fluid amendment is introduced into the conveyed fluid in response to a sensed electrical parameter. In some aspects the sensed electrical parameter is selected from the group consisting of a VSWR, a power factor, an impedance, a capacitance, an inductance, and a resistance. In some aspects, the fluid amendment is introduced into the conveyed fluid in response to a sensed biological parameter. In some aspects, the sensed biological parameter is selected from the group consisting of a tissue temperature, a blood pressure, a heart rate, a respiratory rate, a tissue impedance, a blood oxygenation, and a neural response.

In still another aspect of the present disclosure, a method of using a microwave ablation instrument is provided. The method includes selecting a lumen adapted to convey a fluid and formed from living biological tissue, introducing a microwave antenna having an outer conductor with a structure capable of producing a predefined radiation pattern into the lumen, positioning the microwave antenna at a location proximate an anatomical feature of interest, and energizing the microwave antenna with microwave energy such that as the microwave energy emanates from the microwave antenna in the predetermined radiation pattern, the lumen controls the amount of microwave energy allowed to propagate therethrough. In some aspects of the method, the lumen is selected in accordance with a dielectric property of the fluid conveyed therein. In some aspects, the method includes altering a dielectric property of the conveyed fluid. In some aspects, the method includes introducing a fluid amendment into the conveyed fluid. In some aspects, the fluid amendment is introduced into the conveyed fluid in response to a sensed electrical parameter. In some aspects the sensed electrical parameter is selected from the group consisting of a VSWR, a power factor, an impedance, a capacitance, an inductance, and a resistance. In some aspects, the fluid amendment is introduced into the conveyed fluid in response to a sensed biological parameter. In some aspects, the sensed biological parameter is selected from the group consisting of a tissue temperature, a blood pressure, a heart rate, a respiratory rate, a tissue impedance, a blood oxygenation, and a neural response.

BRIEF DESCRIPTION OF THE DRAWINGS

The accompanying drawings, which are incorporated in, and constitute a part of this specification, illustrate various example embodiments of the present disclosure. Together with the general description given above, and the detailed description of the embodiments given below, the accompanying drawings serve to explain the principles of the system, apparatus and methods disclosed herein.

FIG. 9A is a side view of an embodiment of a flexible microwave catheter guide wire system according to some embodiments of the present disclosure;

FIGS. 9B-9C are longitudinal cross-sectional diagrams of the guide wire system of FIG. 9A;

FIGS. 10A-10B are longitudinal and transverse cross-sections, respectively, of an embodiment of a flexible microwave catheter centered in a renal artery in accordance with some embodiments of the present disclosure;

FIGS. 11A-11B are longitudinal and transverse cross-sections, respectively, of a flexible microwave catheter in an off-center position within a renal artery;

FIGS. 12A-12B are longitudinal and transverse cross-sections, respectively, of a flexible microwave catheter in an off-center position within a renal artery;

FIG. 22A is a side view of an embodiment of a radiating portion in accordance with some embodiments of the present disclosure having a distal mesh basket structure and a proximal mesh structure;

In FIG. 22B is a side view of an embodiment of a radiating portion in accordance with some embodiments of the present disclosure having a proximal mesh structure and a distal mesh basket structure operably coupled to the cap via a tether;

FIG. 23 is a perspective view of an embodiment of a stepped flexible microwave catheter with a stepped diameter in accordance with some embodiments of the present disclosure;

FIG. 24 is a side view of a radiating portion of an embodiment of a flexible microwave catheter that includes an inflatable centering balloon in accordance with some embodiments of the present disclosure;

FIG. 42 is a side view of a distal portion of the FIG. 7 embodiment of a microwave energy radiating device having a portion of the outer sheath removed and having a configurable portion in a fully retracted position;

FIG. 43 is a side view of a distal portion of the FIG. 7 embodiment of a microwave energy radiating device having a portion of the outer sheath removed and having a configurable portion in a partially deployed position;

FIG. 58A is a perspective view of an embodiment of a balloon centering device in a deflated configuration with a spiral window formed therein in accordance with some embodiments of the present disclosure;

DETAILED DESCRIPTION

Particular embodiments of the present disclosure are described hereinbelow with reference to the accompanying drawings; however, the disclosed embodiments are merely examples of the disclosure, which may be embodied in various forms. Well-known and/or repetitive functions and constructions are not described in detail to avoid obscuring the present disclosure in unnecessary or redundant detail. Therefore, the terminology used herein for the purpose of describing particular embodiments, specific structural and functional details disclosed herein, as well as the specific use disclosed herein, are not to be interpreted as limiting, but merely as a basis for the claims and as a representative basis for teaching one skilled in the art to variously employ the present disclosure in virtually any appropriately detailed structure. In this description, as well as the drawings, like-referenced numbers represent elements which may perform the same, similar, or equivalent functions.

As used herein, the term "proximal," as is traditional, shall refer to the end of the instrument that is closer to the user, while the term "distal" shall refer to the end that is farther from the user. As used herein, terms referencing orientation, e.g., "top", "bottom", "up", "down", "left", "right", "o'clock", and the like, are used for illustrative purposes with reference to the figures and corresponding axes and features shown therein. It is to be understood that embodiments in accordance with the present disclosure may be practiced in any orientation without limitation.

As discussed hereinabove, a flexible microwave catheter may be used to perform a procedure by utilizing a natural or artificial lumen. One particular procedure discussed herein is a denervation procedure that utilizes the vascular system to access a kidney. Embodiments are disclosed herein whereby the energy and antenna characteristics are designed to enable application of microwave denervation energy to a targeted neurological structure, such as without limitation, a sympathetic nerve bundle surrounding a renal artery, although the devices and methods may be utilized in any other procedure and on any other body lumen, organ or bodily structure. This particular procedure is only used to demonstrate general concepts and the use of some embodiments in accordance with the present disclosure. For example, embodiments of the flexible microwave catheter disclosed herein may also be used to perform procedures in the respiratory system, e.g., to treat tumors in the upper respiratory tract and the lungs, as well as to treat asthma, chronic obstructive pulmonary disease (COPD) emphysema, etc.

Figure 1:
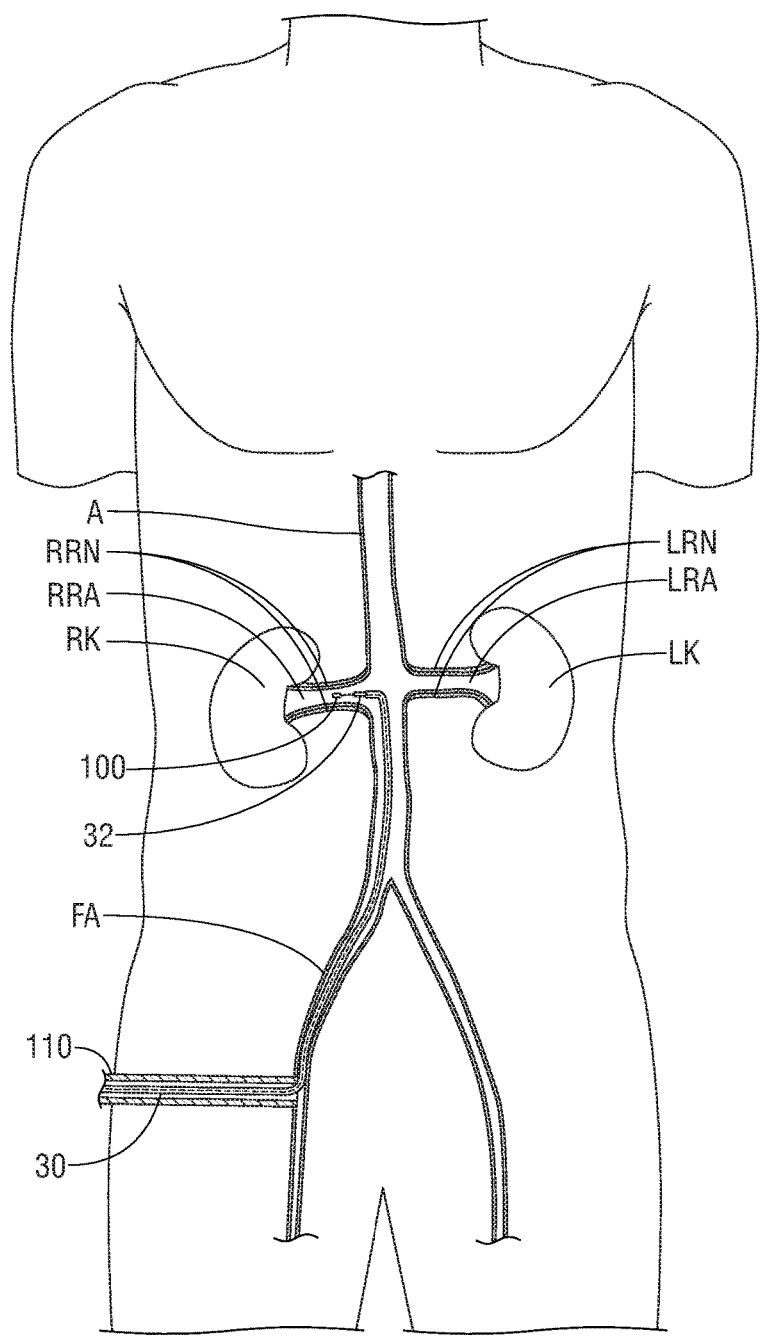
FIG. 1 is a partial cross-sectional view of a flexible microwave catheter accessing the renal artery via the vascular system according to some embodiments of the present disclosure.

As illustrated in FIG. 1, the disclosed flexible microwave catheter 30 is percutaneously introduced into the femoral artery FA through an arterial catheter 110 and positioned within the right renal artery RRA and adjacent to the right renal nerve bundle RRN. The flexible microwave catheter 30 includes a radiating portion 100 that cooperates advantageously with the right and/or left renal artery RRA, LRA (hereinafter, "renal artery RA") physiology to deliver denervation energy to the respective right and/or left renal nerve bundles RRN, LRN (hereinafter "renal nerve RN") while minimizing collateral damage to the respective arterial vessel and related anatomical structures. In the discussion to follow, the renal nerve RN and the renal artery RA are used to illustrate embodiments in accordance with the present disclosure however it is to be understood the disclosed embodiments may be used with either the right renal artery RRA or the left renal artery LRA to deliver denervation energy to the respective right renal nerve bundle RRN and left renal nerve bundle LRN.

Elevated sympathetic nerve activity initiates and sustains the elevation of blood pressure. The renal nerve bundle RN include the renal sympathetic nerves (efferent and afferent) that are bundled around the renal artery RA. As such, the renal artery RA facilitates access to the renal nerve bundles RN through the femoral artery FA and/or the abdominal aorta A. The flexible microwave catheter 30 places the radiating portion 100 of a microwave energy applicator in close proximity to the renal nerve bundles RN. Once positioned in the renal artery RA, the radiating portion 100 can focus energy from within the renal artery RA toward the respective renal nerves bundle RN surrounding the renal artery RA in an effort to denervate the kidneys and ultimately reduce blood pressure.

As discussed in greater detail hereinbelow, the various embodiments include structures that allow for the application of electrosurgical energy to one or more locations within the renal artery RA (or other lumen or body structure) without compromising the overall integrity of the vessel wall. In some embodiments, the energy delivery structure does not mechanically contact the vessel wall, thereby reducing complications from perforation or stenosis as a result of mechanical damage. In some embodiments, the energy delivery structure directs energy to a particular portion of one or more layers of the body lumen/body structure thereby maintaining the overall viability of the body lumen/body structure. In some embodiments blood or fluid flow with the vessel contributes to cooling of inner layers of the vessel wall, thereby reducing unwanted heating and collateral damage to the vessel wall while enabling energy delivery to the outer layer proximate the renal nerves.

The systems, devices and methods described herein provide spatial energy control of microwave energy. Spatial energy control incorporates three factors, namely, repeatability of energy delivery, precise control of the delivered energy, and efficient delivery of energy. The factors that contribute to spatial energy control include thermal management, dielectric management, buffering, and electrical current control. These factors can be controlled through systems, devices and methods that operate in tandem with the surrounding anatomical structure, effectively incorporating the surrounding tissue as part of the microwave device.

Microwave energy systems and devices exhibit behaviors that are fundamentally different than behaviors of systems and devices using lower frequency RF signals. For example, the operation and functionality of a RF system, using low frequency "RF" signals, requires an electrical circuit that includes a closed-loop connection of conductive materials, e.g., a completed electrical circuit. The behavior of the circuit is directly dependant on the electrical properties of the closed connection of conductive materials. The most obvious behavior and example being that in a RF circuit, a break in the closed-loop connection of conductive materials, e.g., an open circuit, renders the system inoperable.

Microwave systems, on the other hand, transmit microwave energy signals through waveguides. The most common example of a waveguide being a coaxial cable that consists of an inner conductor positioned coaxially within an outer conductor by a dielectric. Unlike a RF circuit, creating an open circuit (e.g., slot) in the coaxial outer conductor does not render the system inoperable. Instead, the waveguide continues to convey the microwave signal, and the slot radiates a portion of the energy being transmitted by the waveguide.

As such, some embodiments of the systems, devices and methods described herein incorporate a portion of the anatomical structure into the design of the microwave energy delivery system. More specifically, the cylindrical structure of natural body lumens and other body structures that are concentric in nature can be utilized to operate in conjunction with, and become part of, a waveguide used by the devices described herein to transmit microwave energy.

The use of the natural lumen structure and/or body structure as a component of the radiating structure enables enhanced energy delivery techniques, such as focusing microwave energy-induced thermal therapy to a targeted anatomy. For example, as noted above structures described herein are capable of targeting the smooth muscle layer within the bronchus of the lungs, and are capable of targeting the renal nerves within the adventitia layer of the renal nerve. Additionally, the use of the devices described herein within the lumen structures enables the formation of a directional radiating pattern to specific sections of the lumen.

In some embodiments, the devices described herein also utilize the fluids present in the natural body lumens to perform dielectric loading of the anatomical radiating structure. The properties of the fluid are incorporated into the design of the microwave radiator as a design component. For example, bodily fluids may form a dielectric layer and/or a conductive layer of an anatomical waveguide and the properties of the fluid are utilized in the design, such as, for example, for impedance matching, energy efficiency, wavelength buffering, and radiation pattern control and shaping.

The fluid's dielectric properties may be externally manipulated and/or adjusted by introducing (and/or eliminating) one or more elements into the fluid. For example, fluids high in water content exhibit a high dielectric constant that enable shaping of microwave fields around radiation structures. As such, the dielectric properties of blood may be adjusted by modifying the plasma composition and adjusting the ratio of water, protein, inorganic salts, and organic substances. Similarly, the dielectric properties of blood may be adjusted by changing the glucose levels. In this manner, changing the dielectric property of the fluids may effectuate changes in the performance of the devices described herein, since the bodily fluids can be used as the dielectric layer in the anatomical waveguides discussed herein.

The systems, devices, and methods described herein also utilize fluids (e.g., natural or externally introduced) within the natural body lumens for thermal management of one or more layers of the anatomical waveguide and/or one or more components of the devices described herein. Fluids mitigate thermal damage through fluid cooling of non-target anatomy within the heating profile of the devices. Additionally, the fluid flow may be manipulated by adjusting the device(s) (e.g., increasing or decreasing a blockage thereby decreasing or increasing fluid flow), adjusting the natural flow rate (e.g., directing fluid flow to a particular body portion by restricting flow at another body portion) and/or adjusting a body function (e.g., elevating the heart rate thereby increasing the rate of blood flow through the body). Fluid temperature may also be manipulated by providing an external or an internal heat sink.

Centering of the devices described herein increases the predictability and repeatability of energy delivery to the targeted anatomical structures. The centering devices described herein include passive centering devices (e.g., utilizing the natural flow of fluid in a lumen for centering) or active devices that actively and/or positively position the radiating portion in the lumen.

Figure 2:
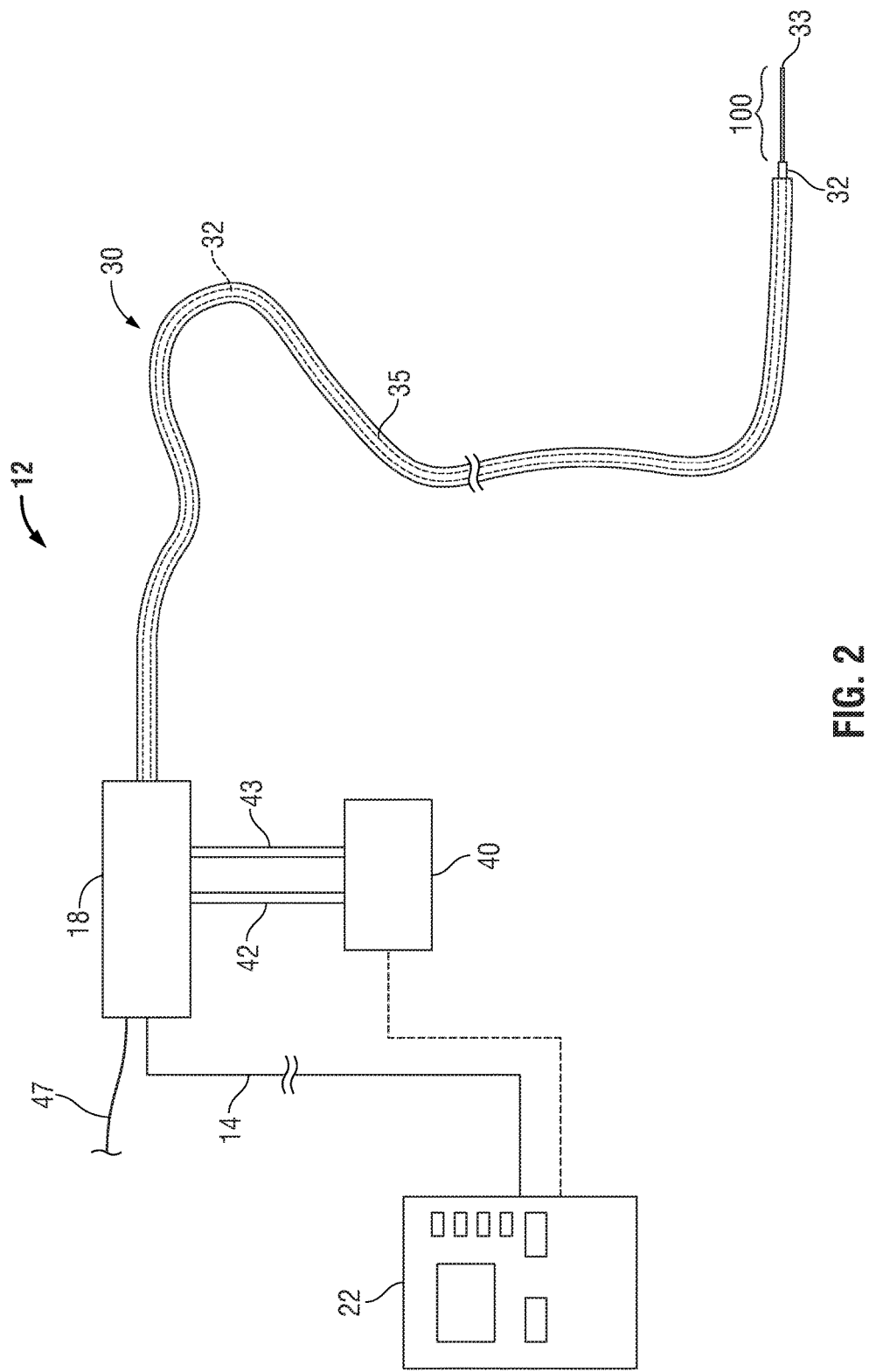
FIG. 2 is a system diagram of a microwave energy delivery system having a flexible microwave catheter according to some embodiments of the present disclosure.

In embodiments in accordance with the present disclosure, a microwave energy delivery system 12 with a flexible microwave catheter 30 is provided and illustrated in FIG. 2. Microwave system 12 includes a microwave generator 22, transmission line 14, a fluid cooling system 40, catheter hub 18 and a flexible microwave catheter 30. Some embodiments may include a guide wire 47 for guiding and/or positioning the radiating portion 100 of the flexible microwave catheter 30 to a desirable position.

Flexible microwave catheter 30, in accordance with the present disclosure, includes a flexible coaxial cable 32, or feedline, that is operably connectable to the microwave generator 22 (e.g., through the catheter hub 18 and transmission line 14). Flexible microwave catheter 30 includes a radiating portion 100 positioned on a distal-most end thereof. In some embodiments, as discussed hereinbelow and illustrated in the accompanying drawings, the radiating portion 100 is deployable from the outer sheath 35 of flexible microwave catheter 30 and includes an exposed cap 33 on the distal-most end thereof.

One or more parameters of the microwave energy signal may be related to the targeted tissue. In some embodiments, the frequency of the microwave energy signal generated by the microwave generator 22 is related to the diameter of the body lumen. For example, the diameter of the renal artery may require a microwave signal at first frequency, the diameter of the esophagus may require a microwave signal at a second frequency and the diameter of the vaginal cavity may require a microwave signal at a third frequency. Some applications, such as providing treatment to the respiratory system, may require the frequency to vary with the position of the radiating portion within the body lumen due to the varying diameter along the body lumen (e.g., airways).

Catheter hub 18 is disposed at a proximal end of flexible microwave catheter 30 and is configured to enable the operable coupling of a source of denervating energy (e.g., a microwave generator 22) to the transmission line 14. Catheter hub 18 provides an exchange of cooling fluid between the flexible microwave catheter 30 and the fluid cooling system 40. Fluid cooling system 40 provides a source of coolant to the inflow conduit 42 and receives coolant evacuated from the catheter hub 18 through an outflow conduit 43 connected to a fluid receiving destination (e.g., a receptacle, reservoir, or drain).

Figure 3:
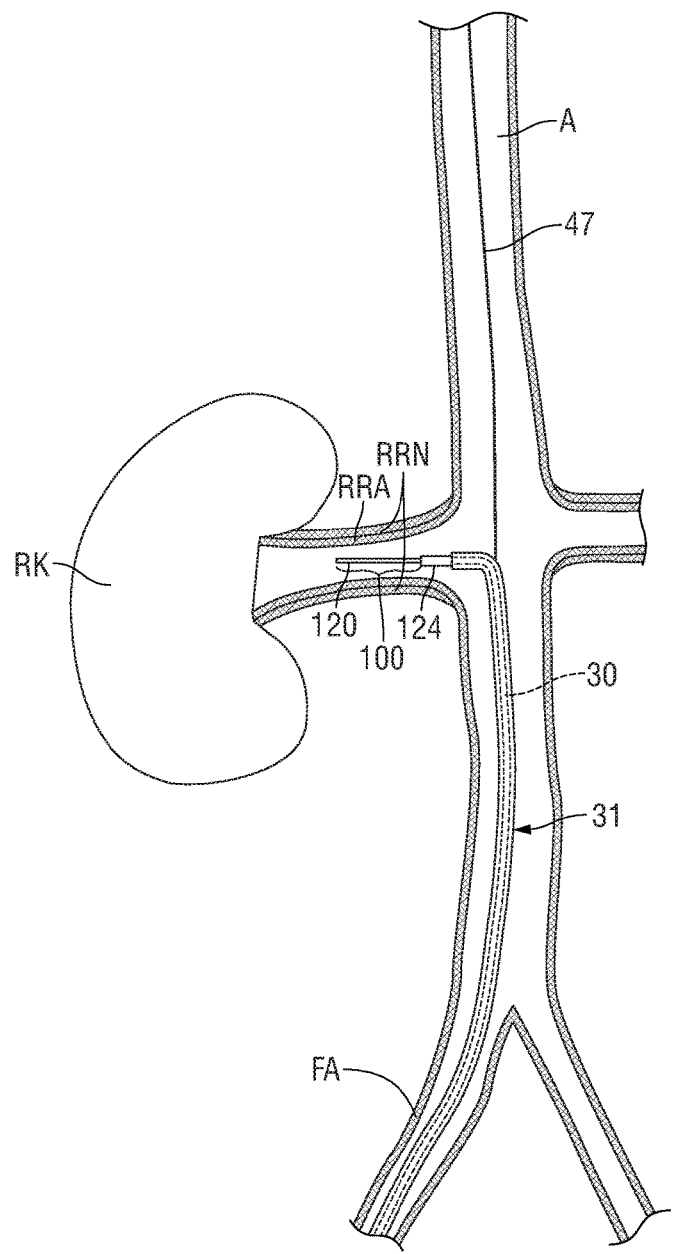
FIG. 3 is a partial cross-sectional view of a flexible microwave catheter accessing the renal artery via the vascular system in accordance with some embodiments of the present disclosure.

FIG. 3 illustrates a flexible microwave catheter 30 in accordance with the present disclosure positioned in a renal artery RA. In some embodiments, the flexible microwave catheter 30 is maneuvered through a long sheath 31 initially positioned in the femoral artery and/or the aorta. A distal end of the long sheath 31 is positioned at a proximal end of the renal artery RA. Flexible microwave catheter 30 is guided through the long sheath 31 and into the renal artery RA, e.g., extended past the distal end of the long sheath 31 and positioned within the renal artery RA. In some embodiments, a guide wire 47 may be utilized to guide and/or position the long sheath 31 or the flexible microwave catheter 30 as described herein.

The radiating portion 100 of the flexible microwave catheter 30 is positioned within the renal artery RA and receives a microwave energy signal from the microwave generator 22 (see FIG. 2). At least a portion of the microwave energy signal is selectively delivered to at least a portion of the renal artery RA. Some embodiments described herein, and illustrated in the accompanying figures, advantageously utilize the renal artery physiology in the application of microwave energy, thereby inducing modification of the target tissue. With respect to a renal denervation procedure, the target tissue for treating hypertension includes at least a portion of the renal nerves RRN, LRN.

Figure 4A:
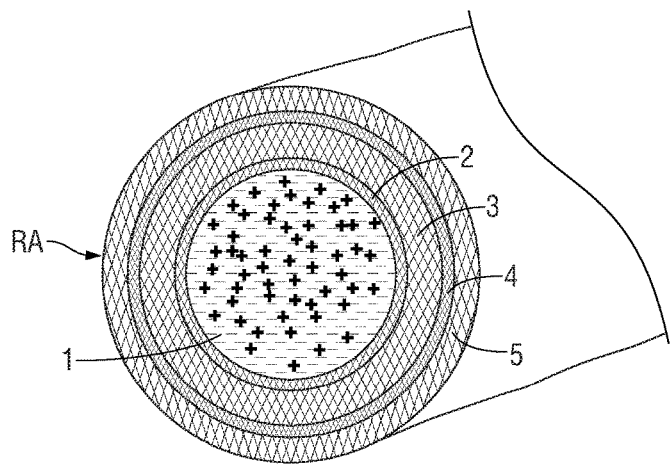
FIG. 4A is a transverse cross-sectional view of the anatomical structure of a renal artery.

The anatomical structure of a natural body lumen (e.g., a renal artery RA), is illustrated in FIG. 4A. The innermost layer and/or core of the lumen that forms the fluid pathway of the lumen (e.g., the hollow body formed by the lumen). The fluid 1 contained in an artery is typically a bodily fluid (e.g., blood) although a non-bodily fluid (e.g., saline, air, or any other suitable fluid) may be utilized and/or introduced. Other natural body lumens may contain other body fluids (e.g., blood, mucus, urine, bile, air, and any combination thereof) or the lumen may contain an externally-introduced fluid (e.g., air, saline, and water), or any combination thereof.

The first layer of the body lumen (e.g., renal artery RA) is the intima layer 2 formed of about 50% elastin and about 50% cartilage. Other natural lumens may include a similar elastin and/or cartilage-like layer such, as for example, a mucus layer, a mucus membrane layer or the stratum corneum. The second layer of the body lumen (e.g., renal artery RA) is a smooth muscle layer 3. Examples of other natural lumens that include a layer of smooth muscle are the esophagus, stomach, intestines, bronchi, uterus, urethra and the bladder. The third layer in a body lumen (e.g., renal artery RA) is the adventitia layer 4 (a.k.a., the tunica externa). Adventitia layer 4 is the outermost connective tissue covering most organs, vessels and other body structures. The outermost adventitia layer 4, as with many body lumens, is covered with an outermost fat layer 5.

While each body lumen and bodily structure is functionally different, the general structures of body lumens and many bodily structures have structural similarities. For example, the first layer of the esophageal wall is the mucosa (e.g., mucus membrane), the second layer is the submucosa which includes esophageal glands, the third layer is the muscular is (e.g., smooth muscle), and the outermost layer is the adventitia layer which is covered by fat. Variations in the natural body lumens and body structures do not change the general operation of the devices, systems, and methods described herein, and may only require slight variations in one or more operational parameters thereof.

Figure 4B:
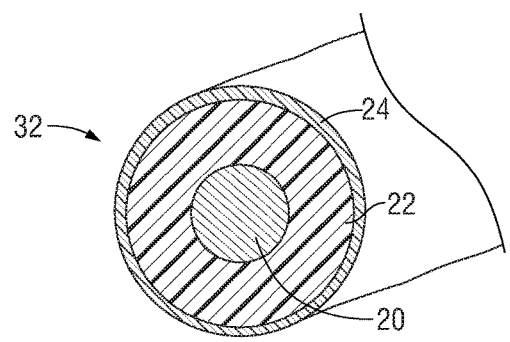
FIG. 4B is a transverse cross-sectional view of an embodiment of a flexible coaxial cable in accordance with some embodiments of the present disclosure.

FIG. 4B illustrates the coaxial arrangement of a flexible coaxial cable 32 that includes an inner conductor 20, a dielectric layer 22 and an outer conductor 24. Drawing an analogy between the structures that form a natural body lumen in FIG. 4A and the structures that form a flexible coaxial cable 32 in FIG. 4B, the outer conductor 24 is analogous to the adventitia layer 4 and/or the outermost fat layer 5 and the dielectric layer 22 is analogous to the fluid 1 in the hollow body.

Figure 4C:
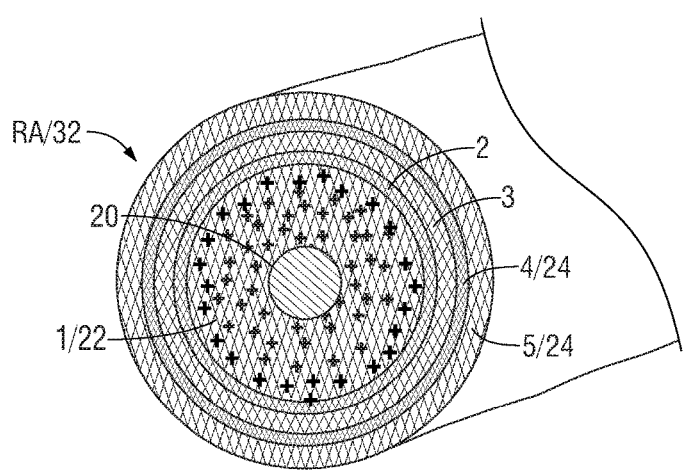
FIG. 4C is a transverse cross-sectional view of an embodiment of a microwave waveguide structure within a natural body lumen in accordance with some embodiments of the present disclosure.

FIG. 4C illustrates the formation of a microwave waveguide structure RA/32 within a body lumen (e.g., renal artery RA) wherein the microwave structure RA/32 includes an inner conductor 20 (e.g., conductor positioned in the hollow body 1), a dielectric (e.g., fluid in the hollow body 1/22) and an outer conductor (e.g., formed from the outermost fat layer 5/24). As such, when applied with a microwave energy signal, the anatomy becomes part of the microwave waveguide structure wherein the dielectric constant and loss factors are related to the physiology and composition of the natural body lumen and/or bodily structure.

Energy losses in any waveguide structure include dielectric losses (e.g., loss through the dielectric material) and conductor losses (e.g., losses in the conductors forming the waveguide). As such, the dielectric losses are losses in the anatomy that forms the dielectric (e.g., fluid 1 in the hollow body) and conductor losses are losses in the structures and/or anatomy that form the inner conductor 20 and the outer conductor 4/24 and 5/24.

In some embodiments, forming a resonating microwave waveguide structure with the layers that form the anatomical structure of the renal artery creates an inefficient waveguide through which the losses in the anatomical structure can heat target tissue to damaging temperature levels. For example, the renal nerves LRN, RRN (e.g., renal efferent nerves and the renal afferent nerves) reside within the adventitia layer 4 that is surrounded by the fat layer 5. The adventitia layer 4 and the fat layer 5 exhibit properties that resemble that of a conductive material and properties that resemble that of a dielectric material. As such, microwave currents generated by an electromagnetic field in the adventitia layer 4 and the fat layer travel on the surface of each layer (conductive property) and travel through each layer (dielectric properties). As such, losses in the adventitia layer 4 and the fat layer 5 include conductive and dielectric losses.

Figure 5:
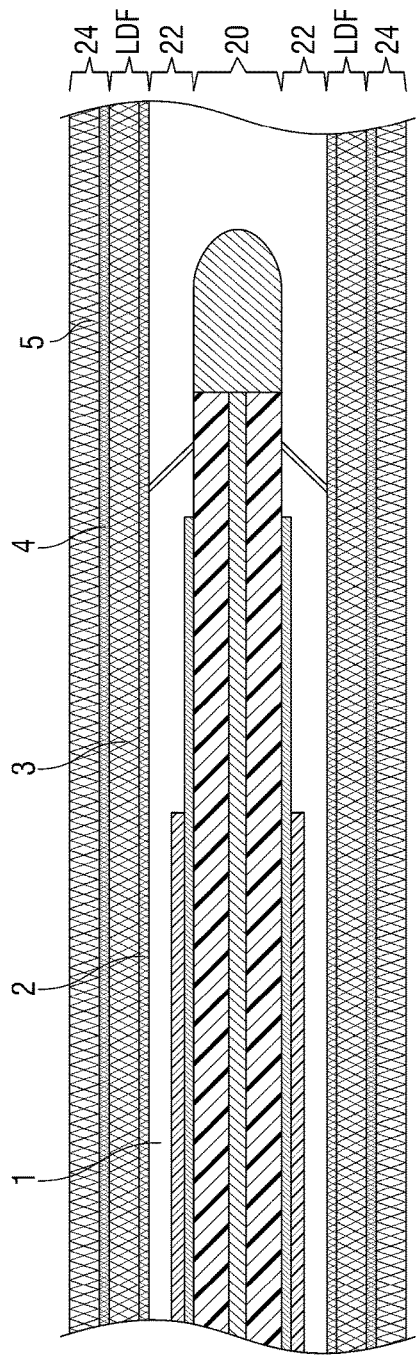
FIG. 5 is a longitudinal cross-section of an embodiment of a microwave waveguide structure in accordance with some embodiments of the present disclosure.

In some embodiments, as illustrated in FIG. 5, the adventitia layer 4 may be viewed as being analogous to a lossy dielectric film (LDF) formed on an inner surface of a coaxial cable outer conductor 24 (e.g., formed on an inner surface of the fat layer 5). High energy absorption rates can therefore target the adventitia layer 4 and damage the nerves contained therewithin and/or adjacent thereto. Due to the rate of blood flow through the renal artery RA, the microwave thermal energy that may induce tissue damage may be tempered in the body structure (e.g., renal artery RA) thereby resulting in the preservation of the intima layer 2 and smooth muscle layer 3 and maintaining a viable arterial structure.

Figure 6A:
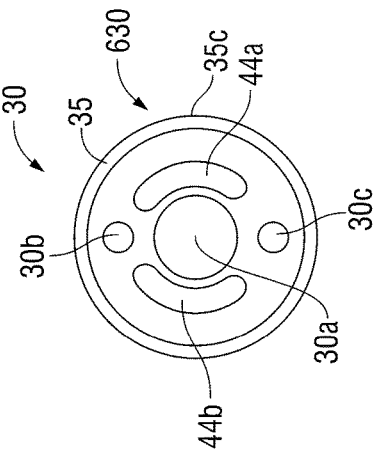
FIG. 6A is a block diagram of a catheter hub according to some embodiments of the present disclosure.
Figure 6B:
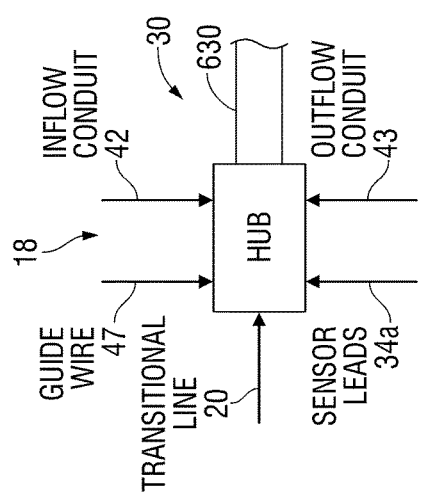
FIG. 6B is a transverse cross-section of an embodiment of a flexible microwave catheter according to some embodiments of the present disclosure.

FIG. 6A illustrates a block diagram of the catheter hub 18 in accordance with some embodiments of the present disclosure. The catheter hub 18 may include five-ports and may be disposed at a proximal end of a multi-lumen tube 630, as illustrated in FIG. 6B. Catheter hub 18 may include connectors to facilitate operable coupling of the five lumens with corresponding elements of the generator, coolant source and return, and so forth. Catheter hub 18 is disposed at a proximal end of the flexible microwave catheter 30 and configured to enable the operable coupling of various systems that may connect to the flexible microwave catheter 30. The catheter hub 18 connects to a transmission line 14 and receives denervating energy, generated by a source of denervation energy (e.g., a microwave generator 22), therefrom. The catheter hub 18 may connect to a fluid cooling system 40 and may provide an exchange of cooling fluid between the flexible microwave catheter 30 and the fluid cooling system 40. The fluid cooling system 40 provides a source of coolant to the inflow conduit 42, receives coolant evacuated from the catheter hub 18 through an outflow conduit 43, and deposits the evacuated coolant to a receiving destination (e.g., a receptacle, reservoir, or drain). The catheter hub 18 may connect to a guide wire 47 for guiding and positioning the flexible microwave catheter 30. The catheter hub 18 may also connect to one or more sensor leads 34a that operably couple one or more sensors 1534 (see FIG. 15A) on the flexible microwave catheter 30 to a control system or sensor monitoring system housed in the microwave generator 22.

As illustrated in FIG. 6B, the flexible microwave catheter 30 in accordance with the present disclosure includes a multi-lumen tube 630 having a multi-port catheter hub 18 at a proximal end thereof (see FIG. 2). The multi-lumen tube 630 has a generally elongated cylindrical outer surface having formed therein a plurality of conduits, passageways and/or lumens disposed longitudinally therein. The multi-lumen tube 630 may be formed by any suitable manner of manufacture, such as without limitation, extrusion. The multi-lumen tube 630 may include a central lumen (e.g., flexible coaxial cable lumen 32a) having a generally circular cross-section extending axially therethrough and dimensioned to accommodate a flexible coaxial feedline 32 (see FIG. 2). A first pair of lumens (e.g., guide wire tracking lumen 30b and sensor lead lumen 30c) having a generally a circular cross-section may be positioned on opposing sides of the central lumen (e.g., at a 12 o'clock and 6 o'clock position) that are adapted to accommodate, e.g., a guidewire 47 and a sensor conductor 34a (see FIG. 8A), respectively. A second pair of lumens (e.g., inflow fluid passageway 44a and outflow fluid passageway 44b) having a generally arcuate cross-section may be positioned on opposing sides of the central lumen, between the first pair of lumens (e.g., at 9 o'clock and 3 o'clock, respectively), to accommodate coolant inflow and coolant outflow, respectively.

Figure 7:
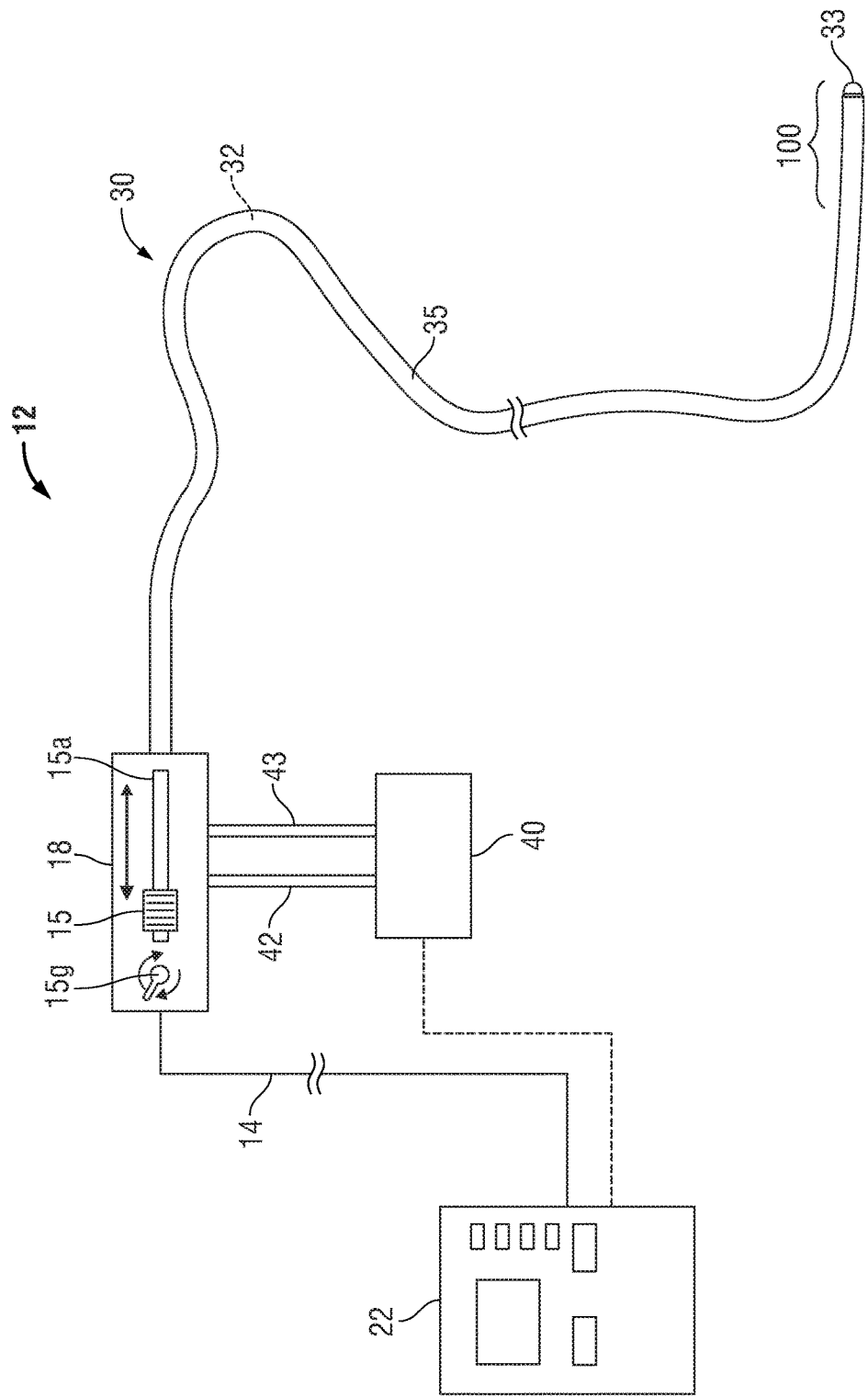
FIG. 7 is a system diagram of an embodiment of a microwave energy delivery system in accordance with some embodiments of the present disclosure having a flexible microwave catheter with at least a part of the radiating portion housed in the outer sheath of the flexible microwave catheter.

The outer sheath 35 of the flexible microwave catheter 30 may include braiding and/or windings to improve strength, to resist kinking, and/or to provide flexibility while maintaining sufficient stiffness. Outer sheath 35 may include one or more steering wires (not shown) to facilitate steering and manipulation of the flexible microwave catheter 30 to a desirable position. Outer sheath 35 may include a dielectric coating, such as, for example, Parylene, on the outer surface 35c of the outer lumen to reduce blood clotting As illustrated in FIG. 7, in some embodiments the flexible coaxial cable 32 and at least part of the radiating portion are housed in the outer sheath 35 of the flexible microwave catheter 30. Catheter hub 18 includes an actuator 15 housed in the catheter hub 18 and coupled to the radiating portion 100. Actuator 15 is configured to deploy the radiating portion 100 and cap 33 distally from the outer sheath 35, as discussed in detail hereinbelow.

Figure 8A:
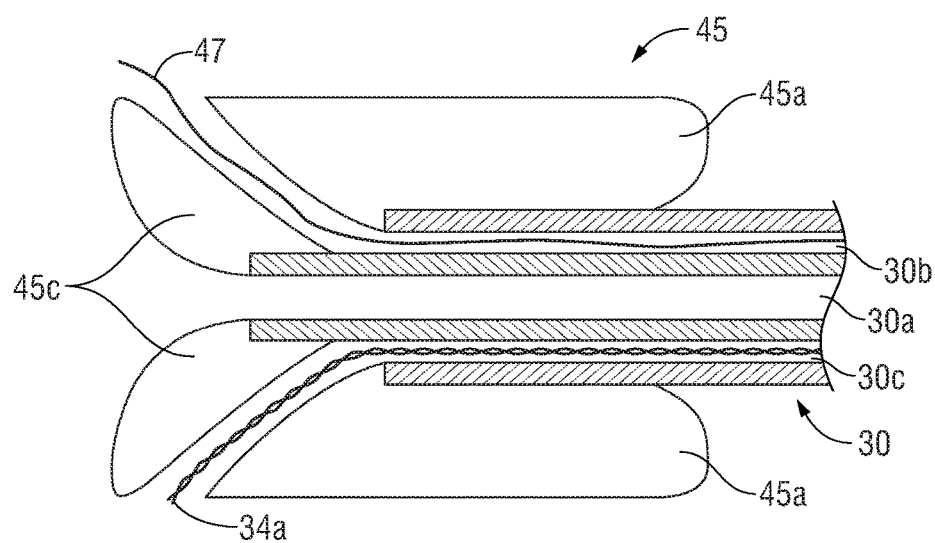
FIGS. 8A-8C illustrate embodiments of longitudinal cross-sections of catheter hub couplers according to some embodiments of the present disclosure.
Figure 8B:
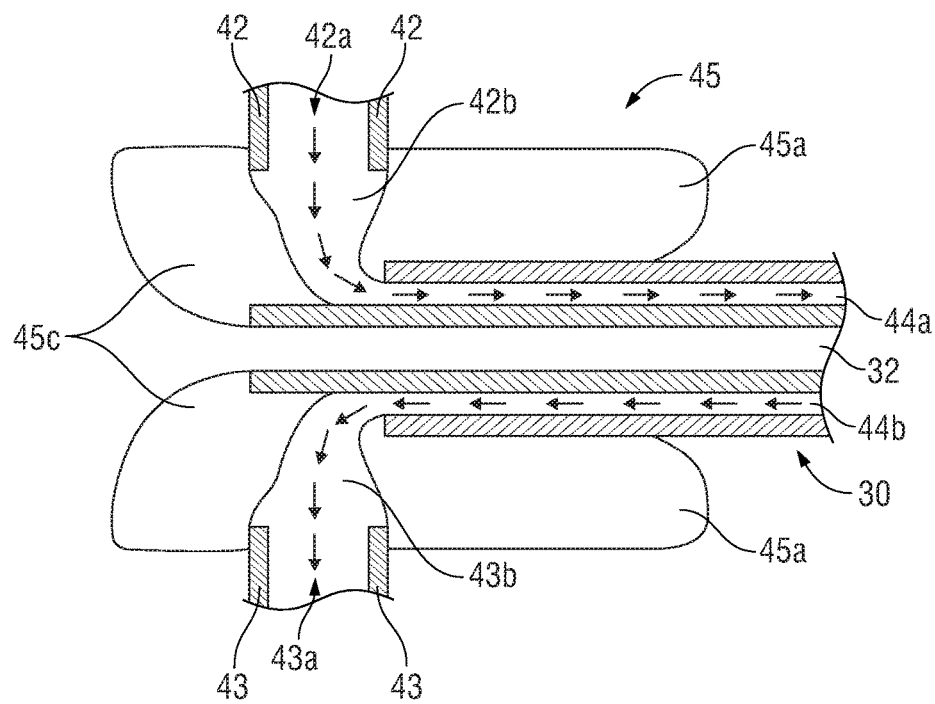
Figure 8C:
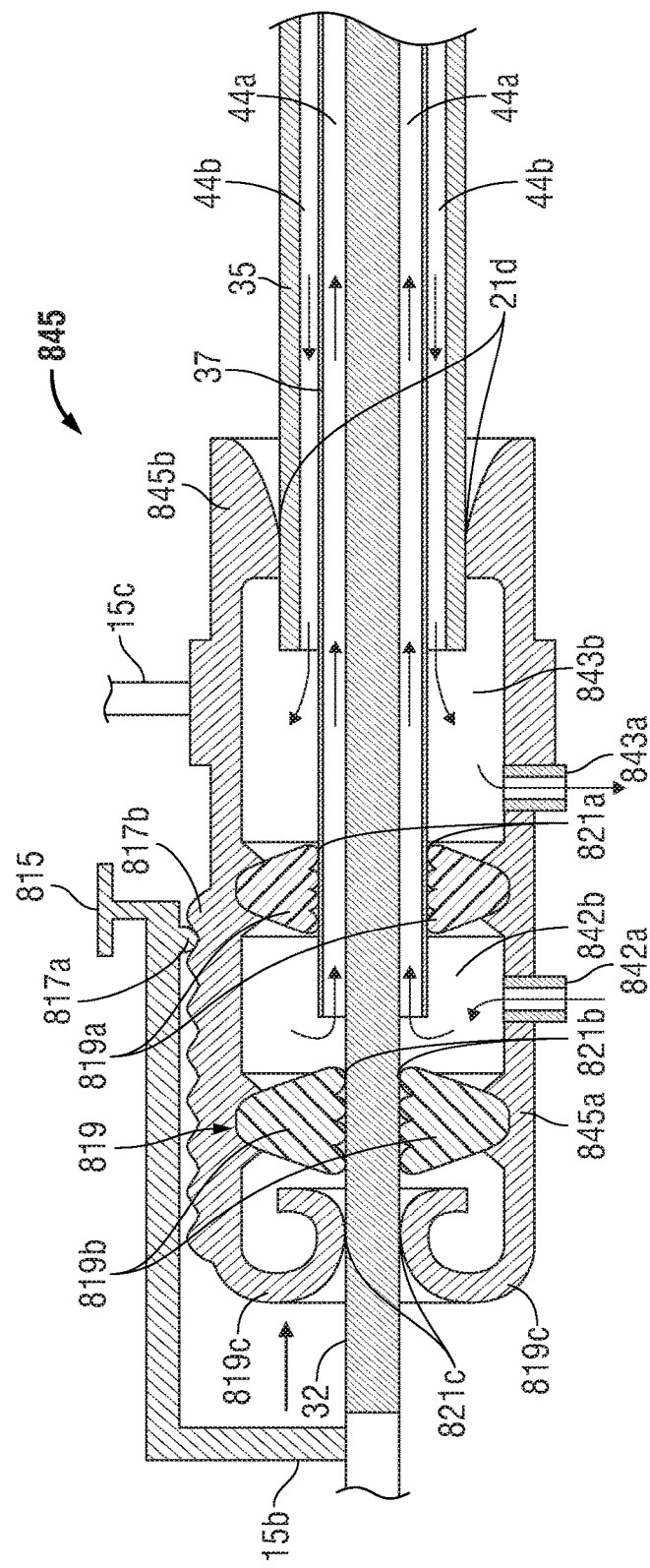

The catheter hub 18 includes a coupler 45 or an adjustable fluid coupler 845 as illustrated in FIGS. 8A-8B and FIG. 8C, respectively. Coupler 45 and adjustable fluid coupler 845 provide connections to the one or more lumens 30a-30c, 44a and 44b formed in the flexible microwave catheter 30 FIG. 8A illustrates a cross-section of a coupler 45 that provides connections to a flexible coaxial cable lumen 30a, a guide wire tracking lumen 30b and a sensor lead lumen 30c. FIG. 8B illustrates a cross-section of a coupler 45 that provides connections to a flexible coaxial cable lumen 30a and inflow and outflow fluid passageways 44a, 44b. FIG. 8C illustrates an adjustable coupler 845 that provides adjustable connections to a flexible coaxial cable lumen 30a and inflow and outflow fluid passageways 44a, 44b. Catheter hub 18 and coupler 45 and adjustable coupler 845 may include any number and combinations of lumens, pathways and electrical conduits required to facilitate the various connections to the flexible microwave catheter 30.

In FIG. 8A, a guide wire 47 is introduced into the guide wire tracking lumen 30b through an opening (not shown) formed between the coupler body 45a and the proximal stain relief 45c and one or more sensor leads 34a are introduced into the sensor lead lumen 30c through another opening formed between the coupler body 45a and the proximal strain relief 45c.

In FIG. 8B, an inflow conduit 42 connects to inflow port 42a and provides cooling fluid to inflow plenum 42b. Cooling fluid in inflow plenum 42b flows distally through the inflow fluid passageway 44a providing cooling to the distal end of the flexible microwave catheter 30. Inflow fluid passageway 44a is in fluid communication with outflow fluid passageway 44b of the distal end of the flexible microwave catheter 30 (see FIGS. 15A-15B) such that cooling fluid travels proximally through the outflow fluid passageway 44b to the outflow plenum 43b of the outflow port 43a. Outflow conduit 43 connects the outflow port 43a and returns cooling fluid to fluid cooling system 40. Inflow port 43a and outflow port 43a are formed in the coupler 45 between the coupler body 45a and the proximal strain relief 45c although connections to any one or more of the lumens of the flexible microwave catheter 30 (e.g. flexible coaxial cable lumen 30a, guide wire tracking lumen 30b, sensor lead lumen 30c, inflow fluid passageway 44a and outflow fluid passageway 44b) may be formed in any portion of the coupler 45.

In some embodiments, catheter hub 18 includes an adjustable fluid coupler 845, as illustrated in FIG. 8C. Adjustable fluid coupler 845 includes a fluid coupler body 845a forming an inflow plenum 842b and an outflow plenum 843b within the fluid coupler body 845a. The inflow plenum 842b is in fluid communication with the inflow conduit 842 and the outflow plenum 843b in fluid communication with the outflow conduit 843.

Adjustable fluid coupler 845 may also include a distal and/or proximal strain relief (not explicitly shown) that supports the flexible microwave catheter 30 (e.g., the assemblage and connections to the flexible coaxial cable 32) and the transmission line 14. Additional strain reliefs may be provided to support the inflow conduit 41a, the outflow conduit 41b and other elements that connect to the coupler 45 and adjustable fluid coupler 845 described herein.

Adjustable fluid coupler 845 is configured to adjustably couple a coaxial cable (e.g., transmission line 14 or the coaxial flexible cable 32), the fluid cooling system 30 and the outer sheath 35 of the flexible microwave catheter 30. Fluid coupler body 845a houses a fluid sealing system 819 and forms an outer sheath coupler 845b on the distal end. Fluid sealing system 819 includes a distal sealing diaphragm 819a, a proximal sealing diaphragm 819b and a bypass bulb 819c on the proximal end of the fluid coupler body 845a. The distal sealing diaphragm 819a and proximal sealing diaphragm 819b may each include one or more o-rings.

When discussing deployment herein, two approaches may be utilized. In the first approach, the distal end of the flexible microwave catheter 30 is placed proximal the targeted tissue and the radiating portion 100 is eased out distally from the outer sheath 35 of the flexible microwave catheter 30 (see at least FIGS. 42-44). In a second approach, the distal end of the flexible microwave catheter 30 is placed adjacent the targeted tissue and the outer sheath 35 is pulled back proximally thereby deploying the radiating portion 100 (see at least FIGS. 18B-18G).

The distal sealing diaphragm 819a is disposed between a fluid flow lumen 37 and the interior surface of the fluid coupler body 845a thereby forming an outflow plenum 843b between the distal inner surface of the fluid coupler body 845a, the outer surface of the fluid flow lumen 37, the distal sealing diaphragm 819a and the outer sheath coupler 845b. The outflow plenum 843b receives fluid circulated through the flexible microwave catheter 30 and provides the circulated fluid to the outflow port 843a.

Proximal sealing diaphragm 819b is disposed between the fluid coupler body 845a and the flexible coaxial cable 32 thereby forming an inflow plenum 842b between the inner surface of the fluid coupler body 845a, the outer surface of the flexible coaxial cable 832, the distal sealing diaphragm 819a and the proximal sealing diaphragm 819b. The inflow plenum 842b receives cooling fluid from the inflow port 842a. The cooling fluid provided to the inflow plenum 842b from the inflow port 842a flows through the flexible microwave catheter 30 in an inflow fluid passageway 44a formed between the outer surface of the flexible coaxial cable 32 and the inner surface of the fluid flow lumen 37.

Bypass bulb 819c provides a secondary seal between the fluid coupler body 845a and the flexible coaxial cable 32. Bypass bulb 819c is configured to catch fluid which may pass through the proximal sealing diaphragm 819b. Bypass bulb 819c may also provide strain relief to the flexible coaxial cable 32 that extends into and through the fluid coupler body 845a.

During use, coolant flows through the inflow port 842a and into the inflow plenum 842b. Fluid pressure in the inflow plenum 842b forces the coolant into the inflow fluid passageway 844a formed between the outer surface of the flexible coaxial cable 32 and the inner surface of the fluid flow lumen 37. Coolant continues to the distal end of the flexible microwave catheter 30, through the assembly (e.g., radiating portion 100) on the distal end thereof, and into an outflow fluid passageway 44b. The outflow fluid passageway 44b is formed between the outer surface of the fluid flow lumen 37 and the inner surface of the outer sheath 35. Fluid from the outflow fluid passageway 44b is deposited in the outflow plenum 843a, flows through the outflow port 843a and to a coolant destination (e.g., storage container for re-use and/or drainage system).

The fluid flow lumen 37 is positioned coaxially around the flexible coaxial cable 32, and the outer sheath 35 is positioned coaxially around the fluid flow lumen 37. A clearance between the outer diameter of the flexible coaxial cable 32 and inner diameter of the fluid flow lumen 37 defines a first fluid conduit (e.g., inflow fluid passageway 44a). A clearance between the outer diameter of the fluid flow lumen 37 and an inner diameter of the outer sheath 35 defines a second fluid conduit (e.g., outflow fluid passageway 44b). During use, a coolant, e.g., carbon dioxide, air, saline, water, or other coolant media, may include a desirable dielectric property and may be supplied to the flexible microwave catheter 30 and/or radiation portion 100 on the distal end thereof by one coolant conduit, and evacuated from the flexible microwave catheter 30 by the other coolant conduit. That is, in some embodiments, the first fluid conduit (e.g., inflow fluid passageway 44a) supplies coolant and the second fluid conduit (e.g., outflow fluid passageway 44b) evacuates coolant. In other embodiments, the direction of fluid flow may be opposite. One or more longitudinally-oriented fins or struts (not explicitly shown) may be positioned within the inflow fluid passageway 44a, the outflow fluid passageway 44b and/or the outer sheath 35 to achieve and maintain coaxial centering among the outer sheath 35, fluid flow lumen 37, and/or the flexible coaxial cable 32.

In some embodiments, actuator arm 15b provides a linkage between the flexible coaxial cable 32 and the actuator 15. Actuator 15 and actuator arm 15b are configured to impart movement of the flexible coaxial cable 32 through the adjustable fluid coupler 845. Movement of the flexible coaxial cable 32 deploys the radiating portion 100 as discussed in detail hereinbelow. During movement of the flexible coaxial cable 32, a fluid-tight seal is maintained about the flexible coaxial cable by the proximal sealing diaphragm 819b.

In some embodiments, coupler actuator arm 15c provides a linkage between the adjustable fluid coupler 845 and the actuator 15. Actuator 15 and coupler actuator arm 15c are configured to impart movement to the adjustable fluid coupler 845, which, in turn, imparts movement to the inflow lumen 837 and outer sheath 35 about the flexible coaxial cable 32 which is fixed in position within the hub 18. As such, in some embodiments, the flexible coaxial cable 32 is moved longitudinally through the stationary adjustable fluid coupler 845, thereby deploying a distally-positioned radiating portion 100. In some embodiments, the flexible coaxial cable 32 is stationary and the adjustable fluid coupler 845, outer sheath 35 and fluid flow lumen 37 are moved longitudinally about the flexible coaxial cable 32 thereby retracting the outer sheath 35 from the distally positioned radiation portion 100.

In use, the flexible microwave catheter 30 is fed through a lumen to a target tissue adjacent a natural body lumen and/or body structure. In certain instances, the vascular system presents a serpentine route through the body to various natural body lumens and/or body structures. For example, the femoral artery provides access to the renal artery. The various elements that form the flexible microwave catheter 30 may be subject to shifting and/or displacement forces arising from the differing radii of the flexible microwave catheter 30 elements, which can cause undesirable effects such as kinking, twisting, etc. Advantageously, the various components that form the flexible microwave catheter 30 and the connections to the fluid sealing system 819 are formed from material having resilient and lubricious qualities, that enables the elements to move independently longitudinally (e.g., proximally and/or distally) within the fluid coupler body 845a and/or the catheter hub 18. In this manner, the elements can shift in position as the flexible microwave catheter 30 is guided into place while the fluidic integrity of the cooling elements are maintained.

The disclosed flexible microwave catheter 30 may be percutaneously introduced into the femoral artery and positioned within the renal artery adjacent to the renal nerve bundle. Placement of the flexible microwave catheter 30 may be intravascularly introduced and positioned adjacent to any desired target tissue. The configurable length microwave energy radiating device 100 includes a radiating portion that cooperates advantageously with the renal artery physiology to deliver denervation energy to the renal nerve bundle while minimizing collateral damage to the arterial vessel and related anatomical structures.

A catheter system in accordance with the present disclosure may include a guidewire having a knob or ball disposed at a distal end thereof. The knob or ball may be radiopaque to enable positioning of the guidewire, and more particularly, the distal end thereof, using imaging (fluoroscopy, MRI, etc.). During use, a distal end of the guidewire may be introduced into a body lumen and advanced into position, optionally using imaging as described above. A proximal end of the guidewire may then be inserted into a corresponding port on the catheter that is in communication with the guidewire lumen. The catheter is then advanced into the body lumen to the desired location. As the catheter is advanced to the desired location, an indentation or other feature of the knob, ball, and/or catheter provides tactile feedback and/or a positive stop to facilitate correct positioning of the catheter.

In some embodiments, the distal end of the guide wire tracking lumen 30b terminates proximal from the radiating portion 100, as illustrated in FIGS. 9A-9C. Distal end 30bd of guide wire tracking lumen 30b forms a guide wire ball receiver 47b in the outer sheath 35 of the flexible microwave catheter 30. Guide wire ball receiver 47b is configured to receive the proximal end of guide wire 47 as illustrated in FIG. 9A.

In use, guide wire 47 and distal guide wire ball 47a are inserted into the body, and distal guide wire ball 47a is positioned adjacent to targeted tissue using a guidance system (e.g., imaging system or any suitable guidance and positioning system). After positioning the distal guide wire ball 47a at a desired location, the proximal end (not explicitly shown) of the guide wire 47 is inserted into the guide wire ball receiver 47b, passed through the guide wire tracking lumen 30b and through the catheter hub 18 (see FIGS. 2, 6A, and 7B).

Flexible microwave catheter 30 is guided to the target tissue via the guide wire 47. As illustrated in FIGS. 9B and 9C, distal guide wire ball 47a is received by the guide wire ball receiver 47b such that the guide wire ball 47a is proximal to the radiating portion 100.

Some embodiments and structures discussed herein follow the coaxial structure analogy described hereinabove and illustrated in FIGS. 4A-4C and 5 wherein the coaxial structure incorporates one or more layers of a natural body lumen to form a coaxial feedline structure. Like any other coaxial structure, the coaxial-positioning of structures that form the waveguide are directly related to the operation and/or efficiency of the waveguide.

FIGS. 10A-12A each illustrate a flexible microwave catheter 30 positioned in a renal artery RA and FIGS. 10B-12B illustrate the respective cross-section thereof. In FIGS. 10A and 10B, the flexible microwave catheter 30 and distal radiating portion 100 are centered in the renal artery RA. In FIGS. 11A and 11B, the flexible microwave catheter 30 and distal radiating portion 100 are offset from dead center by 0.5 mm and in FIGS. 12A and 12B, the flexible microwave catheter 30 and distal radiating portion 100 are offset from dead center by 1 mm. Each of FIGS. 10A-12A and 10B-12B illustrate a distribution of thermal energy in and around the renal artery from the application of 25 W of microwave energy to the flexible microwave catheter 30 for about 2 minutes.

In each of FIGS. 10A-12A, the flexible microwave catheter 30 includes a first proximal waveguide, formed by the flexible coaxial cable 32, and a second distal waveguide, formed by the inner conductor 20 and a portion of the anatomical structure. The flexible coaxial cable 32 that forms the first proximal waveguide includes an inner conductor 20 centered and coaxially offset from an outer conductor 24 by a dielectric layer 22. The second distal waveguide is an anatomical resonant structure 1032, 1132, and 1232 that includes a portion of the inner conductor 1020, 1120, 1220, respectively, extending distally from the flexible coaxial cable 32, a portion of the renal artery RA coaxially offset from the inner conductor by a transitional dielectric 1026, 1126, 1226 and fluid 1 contained in the renal artery.

A radiating portion 100 of the flexible microwave catheter 30 is formed at a distal end of the flexible coaxial cable 32. In embodiments according to the present disclosure, and of a manufacturing process therefor, a portion of the outer conductor 24 is removed to expose the inner conductor 20 thereby forming a feed gap 1050, 1150, 1250 (e.g., feed point) that facilitates the propagation of denervation energy, such as microwave energy. Optionally or alternatively, a transitional dielectric 26 is disposed in the feed gap 1050, 1150, 1250. The transitional dielectric 1026, 1126, 1226 corresponds generally and/or geometrically to the portion of the outer conductor 24 removed therefrom.

The transitional dielectric 26 may have dielectric properties between that of the inner dielectric 22 and that of the expected or average dielectric properties of the targeted anatomical structures (e.g., the renal artery RA, body lumen and/or other body structure). Use of a transitional dielectric 26 in this manner may improve coupling between the radiating portion 100 and the targeted tissue, by, e.g., reducing reflections, reducing standing waves (e.g., VSWR), and by providing impedance matching between the radiating portion 100 and targeted tissue.

In FIGS. 10A and 10B, the inner conductor 20 is coaxially centered in the renal artery RA. As such, the anatomical resonant structure 1032 is substantially coaxial thereby generating a substantially balanced resonating structure. The balanced anatomical resonant structure 1032 generates heating, due to dielectric losses and/or conductive losses, in the anatomical portions of the renal artery structure (e.g., one or more layers of the renal artery as discussed hereinabove). As illustrated in FIG. 10B, centering of the inner conductor 20 within the renal artery RA generates substantially uniform heating 1000a about the renal artery RA.

Centering the inner conductor 1020 in the renal artery RA, in addition to forming a balanced anatomical resonant structure 1032, generates substantially uniform heating 1000a and even distribution of the generated thermal energy about the renal artery RA. Additionally, heating of the distal end of the flexible coaxial cable 32 and heating of the exposed inner conductor 1020 in the anatomical resonant structure 1032 are maintained to acceptable temperatures.

As illustrated in FIGS. 11A-12A, offsetting the inner conductor 20, as illustrated in FIGS. 11A-12A and 11B-12B, with respect to the anatomical structure (e.g., the renal artery RA) that forms the anatomical resonant structure 1132 and 1232 results in the generation of non-uniform heating 1100a, 1200a about the renal artery RA.

In FIGS. 11A and 11B, the inner conductor 20 is offset from the center of the renal artery RA by 0.5 mm and in FIGS. 12A and 12B the inner conductor 20 is offset from the center of the renal artery RA by 1 mm, in each instance an unbalanced anatomical resonant structure 1132 and 1232 is formed. The unbalanced anatomical resonant structure 1132, 1232 generates non-uniformed heating 1100a, 1200a about the renal artery RA forming a hot-spot adjacent the renal artery RA. The hot-spot may result in raising the temperatures of the portion of the renal artery RA adjacent the hot spot and may result in irreversible tissue damage. Additionally, offsetting the inner conductor 20 may also heat the distal end of the flexible coaxial cable 32 and/or a portion of the exposed inner conductor 20 to unacceptable temperatures.

Figure 13:
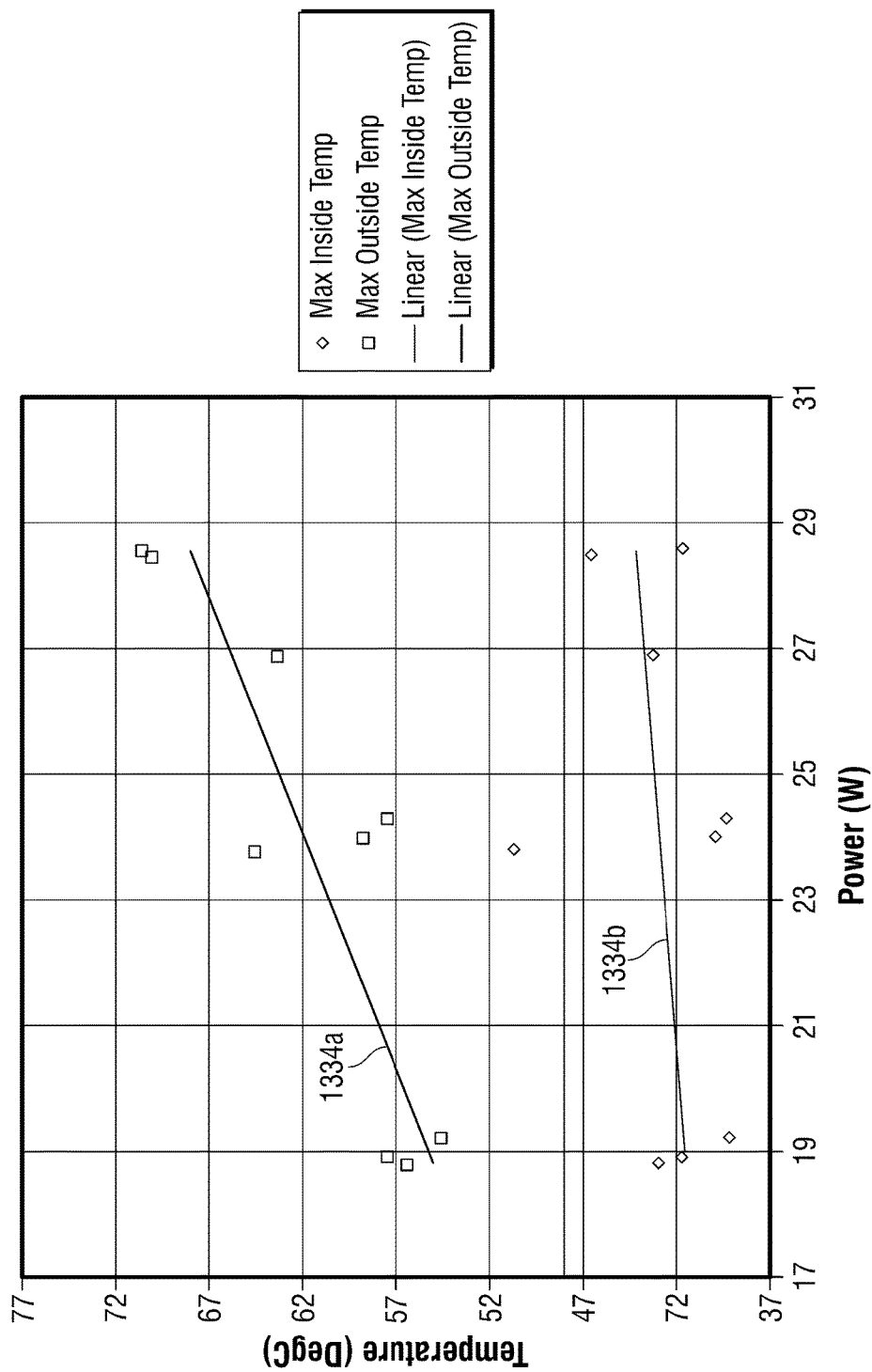
FIG. 13 illustrates a relationship between temperatures measured inside and outside the renal artery and power measured during an experimental procedure.

As illustrated in FIGS. 10A-12A, each anatomical resonant structure 1032, 1132, 1232 generates a large delta between the inside temperature and the outside temperature of the renal artery RA. FIG. 13 illustrates experimental data showing the temperature inside and outside of the renal artery RA plotted against the power measured at the beginning of the flexible coaxial cable 32 (see FIG. 7). The linear representation of the maximum temperature inside the renal artery 1334a and the linear representation of the maximum temperature outside the renal artery 1334b demonstrates that the anatomical resonant structures 1032, 1132, 1232 generate temperatures outside of the renal artery RA that will achieve a cytotoxic temperature (e.g., a quality of thermal energy toxic to cells) in the outer layers of the vessel while maintaining less than lethal temperatures inside the renal artery RA.

As discussed hereinbelow, the flexible microwave catheter 20 may include a centering device configured to coaxially center the radiating portion 100 in a natural body lumen or in a natural body structure thereby forming a balanced anatomical resonant structure as discussed hereinabove. Centering device described herein includes stent-like expandable members (see FIGS. 16A-16C, 17A-17B, 18A, 19A, 20, 21 and 22A-22B), balloon-like inflatable members (see FIGS. 24, 25a-25B, 26A-26C and 58A-58D), compressible expandable members (see FIGS. 27A-35), repositionable expandable members (see FIG. 18A), a centering device with a plurality of members (see FIGS. 32A-32B, 35, 37A-37B, 39A-39B, 40A-41B), two or more fin expandable members (see FIGS. 27A-27D and 28), expandable basket members (see FIGS. 29-35), clover leaf expandable members (see FIG. 34-35), expandable single and double paddle members (see FIGS. 36A-39B), expandable single and double propeller members (see FIGS. 36A-39B), expandable tines (see FIGS. 40A-40B), expandable fin members and expandable helical fin members (see FIGS. 41A-41B), and any combination thereof.

The centering structures described herein provide minimal resistance to blood flow along the structure, which enables the flowing blood to cool the structure and tissues not targeted for ablation.

In some embodiments, the centering device (or devices) are restrained in an outer sheath and self-deploy (e.g., expand), and thereby center the radiation portion 100, when released from the outer sheath. Similarly, the centering device self-retracts when retracted into the outer sheath.

Centering structures described herein may be formed from conductive materials, non-conductive materials, dielectric materials or any combination thereof. In some embodiments, a conductive centering structure includes a shaped memory material such as, for example, a nickel-titanium alloy (e.g., nitinol), or a ferromagnetic shape-memory alloy.

In some embodiments, a non-conductive centering structure includes a shaped-memory polymer. The shaped-memory polymer may be triggered to expand to a shape-memory position by an electromagnetic field generated by the delivery of microwave energy. As such, the centering device centers the radiating portion 100 within the body lumen while the radiating portion 100 delivers microwave energy.

In some embodiments, the centering device may be used to anchor the radiating portion of the flexible medical catheter into tissue or adjacent targeted tissue. Alternatively, the centering device may be self-centering via fluid/hydrodynamic, and/or mechanical forces within the body lumen BL.

In some embodiments, centering devices may also be configured to dielectrically buffer the microwave currents from the surrounding physiology.

Embodiments and features described herein may be selected and combined with other embodiments and features described herein in any combination. For example, radiating portion may be selected from a radiating portion with a monopole antenna (see FIG. 5), one or more slotted feed gaps (see FIGS. 10A-12A, 14F, 16A-C, 19A-F, 20-22B, 50-53, 55 and 57), a dipole antenna (see FIG. 17A), a radiating portion with a helical fed gap (see FIGS. 42-45, 47, 54, 56 and 57), or any combination thereof. The selected radiating portion may be combined with a fluid cooled flexible microwave catheter that connects and combined with a catheter with a fluid coupler or a adjustable fluid coupler for deploying the radiating portion from the outer sheath of the flexible microwave catheter. Further, any of the above named combinations may include a centering device or structure. The centering device or structure may connect to the catheter hub that facilitates the actuation and/or deployment of the centering device.

Centering devices may provide additional functionality in addition to positioning the device. For example, in some embodiments the centering device may form a choke or balun that defines and/or limits the derivation region and/or defines and/or limits the anatomical resonant structure. In some embodiments, the centering device may include one or more structures wherein the structure(s) defines a pattern of applied denervation energy.

Figure 14A:
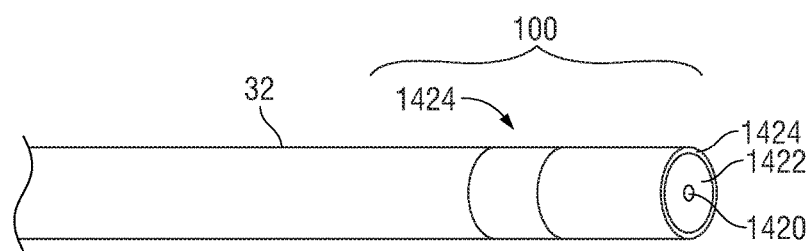
FIGS. 14A-14F illustrates steps of a manufacturing process for assembling some of the embodiments of the present disclosure.

One embodiment of a radiating portion 100 according to the present disclosure, and of a manufacturing process therefor, is illustrated in FIGS. 14A-14E. In the first step of the manufacturing process, a flexible coaxial cable 32 is provided as illustrated in FIG. 14A. A cylindrical or semi-cylindrical portion of the outer conductor 1424 and dielectric 1422 is removed to expose the inner conductor thereby forming a feed gap 1450 (e.g., feedpoint). Feed gap 1450 facilitates the propagation of denervation energy, such as microwave energy.

The portion of the outer conductor 1424 may be removed by etching, cutting, or stripping the outer conductor off the cable in a ring with length of approximately 0.01" leaving approximately ¼ wavelength of coaxial cable distal to this location.

Figure 14B:
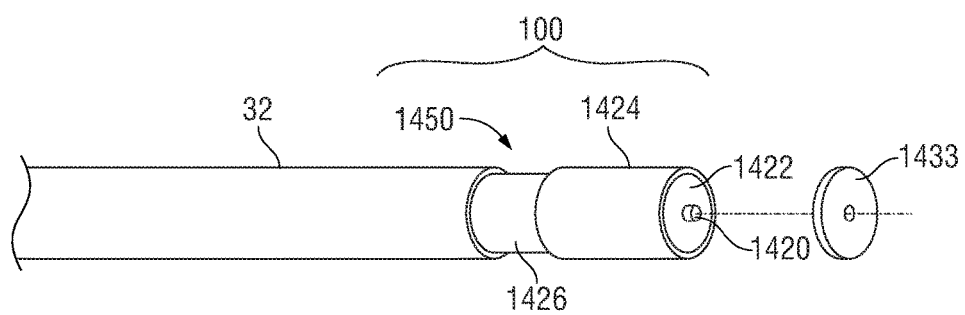

Optionally, a transitional dielectric 1426 may be disposed in the feed gap 1450, corresponding generally to the cylindrical section of the outer conductor 1424 that is removed, as illustrated in FIG. 14B. The transitional dielectric 1426 has dielectric properties between that of the inner dielectric 1422, and that of the expected or average dielectric properties of the anatomical structures with which the antenna is to be used, e.g., the renal artery and/or blood in the renal artery. Transitional dialectic 1426 may be a formed from any suitable dielectric material and/or dielectric fluid. Use of a transitional dielectric 1426 in this manner may improve coupling between the radiating portion 100 and targeted tissue, by, e.g., reducing reflections, reducing standing waves (e.g., VSWR), and by providing impedance matching between the radiating portion 100 and tissue.

Figure 14C:
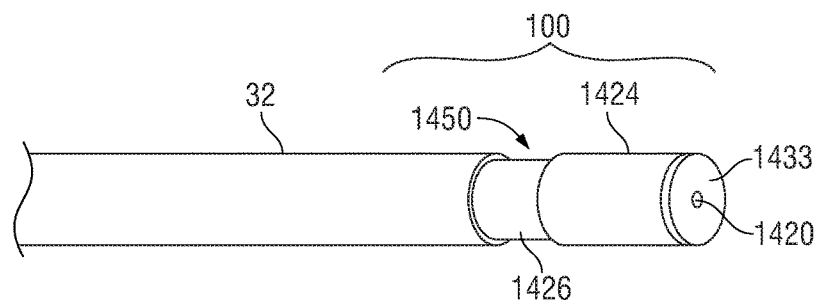

As further illustrated in FIG. 14B, a distal-most end of the flexible coaxial cable 32, a portion of the outer conductor 1424 and inner dielectric 1422 are removed thus exposing a portion of the inner conductor 1420. As illustrated in FIG. 14C, a short conductive (e.g., metallic) cylinder, disc, or cap 1433 having an opening defined at the center thereof, the opening being dimensioned to accept the inner conductor 1420, is joined at the opening to the exposed end of the inner conductor 1420 and at the perimeter thereof to the outer conductor 1424. This distal "cap" 1433 shorts the inner conductor 1420 to the outer conductor 1424, which, in turn, may optimize, control, focus, and/or direct the general distal radiating pattern of the radiating portion 100, e.g., reduce, focus, shape and/or enhance the propagation of denervation energy beyond the distal end of the radiating portion 100.

In some embodiments, cap 1433 is formed from a high-temperature dielectric such as a plastic, ceramic, or other suitable dielectric material. Cap 1433 may include a high-temperature dielectric and a conductive portion formed therein that provides a short or low impedance path between the inner conductor 1420 and the outer conductor 1424. In some embodiments, the distal portion of the cap 1433 is formed from a non-conducting material, such as, for example, a polymer.

Figure 14D:
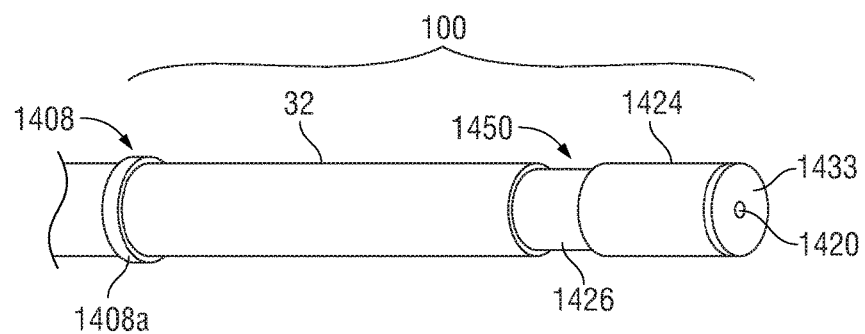
Figure 14E:
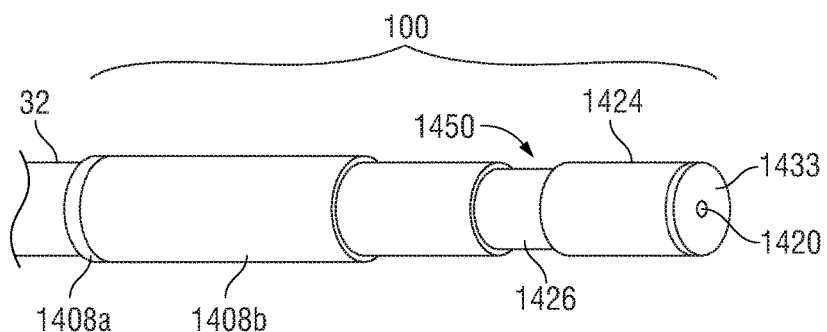
Figure 14F:
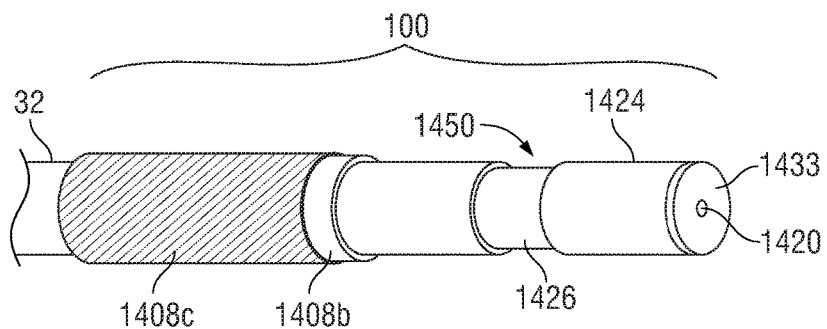

In some embodiments, a choke or balun 1408 short may be fixed to the outer conductor 1424 at a position proximal of the feed gap 1450, as illustrated in FIG. 14D. The balun 1408 may include a short conductive ("metallic") ring 1408a having an inner diameter dimensioned to accept the outer conductor 1424. The balun ring 1408a is electrically bonded (e.g., soldered, welded, and/or mechanically connected) to the outer conductor 1424. The balun ring 1408a is positioned a distance from the feed gap 1450 of about 180 degrees in phase length. This balun ring 1408a affects a microwave short which, in turn, may optimize, control, focus, and/or direct the general radiating pattern of the radiating portion 100, e.g., reduce the propagation of denervation energy beyond the proximal end of the radiating portion 100 and/or the balun 1408. Balun ring 1408a may improve impedance matching, reduce reflections and/or standing waves, improve efficiency, and reduce the risk of embolism (e.g., clotting).

The balun 1408 may further include a balun dielectric sleeve 1408b, which may be formed from extruded polytetrafluoroethylene (PTFE, e.g., Teflon®), from extruded polyethylene terephthalate (PET) and/or from extruded fluorinated ethylene propylene (FEP). The balun dielectric sleeve 1408b may be positioned over the radiating portion 100 of the assembly and mated to the balun ring 1408a. The balun dielectric sleeve 1408b may further include a length of heat shrink tubing 1408c, having a conductive material on a surface thereof, preferably an inner surface, that may be positioned over the PTFE balun dielectric sleeve 1408c to change a dielectric property and/or to improve the performance of the balun 1408 and thus, improve the radiating pattern of denervation energy. A silver ink may be disposed on the inner surface of the heat shrink tubing 1408c, whereupon shrinking the heat shrink 1408c over the balun ring 1408*a* and balun dielectric 1408*b* forms a resonant microwave structure that improves the performance of the balun 1408 and, in turn, improves the radiating pattern of the denervation energy.

In some embodiments, the balun dielectric sleeve 1408*b* and metal ring 1408*a* are then covered from the proximal end to near the distal end with a heat shrink coated in conductive ink (e.g., a balun outer conductor). In some embodiments, the distal end of the balun dielectric sleeve 1408*b* is not coated with the conductive heat shrink, and thus forms a balun extended dielectric that improves balun performance.

Figure 15A:
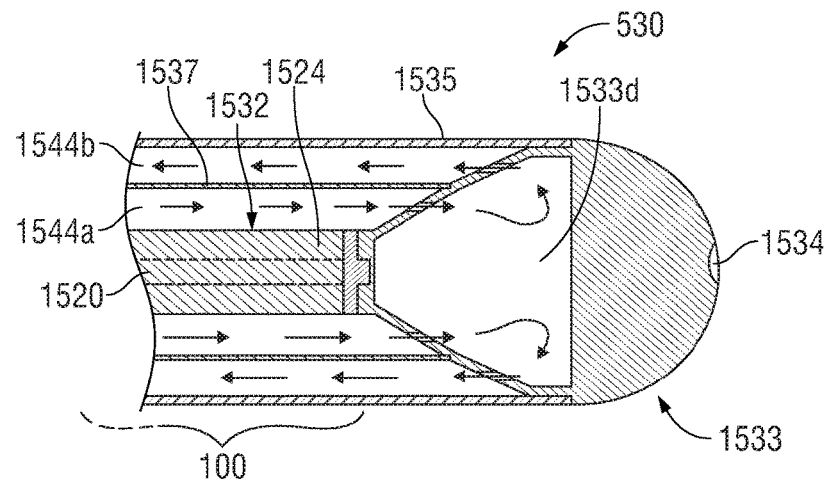
FIG. 15A is a longitudinal, cross-sectional view of an embodiment of a radiating portion cap in accordance with the present disclosure for returning circulating fluid from an inflow fluid passageway to an outflow fluid passageway.
Figure 15B:
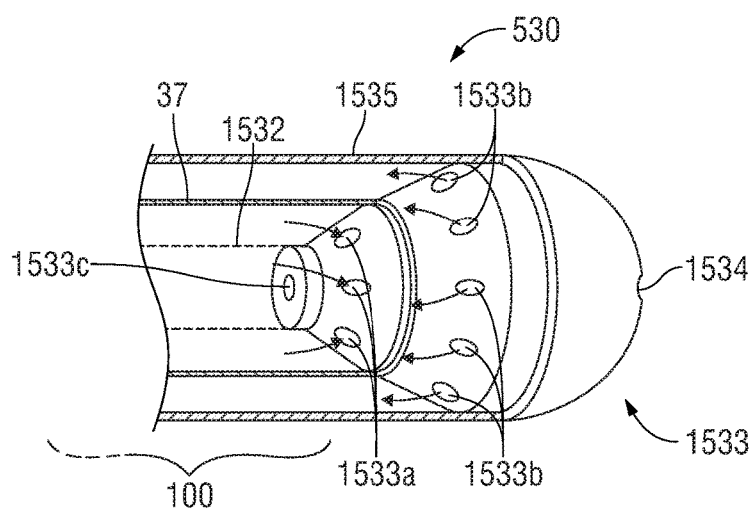
FIG. 15B is a perspective view with partial cross-section of the cap of FIG. 15A.

As illustrated in FIGS. 15A-15B, the cap 1533 connects to the distal end of the flexible coaxial cable 1532, the distal end of the fluid flow lumen 1537 and the distal end of the outer sheath 1535. A distal end of the fluid flow lumen 37 is sealably joined to the proximal face of the cap 1533 to achieve and maintain concentric alignment among the radiating portion 100 elements. One or more cap coolant passageways 1533*a*, 1533*b* formed within the cap 1533 enables coolant to circulate from the inflow fluid passageway 1544*a* to the outflow fluid passageway 1544*b*, which facilitates the flow of coolant through the radiating portion 100, and may advantageously provide cooling of the radiating portion 100 and cap 1533.

Cap 1533 may receive the inner conductor 1520 via the proximal inner conductor receiver 1533*c* and connect to the outer conductor 1524 thereby providing a short or low resistance connection between the inner conductor 1520 and the outer conductor 1524.

Cap 1533 connects to outer sheath 1535 and forms a fluid-tight seal therebetween. Cap 1533 may be bonded to the outer sheath 1535 by welding, bonding, adhesive, or any other suitable manner of connection. Cooling fluid enters cap fluid chamber 1533*d* through cap inflow coolant passageways 1533*a* and flows out of the cap fluid chamber 1533*d* through cap outflow coolant passageways 1533*b*.

A temperature sensor 1534 may be operatively associated with the radiating portion 100 and/or cap 1533 in accordance with the present disclosure. For example, and without limitation, one or more thermoprobes, pressure sensors, flow sensors, or any other suitable sensor may be included within the radiating portion 100, cap 1533, outer sheath 1535, the flexible coaxial cable 1532, the inflow and/or outflow fluid passageway 1544*a*, 1544*b*, a cap fluid chamber 1533*d* or any other conduit and/or structure (e.g., a mesh, balloon, expandable and/or deployable member,) described herein. In some embodiments, temperature sensor 1534 may be positioned on the distal end of the cap 1533. One or more thermoprobes may be included within the flexible microwave catheter 1530 (e.g., outer sheath, flexible coaxial cable 32, one or more fluid chambers or conduits, outer dielectric insulating layer 128, shielding outer conductor 124*a*, and/or any other structure described herein).

Temperature sensor 1534 may be positioned distal to the active heating zone of the radiating portion 100. The microwave energy delivery system 12 thereby monitors the temperature of the fluid passing through the hottest location. If the temperature sensor 1534 measures a temperature above a clotting temperature threshold, the system 12 may temporarily or permanently halt power delivery. In some embodiments, one or more temperature sensors 1534 may be positioned at the discharge of a fluid passageway formed in, thorough, or around a centering device as discussed hereinbelow.

In some embodiments, cap 1533 or any portion of the distal tip of the flexible microwave catheter 30 may include a radiopaque material (such as barium) to enhance the visibility thereof during fluoroscopy.

As discussed hereinabove with respect to FIGS. 6A and 8A-8C, a catheter hub 18 at a proximal end of the flexible microwave catheter 30 enables the operable coupling of a source of denervating energy (e.g., a microwave generator 22) to the flexible coaxial cable 32, a fluid cooling system 19 to the inflow fluid passageway 44*a*, and a receiving destination (e.g., a receptacle, reservoir, or drain) for coolant evacuated from the outflow fluid passageway 44*b*.

Figure 16A:
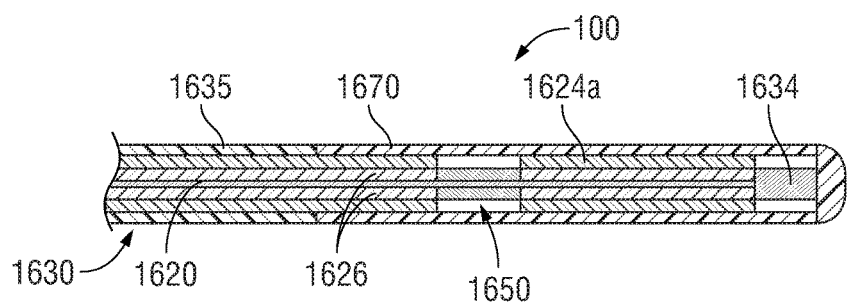
FIGS. 16A-16B are longitudinal, cross-sectional views of embodiments of stent-like expandable elements associated with a radiating portion in accordance with some embodiments of the present disclosure.
Figure 16B:
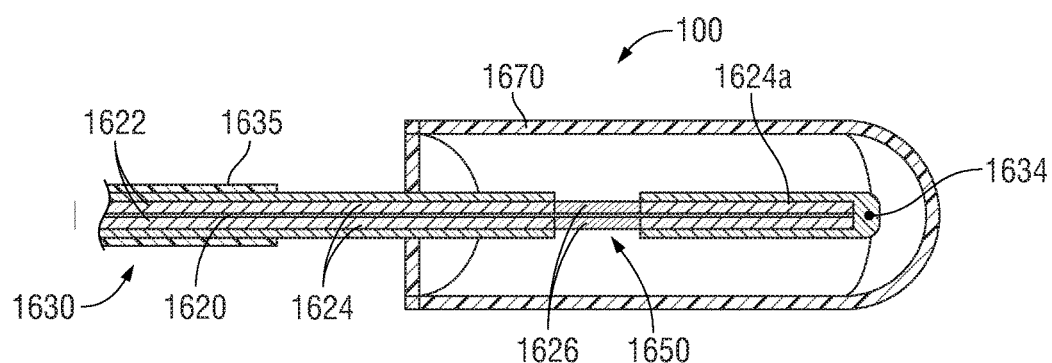
Figure 16C:
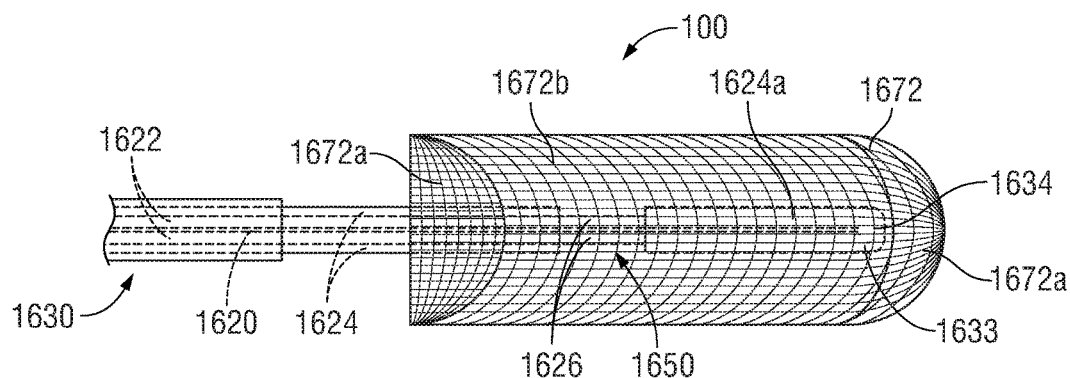
FIG. 16C is a side view of an embodiment of a stent-like expandable element associated with a radiating portion in accordance with some embodiments of the present disclosure.

As illustrated in FIGS. 16A-16C, a flexible microwave catheter 1630 in accordance with the present disclosure may include one or more stent-like expandable elements 1670 associated with the radiating portion 100. As illustrated in FIG. 16A, the stent-like expandable elements may be maintained in a compressed state while guiding the flexible microwave catheter 1630 through the vascular system to a position adjacent the target tissue. In some embodiment, the stent-like expandable element 1670 is maintained in a compressed state by the distal portion of the outer sheath 1635. In other embodiments, the stent-like expandable element 1670 is stowed in a compressed state within the outer sheath 1635.

During use, and as illustrated in FIG. 16B, the outer sheath 1635 may be retracted proximally and/or the stent-like expandable element 1670 may be advanced distally, causing the stent-like expandable element 1670 to extend from the confines of the outer sheath 1635 and to expand into a generally tubular, cylindrical and/or balloon-like shape around the radiating portion 100 thereby centering the radiating portion 100 of the flexible microwave catheter 1630 within the lumen (not specifically shown). The stent-like expandable element 1670 may be positioned such that the center of the stent-like expandable element 1670 is generally coincident with a feedpoint (e.g., feed gap 1650) of the radiating portion 100. Feed gap 1650, as illustrated in FIGS. 16A-16C, may include an exposed slotted portion of the inner conductor 1620 wherein a portion of the outer conductor 1624 has been removed. An exposed portion of the inner conductor 1620 may also include a transitional dielectric 1650 that covers the inner conductor 1620.

At least a portion of the stent-like expandable element 1670 may be positioned distal to the radiating portion 100, positioned proximally to the radiating portion 100, may generally surround the radiating portion 100, or any combination thereof. The stent-like expandable element 1670 may be formed from, e.g., wire mesh, wire members, stamped metal, and/or may be formed from any suitable electrically conductive material, including without limitation, stainless steel, copper, silver, platinum, gold, shape memory allow (e.g., Nitinol) and the like. In some embodiments, stent-like expandable element 1670 may also be formed from, and/or may include, a polymer or composite material with low electrical conductive such as a polyurethane, polyimide, FEP, PET, and/or PTFE.

FIG. 16C illustrates a stent-like expandable mesh element 1672. In some embodiments, the stent-like expandable mesh element 1672 includes a distal and a proximal end-cap mesh 1672*a* joined by a tubular body mesh 1672*b*. At least a portion of the tubular body mesh 1672*b* extends radially outward from the radiating portion 100 including the feed gap 1650 (e.g., inner conductor 1620 and transitional dielectric 1650).

In some embodiments, at least a portion of the endcap mesh 1672*a* includes a variable mesh density wherein the mesh density is greater at the distal and/or proximal ends, and less dense along the length of the tubular body mesh 1672b. The mesh structures described herein provide minimal impedance to blood flow distally along the structure, which enables the flowing blood to cool structures and tissues not targeted for ablation (blood, intima, and media of renal artery).

In some embodiments, the stent-like expandable element 1670 may be left in place within the renal artery RA as a stent to reduce complications from a potential stenosis. The stent-like expandable element 1670 may detach from the flexible microwave catheter 1630 after energy application and be left in place to mechanically support the renal artery RA.

In some embodiments, the stent-like expandable element 1670, or other expandable device described herein, may include three positions. In a first position, the stent-like expandable element 1670 is fully expanded/extended for initial placement. In a second position, the stent-like expandable element 1670 is retracted proximally to allow for deployment while maintaining the stent-like expandable element 1670 in place about the radiating section 100. In a third position, the stent-like expandable element 1670 is fully retracted such that the final proximal portion of the stent-like expandable element 1670 is released. The far distal portion of the stent-like expandable element 1670 may be released from the flexible microwave catheter 30 when the catheter 30 is pulled proximally out the renal artery RA. For example, it may fit into a slot which faces in the distal direction and therefore hold the mesh when the catheter is advanced distally, but releases only when the device is pulled proximally and the sheath is fully retracted.

In FIGS. 16A-16C, cap 1633 connects to the distal end of the radiating portion 100 and provides an electrical short between the inner conductor 1620 and outer conductor 1624, 1624a. Temperature sensor 1634 may be housed in the cap 1633 or housed in any other portion of the radiating portion 100, stent-like expandable element 1670, stent-like expandable mesh element 1672, flexible coaxial cable 1632 or outer sheath 1635.

In some embodiments, the proximal and/or distal portion of the stent-like expandable element 1670 and/or the proximal and/or distal portion of the stent-like expandable mesh element 1672a form a choke or balun short. The choke or balun short substantially confines the electromagnetic field to an electromagnetic boundary defined by the choke or balun short. As such, thermal heat generation is substantially limited to the portion radially outward from the feed gap.

In some embodiments, the centering structure forms a Faraday cage that is substantially opaque to microwave energy at the distal and proximal ends while remaining substantially transparent to microwave energy along at least a portion of the length thereof. Such an arrangement may have advantages, since it enables the device to target delivery of denervation energy radially (e.g., circumferentially to the renal artery) while reducing or eliminating the delivery of denervation energy axially (e.g., distally and proximally along the renal artery). A flexible medical catheter in accordance with the present disclosure may improve operative outcomes by enabling a surgeon to precisely deliver energy to targeted tissue while reducing or eliminating complications arising from collateral tissue effects.

The mesh forming the proximal portion and distal portions of the Faraday cage may form a choke or balun short that confines a substantial portion of the anatomical resonant structure to the anatomical structures between the proximal portion and distal portion of the Faraday cage.

In some embodiments, the mesh may be configured to accommodate specific wavelengths, or ranges of wavelengths, of denervation energy that may be utilized during denervation procedures. For example, and without limitation, to provide the desired microwave radiation pattern the mesh spacing (e.g., space between adjacent mesh elements) may be less than about $\frac{1}{10}\lambda$ (e.g., one-tenth the wavelength of the intended microwave signal) at the distal and proximal ends of the mesh structure to create an effective microwave boundary. Along the length of the mesh, the mesh spacing may be greater than about $\frac{1}{10}\lambda$ to avoid creating a microwave boundary thereby allowing for radiation of denervation energy.

Advantageously, the open mesh structure of the disclosed device enables blood to continue to flow along the surgical site during a denervation procedure, thereby increasing the time window available to the surgeon for completion of the procedure. Maintaining blood flow provides thermal management of the flexible microwave catheter 30 and the radiating portion 100, while providing cooling of the inner structure of the vessel walls.

Some embodiments according to the present disclosure include a radiating portion having a plurality of feed gaps. The radiating portion of a flexible microwave catheter in accordance with the present disclosure may include a mesh structure having a plurality of windows defined therein. Windows may include one or more materials with properties that are different than the body of the mesh structure. Alternatively, a window may be an open structure characterized by the absence of material (e.g., an aperture). As discussed herein, a window in a structure formed from a different material and a window in a structure characterized by the absence of material (e.g., an aperture) are used interchangeably. The material property may include a mechanical property, a material property, an electrical property, or any combination thereof. The window material properties may include a mechanical difference such as, for example, mesh spacing, mesh gauge, mesh formation, mesh thickness or any combination thereof. The window material property may include a physical difference such as, for example, material type, composition, material construction or any combination thereof. The window property may include an electrical difference such as, for example, conductivity, resistivity or any combination thereof.

The position of the windows may be distributed laterally along the mesh structure, and may be indexed radially and/or may be distributed radially. In some embodiments, three windowed slots are indexed radially 60° apart and distributed longitudinally along the mesh structure. The windows correspond to defined treatment zones (e g, kill zones) that enable a surgeon to select with precision the tissue regions targeted for denervation. A multi-window mesh structure, as describe herein, may also be utilized with a single feed gap design. A multi-window design may have advantages in that during denervation only a portion of the vessel wall is subjected to energy delivery, while still ensuring the renal nerve bundle is treated effectively.

Mesh structures may be configured to center the radiating portion 100 of the flexible microwave catheter 30 in a body lumen and/or a body structure.

Mesh structures may include conductive materials, non-conductive materials or a combination of conductive and non-conductive materials. Conductive mesh structures are configured to interact with the radiating portion of the flexible microwave catheter. For example, a conductive mesh structure may form part of a resonance structure. In some embodiments, the conductive mesh structure forms part of an anatomical resonant structure that includes at least a portion of the tissue surrounding the mesh structure.

At least a portion of a mesh structure may include a conductive portion configured to form a microwave choke or balun. For example, a distal and/or proximal portion of the mesh structure may include a conductive mesh structure configured to shunt the microwave energy signal thereby preventing at least a portion of the microwave energy signal from propagating proximally and/or distally of the conductive mesh structure.

In some embodiments, the stent-like expandable element 1670 is coupled to an actuator (e.g., actuator 15 and/or rotating actuator 15*g*). Actuator may be configured to mechanically expand the stent-like expandable element 1670 (or configured to expand, deploy or open a centering device described herein). Distal or proximal end-cap mesh 1672*a* may be coupled to actuator 15 and expanded and/or contracted by varying the position of the actuator 15.

Actuation of the centering device (e.g., stent-like expandable element or other centering device described herein) may vary the amount of force exerted to the inner surface of the body lumen thereby shaping the anatomy to a desirable structure and/or geometry. The body lumen may be shaped to form a particular shape, diameter and/or cylindrical structure to facilitate delivery of energy to the targeted tissue.

Figure 17A:
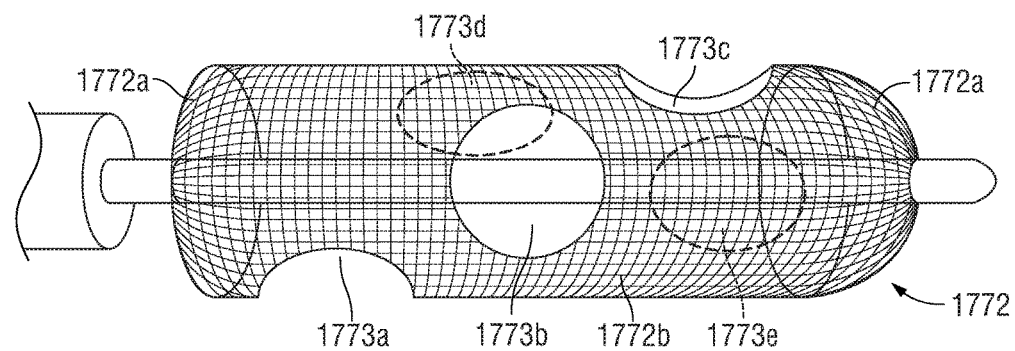
FIG. 17A is a perspective view of an embodiment of a conductive mesh structure that defines a plurality of windows for selectively delivering denervation energy to tissue in accordance with some embodiments of the present disclosure.
Figure 17B:
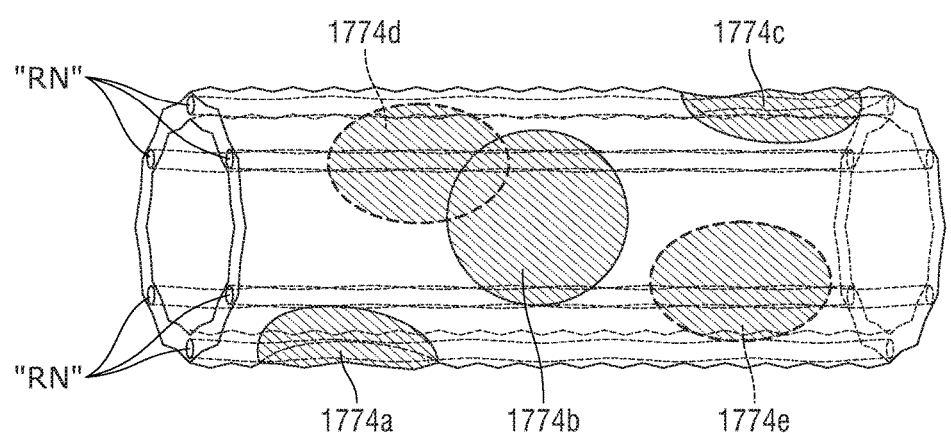
FIG. 17B is a perspective view of a portion of a renal artery after receiving the selectively delivered denervation energy from the conductive mesh structure of FIG. 17A.

As illustrated in FIGS. 17A-17B, the conductive mesh structure 1772 includes a plurality of windows 1773*a*-1773*e* defined in at least a portion of the lengthwise section. The conductive mesh structure 1772 is configured to enable the delivery of denervation energy to tissue through the windows 1773*a*-1773*e*, while attenuating or eliminating the delivery of denervation energy to tissue from the remainder of the mesh structure 1772. Proximal and distal mesh end-caps 1772*a*, 1772*b* may be configured to substantially limit the resonant structure to the confines of the mesh structure 1772.

In some embodiments, the conductive mesh structure 1772 has density sufficient to limit radiation of microwave energy therethrough, except for one or more of the windows 1773*a*-1773*e* where the structure has a density of about zero. The clinical effect is therefore ablation of the renal artery in a pattern corresponding to the windows 1773*a*-1773*e*.

In some embodiments, the window region of the mesh 1772 may have a mesh density of greater than about $\frac{1}{10}\lambda$ (e.g., mesh elements spaced greater than $\frac{1}{10}\lambda$ apart), while the non-window region of the mesh may have a mesh density of less than about $\frac{1}{10}\lambda$ (e.g., mesh elements spaced less than $\frac{1}{10}\lambda$ apart). In some embodiments the window region of the mesh 1772 includes a non-conductive material or any material that is transparent to microwave energy. In other embodiments, the windows 1773*a*-1773*e* formed in conductive mesh structure 1772 are open and do not include any material what so ever.

During use, the flexible microwave catheter may be positioned adjacent to targeted tissue, the conductive mesh structure 1772 is then expanded, and an application of denervation energy is applied to tissue exposed to the windows 1773*a*-1773*e*.

FIG. 17B illustrates a renal artery RA after the application of denervation energy by the device illustrated in FIG. 17A. The denervation energy applied to the renal artery RA through each of the windows 1773*a*-1773*e* generates a corresponding denervation zone 1774*a*-1774*e*.

For illustrative purposes, the renal artery RA in FIG. 17B is provided with a plurality of renal nerves RN extending longitudinally along the renal artery RA. The denervation zones 1774*a*-1774*e* (and the corresponding windows 1773*a*-1773*e*) are longitudinally spaced from each other while providing circumferential overlap such that each of the individual renal nerves RN pass through at least one of the denervation zones 1774*a*-1774*d*. By this arrangement, denervation energy is applied to each of the renal nerves through at least one of the plurality of windows 1773*a*-1773*e* along the length of the renal artery RA.

Embodiments that provide circumferential overlap and/or circumferential delivery of energy may require a single treatment to obtain a desirable outcome.

Figure 18A:
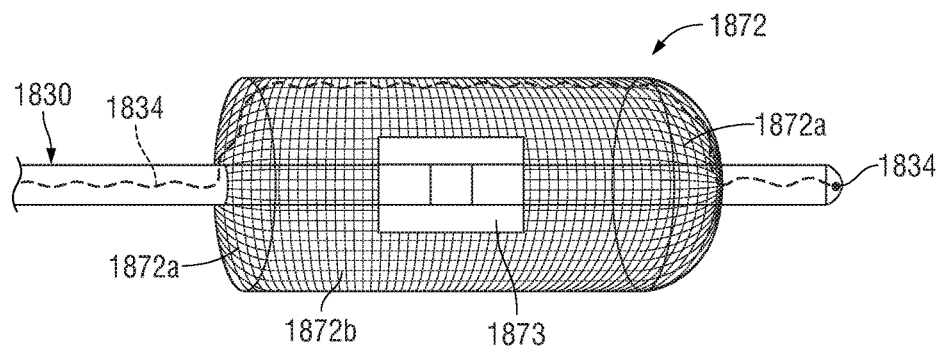
FIG. 18A is a perspective view of an embodiment of a conductive mesh structure that defines a window for selectively delivering denervation energy to tissue in accordance with some embodiments of the present disclosure.

As illustrated in FIG. 18A, a conductive mesh structure 1872 includes a window 1873 defined in at least a portion of the lengthwise section thereof. The conductive mesh structure 1872 is configured to enable the delivery of denervation energy to tissue through the window 1873, while attenuating or eliminating the delivery of denervation energy to tissue from the remainder of the mesh structure 1872. Proximal and distal mesh end-caps 1872*a*, 1872*b* may be configured to substantially limit the resonant structure to the confines of the mesh structure 1872.

In some embodiments, the window 1873 may include a mesh which includes a mesh density greater than about $\frac{1}{10}\lambda$. The non-window region of the conductive mesh 1872 may have a mesh density of less than about $\frac{1}{10}\lambda$.

Figure 18B:
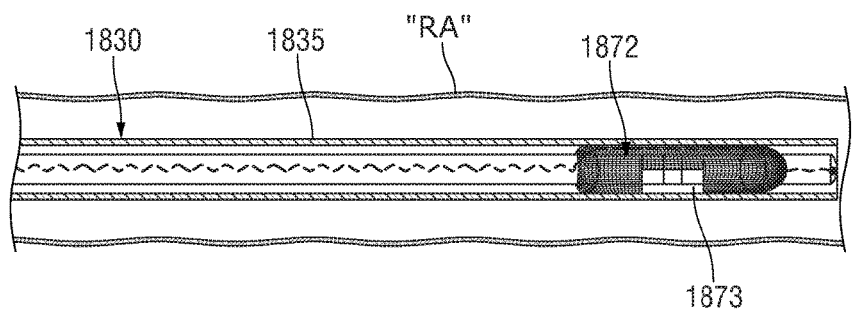
FIGS. 18B-18G are perspective views illustrating steps of a surgical procedure in accordance with some embodiments of the present disclosure utilizing the conductive mesh structure of FIG. 18A.
Figure 18C:
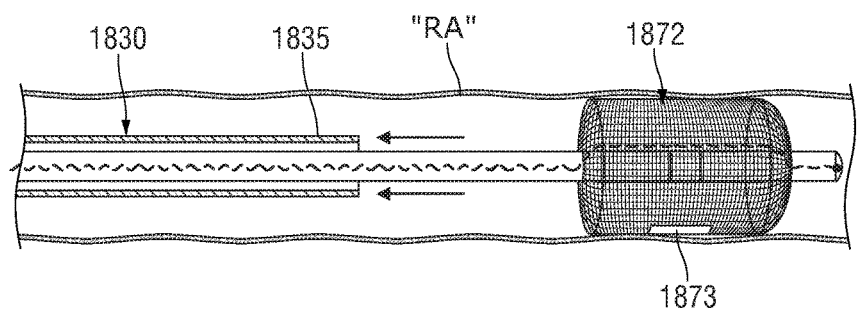
Figure 18D:
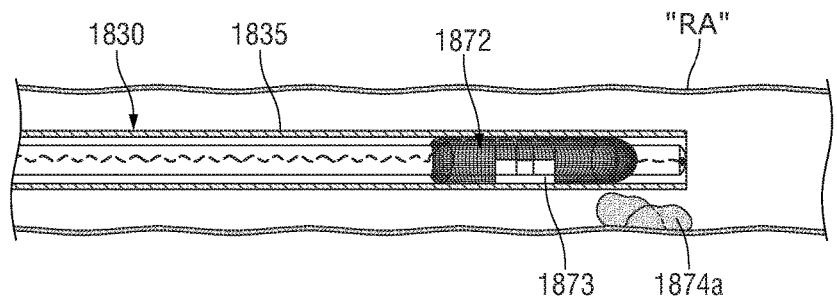
Figure 18E:
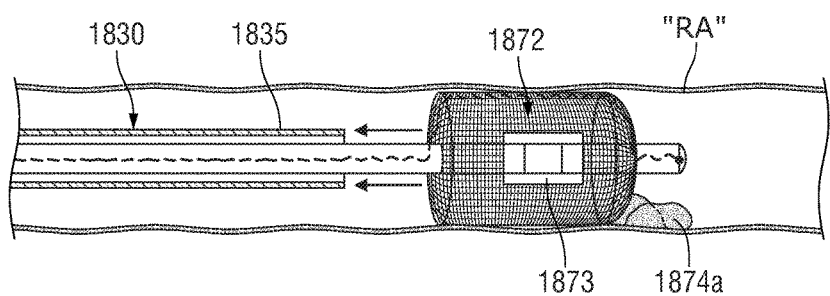
Figure 18F:
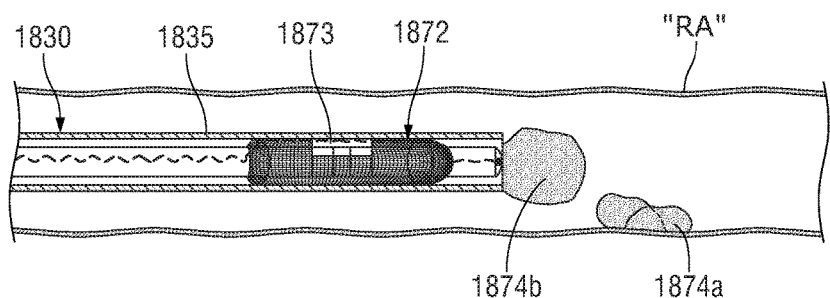
Figure 18G:
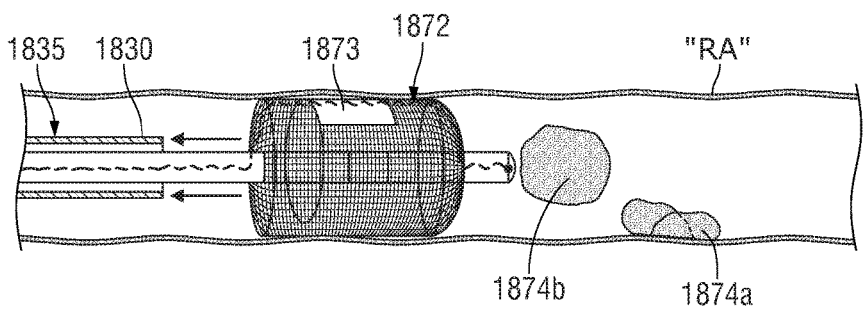

A method of applying denervation energy, utilizing the conductive mesh structure 1872 illustrated in FIG. 18A, is illustrated in FIGS. 18B-18H. As illustrated in FIG. 18B, the distal end of the flexible microwave catheter 1820 is positioned in a target artery (e.g., renal artery RA). As illustrated in FIG. 18C the outer sheath 1835 is retracted to remove the conductive mesh structure 1872 and the conductive mesh structure 1872 is expanded. The window 1873 is directed to a first target portion 1874*a* of the renal artery RA and a first application of denervation energy is applied to renal artery RA as first targeted tissue 1874*a* is exposed to the window 1873. After the initial application of denervation energy, the conductive mesh structure 1872 is repositioned, as illustrated in FIG. 18D, thereby exposing a different region (e.g., second targeted tissue 1874*b*) of the renal artery RA to the window 1873. The conductive mesh structure 1872 may be fully or partially collapsed during repositioning and subsequently re-expanded as illustrated in FIG. 18E. After repositioning the flexible microwave catheter 1820, a second application of denervation energy is applied to the second target tissue 1874*b*. As illustrated in FIGS. 18F-18G, subsequent repositions of the flexible microwave catheter 1830 and applications of denervation energy may be delivered in this manner as needed, thereby applying energy to a first, second, and third target tissue 1874*a*-1874*c*, and so forth.

The conductive mesh structure 1872 is initially positioned at a distal-most position within a body vessel, and drawn proximally for each subsequent repositioning. In some embodiments, the conductive mesh structure 1872 (and hence, the window 1873) is independently rotatable about the longitudinal axis of the flexible microwave catheter 1830. A rotating actuator 15*g* (see FIG. 7), such as without limitation, a knob or a lever, may be provided on the catheter hub 18 (see FIG. 7) to enable a surgeon to rotate and/or manipulate the conductive mesh structure 1872 in situ without the need to withdraw and re-insert the flexible microwave catheter, and/or without needing to rotate the entire flexible microwave catheter 1830.

The flexible microwave catheter 30 in FIGS. 18A-18H may include a temperature sensor 1834 at a distal end of the radiating portion 100. Temperature sensor 1834 may be used to measure the temperature of fluid circulating through the renal artery and passing through the proximal and distal end-cap mesh 1872*a*. The fluid temperature measured by the temperature sensor 1834 may be indicative of the energy delivered by the radiating portion 100. The fluid temperature measured by the temperature sensor 1834 may be indicative of the flow rate of fluid through the proximal and distal end-cap mesh 1872*a*. A low flow rate may be characterized by an unexpected rise in temperature, a change in the rate of temperature change, and/or the failure of a temperature decrease when energy delivery is terminated. Low flow rate may indicate the presence of a clot, emboli, or other blockage proximal the conductive mesh structure 1872.

Sensor leads 1834*a* are routed along the outer surface of the conductive mesh structure 1872. The conductive mesh structure 1872 at least partially isolates the sensor leads 1834*a* from the electromagnetic field generated by the radiating portion 100.

One or more indicia may be provided in association with the rotating actuator 15*g* to apprise a surgeon of the position of the conductive mesh structure 1872. In some embodiments, the conductive mesh structure 1872, or a portion thereof, is formed from material detectable by imaging techniques, thereby enabling a surgeon to determine the position thereof by fluoroscopic and other medical imaging devices, e.g., MRI and/or angiography.

Figure 19A:
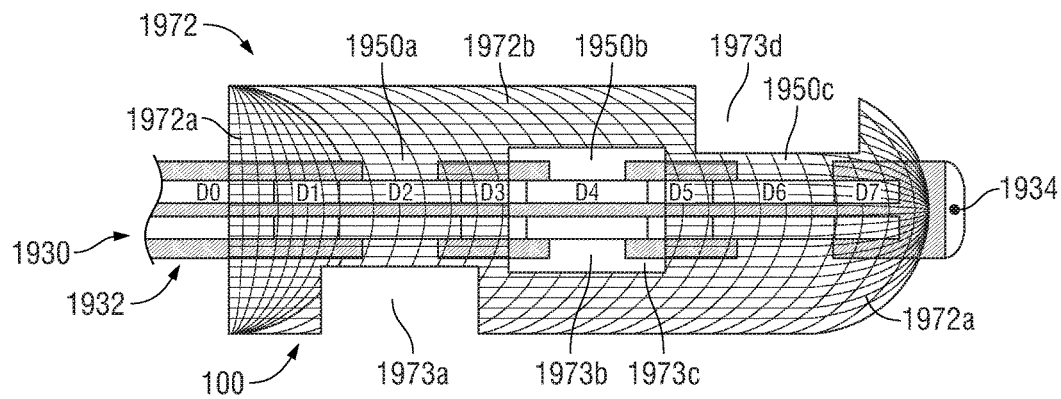
FIG. 19A is a perspective view of an embodiment of a conductive mesh structure that defines a plurality of windows for selectively delivering denervation energy to tissue in accordance with some embodiments of the present disclosure.

In some embodiments, the radiating portion 100 includes an antenna structure in accordance with the present disclosure that includes a plurality of feed gaps 1950*a*, 1950*b*, 1950*c* (e.g., energy feedpoints). FIG. 19A illustrates a flexible microwave catheter 1930 including a flexible coaxial cable 1932 connected to a radiating portion 100 on the distal end thereof with a plurality of radiating feed gaps 1950*a*-1950*c*. Radiating portion 100 includes a first radiating feed gap 1950*a*, a second radiating feed gap 1950*b* distal to the first radiating feed gap 1950*a*, and a third radiating feed gap 1950*c* distal to the first and second radiating feed gaps 1950*a*, 1950*b*. In these embodiments, the total power delivered to tissue is divided among the plurality of radiating feed gaps 1950*a*-1950*c*. A dimension of each feed gap 1950*a*-1950*c*, e.g., the longitudinal length of the exposed inner conductor, may be tailored to determine which fraction of the energy total is delivered by each respective feed gap 1950-1950*c*.

FIG. 19A illustrates just one non-limiting example having a radiating portion 100 with three radiating feed gaps 1950*a*-1950*c*. Since the energy arriving from the generator initially reaches the first radiating feed gap 1950*a*, the feed gap 1950*a* may be dimensioned to deliver one-third of the arriving energy. Moving to the second radiating feed gap 1950*b*, since one-third of the total energy was propagated by the first radiating feed gap 1950*a*, a remainder of two-thirds of the total energy arrives at the second radiating feed gap 1950*b*. Accordingly, the second radiating feed gap 1950*b* must propagate one-half the arriving energy to deliver one-third of the total energy to tissue. Finally, one-third of the total energy arrives at the third radiating feed gap 1950*c*, therefore, the third radiating feed gap 1950*c* must propagate one-hundred percent of the arriving energy to deliver one-third of the total energy to tissue.

In FIG. 19A, the radiating portion 100, with a plurality of radiating slots 1973*a*-1973*c*, includes a conductive mesh structure 1972 that centers the radiating portion within the conductive mesh structure 1972 and includes a plurality of windows 1973*a*-1973*d* for delivering denervation energy to tissue through the windows 1973*a*-1973*d*. In some embodiment, each window 1973*a*-1973*d* is configured to deliver denervation energy to 90 degrees of the circumference of the conductive mesh structure 1972. In some embodiments, the radial section of each window is related to the total number of windows.

In some embodiments, the dielectric constant of the coaxial insulation D0-D7 is selected to match a particular structure of the radiating portion 100. For example, the dielectric constant of the proximal coaxial insulation D0 may be related to the dielectric constant of the flexible coaxial cable 1832, and the dielectric constant of the remaining coaxial insulation D0-D7 is related to the specific section of the radiating portion 100.

Figure 51:
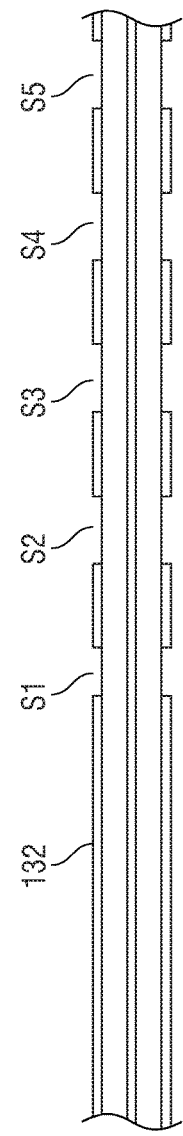
FIG. 51 illustrates an embodiment of a leaky waveguide having a varying slot width according to the present disclosure.

In some embodiments, the width of each feed gap 1950*a*-1950*c* varies to promote even energy delivery to each slot, as discussed in detail hereinbelow (see FIGS. 51 and 53).

In some embodiments, the proximal mesh structure 1972*a* and the distal mesh structure 1972*b* are configured to provide minimal restriction of fluid flow therethrough. A sufficient flow of fluid through the proximal mesh structure 1972*a* and the distal mesh structure 1972*b* provides a cooling effect and may prevent clotting. In some embodiments, the microwave energy delivery system halts the delivery of the microwave energy power signal if the blood temp approaches and/or rises above clotting levels.

Figure 19B:
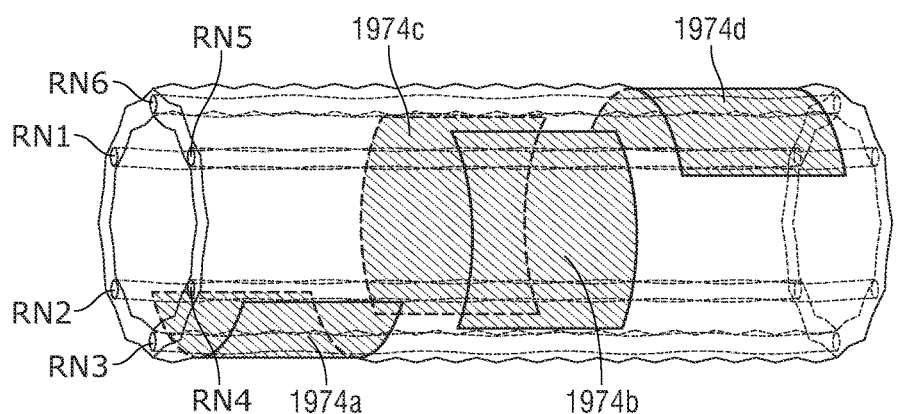
FIG. 19B is a perspective view of a portion of a renal artery after receiving selectively delivered denervation energy from the conductive mesh structure of FIG. 19A.

As illustrated in FIG. 19B, each window 1973*a*-1973*d* delivers denervation energy to a corresponding target tissue 1974*a*-1974*d* on the renal artery RA wherein at least a portion of tissue along the entire circumference of the renal artery RA is targeted along the longitudinal length thereof.

Figure 20:
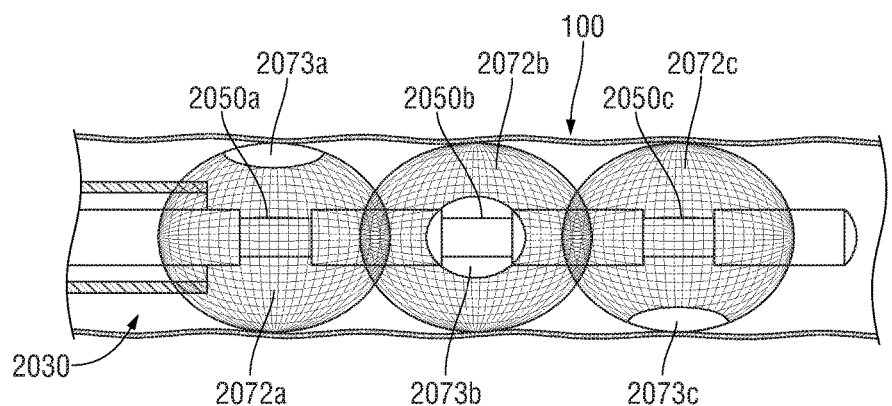
FIG. 20 is a side view of an embodiment of a radiating portion in accordance with some embodiments of the present disclosure having a plurality of conductive mesh structures each defining a window for selectively delivering denervation energy to tissue.

In some embodiments having a plurality of feed gaps, a plurality of corresponding conductive mesh structures 2072*a*-2072*c* is provided, as illustrated in FIG. 20. Each feed gap 2050*a*-2050*c* is operatively associated with an individual conductive mesh structure 2072*a*-2072*c*. Each individual conductive mesh structure 2072*a*-2072*c* may include a variable mesh density construction and/or one or more windows 2073*a*-2073*c*, as described herein. As illustrated in FIG. 20, the orientation of the windows 2073*a*-2073*c* may be arranged to radiate in differing directions (e.g. distributed radially). In some embodiments, the windows 2073*a*-2073*c* may be arranged to radiate in a similar direction (e.g., indexed radially).

One or more of the conductive mesh structures 2072*a*-2072*c* may be independently rotatable around a longitudinal axis of the flexible microwave catheter 2030, either individually or in tandem. One or more corresponding actuators 15*g* (see FIG. 7) may be provided, e.g., on the catheter hub 18 (see FIG. 7), and may enable remote positioning and/or monitoring of the conductive mesh structures 2072*a*-2072*c*.

An individual actuator may be selectively associated to one or more conductive mesh structures 2073*a*-2073*c*, thereby enabling the surgeon to manipulate/rotate arbitrary combinations of the conductive mesh structures 2072*a*-2072*c* as desired. For example, and without limitation, each conductive mesh structure 2072*a*-2072*c* may be associated with a switch that, when thrown, operatively couples the respective mesh structure to a dial actuator. One or more conductive mesh structures 2072*a*-2072*c* may be selected in this manner such that, as the dial actuator is turned, the chosen conductive mesh structures 2072*a*-2072*c* rotate accordingly. Other actuator control schemes and coupling arrangements may additionally or alternatively be included in a catheter or system in accordance with the present disclosure, including electromechanical or mechanical, utilizing, without limitation, a clutch, a pawl, a hydraulic coupling, a magnetorheological coupling, a motor, a stepper, one or more gears, one or more rollers, one or more pulleys, and so forth.

Figure 21:
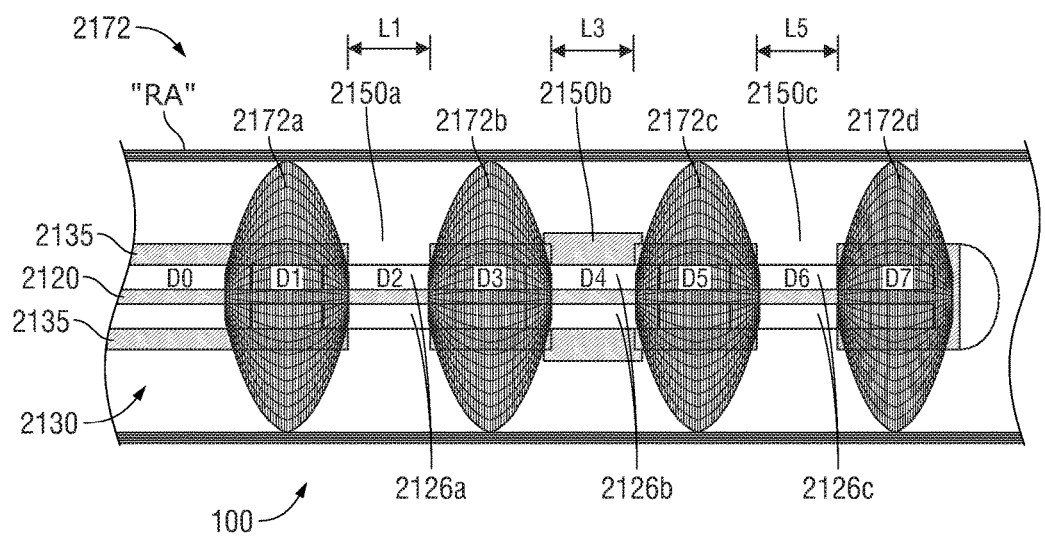
FIG. 21 is a side view of an embodiment of a radiating portion in accordance with some embodiments of the present disclosure having a plurality of conductive mesh structures that define a plurality of radiating portions.

As illustrated in FIG. 21, a flexible microwave catheter 2130 in accordance with the present disclosure may include one or more mesh structures 2172a-2172d arranged between, or adjacent to, one or more feed gaps 2150a-2150c. The mesh structures 2172a-2172d may be individually or collectively expandable and/or collapsible. The flexible microwave catheter may include an outer sheath 2135 that may be drawn distally to selectively deploy one or more of the mesh structures 2172a-2172d to vary the region of energy delivery. The dimensions of the feed gaps 2150a-2150c e.g., the length L1-L3 of each feed gap 2150a-2150c, may be tailored to distribute the denervation energy (e.g., the microwave energy) around the feed gaps 2150a-2150c as described herein. A length of transitional dielectric 2126a-2126c having a generally tubular shape may be coaxially disposed about the exposed inner conductor 2120 in one or more of the feed gaps 2150a-2150c, which may load each section, improve impedance matching, reduce reflections and/or standing waves, improve efficiently, and reduce the risk of embolism (e.g., clotting).

The mesh structures 2172a-2172d are configured to center the radiating portion 100 within the tubular body structure or body portion (e.g., renal artery RA). In some embodiments, the tubular body structure may not be uniformly shaped and the diameter of each of the mesh structures may vary to accommodate the non-uniform shape of the tubular body structure thereby centering the radiating portion 100 within the tubular body structure or body portion. Each of the mesh structures 2172a-2172d may be formed from different materials. In some embodiments, one or more of the mesh structures 2172a-2172d may be configured to function as a choke or balun thereby preventing at least a portion of the microwave energy signal from propagating longitudinally beyond the mesh structure 2172a-2172d. For example, in one embodiment the proximal mesh structure 2172a and distal mesh structure 2172d include a conductive material and configured to function as a choke or balun thereby preventing at least a portion of the microwave energy signal from propagating proximally from the proximal mesh structure 2172a and distally from the distal mesh structure 2172d (e.g., reduces propagation of microwave energy from the radiating portion in an axial direction).

In some embodiments, the proximal mesh structure 2172a and/or the distal mesh structure 2172d have a higher density to act as an effective electrical wall at the operational frequency of the radiating portion 100

In some embodiments, each of the mesh structures 2172a-2172d form a choke or balun thereby limiting the propagation of energy generated by each of the feed gaps 2150a. As illustrated in FIG. 21A, the distal portion of the flexible microwave catheter 2150 may be defined by zones D0-D7. Energy radiated in zone D0 is limited by the proximal mesh structure 2172a. Each mesh structure 2172a-2172d limits microwave energy in zones D1, D3, D5 and D7, respectively. The energy in zone 2 is limited to the energy radiated by first feed gap 2150a, the energy in zone 4 is limited to energy radiated by second feed gap 2150b, and the energy in zone 6 is limited to energy radiated by third feed gap 2150c.

In some embodiments, the proximal and/or distal surfaces may be selectively coated on a proximal and/or a distal surface with a conductive film, foil, and/or ink to enhance energy directionality.

As illustrated in FIGS. 22A-23B, a flexible microwave catheter 2230 in accordance with the present disclosure includes a distal mesh basket structure 2278a, 2278b having a basket-like and/or an umbrella-like shape. Distal mesh basket structure includes a distal apex and a proximal open (expandable) end. The apex of the distal mesh basket structure is anchored to, or adjacent to, a distal cap 2233 of the flexible microwave catheter 2230. By this arrangement, the distal mesh basket structure may capture any embolic material that may form during use, e.g., to prevent clots and other biomaterials from entering the bloodstream.

In FIG. 22A, the distal mesh basket structure 2278a and the mesh structure 2272a are configured to center the feed gap 2250 of the radiating portion 100 in the tubular body structure (e.g., renal artery RA) and/or improve the delivery of denervation energy by preventing or reducing the distal propagation of energy, as described herein.

In FIG. 22B, radiating portion 100 includes distal and proximal mesh structures for centering the feed gap 2250 of the radiating portion 100 in the natural body lumen (e.g., renal artery RA). The distal mesh basket structure 2278b is connected to the cap 2233 via a tether 2278c. Tether 2278c may be released by the rotating actuator 15g in the catheter hub 18 (see FIG. 7) or tether 2278c may be incorporated into a guide wire system.

As illustrated in FIG. 23, a stepped flexible microwave catheter 2330 in accordance with the present disclosure includes a stepped configuration wherein a proximal portion 2330a has a first, larger diameter and a distal portion 2330b has a second, smaller diameter. Generally, the amount of power deliverable by a system is determined, at least in part, by the size of the conductors therein. Larger proximal portion 2330a can accommodate a larger diameter flexible coaxial cable 2332a with conductors can handle more power than smaller conductors. Larger conductors tend to be less flexible than thinner conductors. Advantageously, the thinner, more flexible distal flexible coaxial cable 2332c of the disclosed stepped flexible microwave catheter 2330 enables facile feeding of the distal portion 2330b of the stepped flexible microwave catheter 2330 within the circuitous confines of a tubular body structure (e.g., the renal artery) or other body portion, while the larger, proximal portion 2330a of the stepped flexible microwave catheter 2330 is well suited for the larger, straighter tubular body structure (e.g., the femoral artery). The amount of energy deliverable to the targeted site may be increased, since the losses are reduced in the proximal portion 2330a of the stepped flexible microwave catheter 2330.

The flexible coaxial cable 2332a, 2332b in the respective proximal and distal portions 2330a, 2330b of the stepped flexible microwave catheter 2330 are coupled by a tapered matching network 2332c. The tapered matching network 2332c may include a linear tapered portion and/or an exponential tapered portion. Additionally or alternatively, different dielectric layers may be utilized within the flexible coaxial cable 2332 in the proximal section 2330a, the tapered section 2332c, and/or the distal section 2332c to improve matching, reduce reflections/standing waves (VSWR), and reduce losses.

As illustrated in FIG. 24, in some embodiments in accordance with the present disclosure, the radiating portion of a flexible microwave catheter 2430 for natural lumens includes an inflatable balloon 2479 formed from biocompatible elastomeric material. The inflatable balloon 2479 may be inflated with any suitable media, including without limitation a dielectric fluid (e.g., saline or deionized water) and/or a gas (e.g., air, $CO_2$, etc.) In some embodiments, the feed gap 2450 may be included within the inflatable balloon 2479 and the dielectric fluid and/or a portion of the inflatable balloon may form part of an anatomical resonant structure as discussed herein. The inflatable balloon 2479 may include one or more conduits or channels disposed in a generally longitudinal orientation that are arranged to facilitate the flow of vascular fluid (e.g., blood flow) past the balloon while in use (see FIGS. 25A-25B and 26A-26C). One or more fluid ports may be provided in a proximal portion of the catheter and/or the tip of the catheter that are in fluid communication with the one or more balloon conduits to enhance the flow of vascular fluid therethrough. At least a part of the balloon may include a conductive layer disposed thereon (see FIGS. 58A-58D). The conductive layer may be disposed on an outer surface, or preferably, an inner surface of the balloon. The conductive layer may be formed by any suitable manner of coating or deposition, including without limitation, thin film deposition, plating, application of conductive ink, foil, and the like. In some embodiments, the conductive layer is formed from conductive silver ink. The conductive layer may be formed in a pattern, e.g., a spiral pattern, a lattice pattern, a halftone pattern, a gradient pattern, or any pattern that facilitates the elastic inflation and deflation of the balloon while maintaining conductivity among and between the elements of the conductive layer pattern. In some embodiment, spiral regions of transparent (e.g., no ink coverage) may have a width of about 3-5 mils (0.003"-0.005"). By this arrangement, a Faraday cage may be formed by the conductive layer, which may improve the radiation pattern and hence delivery of denervation energy. For example, and without limitation, a balloon in accordance with this disclosure may include a spiral conductive pattern disposed at the proximal and distal ends thereof, while having little, or no, conductive material along the middle portion. In embodiments, the balloon structure may include conductive patterns arranged in accordance with the heretofore described configuration(s) of a mesh structure, e.g., a windowed balloon (having conductive coating on all but a windowed portion of the balloon), multiple balloons, a single balloon with multiple windows, rotatable balloon(s), and so forth.

Figure 25A:
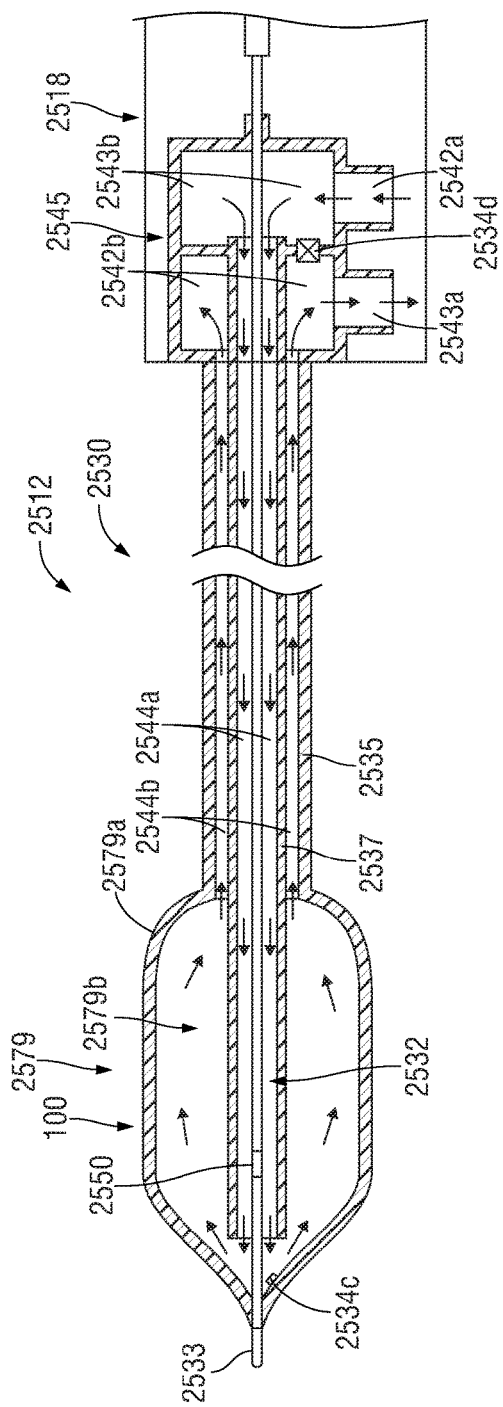
FIG. 25A is a longitudinal, cross-sectional view of an embodiment of a microwave energy delivery system having a distal radiating portion within an inflatable balloon in accordance with some embodiments of the present disclosure.

FIG. 25A illustrates a microwave energy delivery system 2512 according to some embodiments of the present disclosure that includes a catheter hub 2518 connected to a flexible microwave catheter 2530 with a distal radiating portion 40 within an inflatable balloon 2579 on the distal end thereof. System 2512 only illustrates aspects related to the inflatable balloon 2579 although it is understood that any aspect or embodiment described herein may be incorporated into the system 2512.

Balloon catheter hub 2518 includes a balloon fluid coupler 2545 for inflating and/or deflating the inflatable balloon 2579. Balloon catheter hub 2518 may also include any other aspects of the catheter hubs 18 and coupler 45 or adjustable fluid coupler 845 described herein (see FIGS. 7-9C). Balloon fluid coupler 2545 forms inflow and outflow ports 2542a, 2543a that are in fluid communication with inflow and outflow plenums 2542b, 2543b, respectively. Inflow and outflow plenums 2542b, 2543b are in fluid communication with respective inflow and outflow fluid passageways 2544a, 2544b formed between a fluid flow lumen, the flexible coaxial cable 2532 and the outer sheath 2535.

Figure 25B:
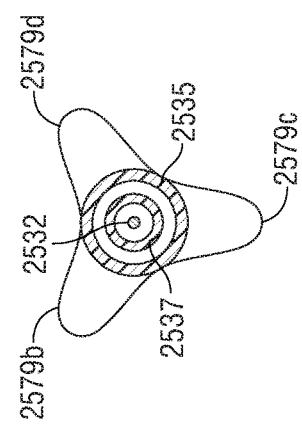
FIG. 25B is a transverse, cross-sectional view of an embodiment of the distal radiating portion of the microwave energy delivery system of FIG. 25A.

As illustrated in FIGS. 25A-25B, inflatable balloon 2579 includes an inflatable material 2579a that forms the outer surface of a balloon cavity 2579b. Balloon cavity 2579b may include one or more chambers formed by each balloon lobe 2579b-2579d. In some embodiments, inflatable balloon 2579 includes three lobes 2579b-2579d wherein the cavities formed by each balloon lobe 2579b-2579c are inflated by fluid provided from the inflow fluid passageway 2544a.

Balloon lobes 2579b-2579d are configured to center the radiating portion 100 in a body lumen or body portion. Balloon lobes 2579b-2579d provide a passageway for fluid to pass between each balloon lobe 2579b-2579d and the body lumen wherein fluid flow provides cooling to the balloon lobes 2579b-2579d and the body lumen.

Maintaining sufficient blood flow past the radiating portion is critical in cases, such as balloon centering devices, where the device would otherwise block critical blood flow to distal tissues. As such, any of the inflatable balloons 2579 described herein, in addition to any of the other centering devices and flexible microwave catheters 30, may be made to have multiple invaginations (e.g., pleats, channels or interfolding parts), about its circumference such that fluid (blood) may continue to pass over the structure while it is placed.

Fluid from the inflow fluid passageway 2544a is delivered to the distal-most portion of the balloon cavity 2579b, adjacent the cap 2533. Fluid exits the balloon cavity 2579b through the outflow fluid passageway 2544b connected to the proximal-most portion of the balloon cavity 2579b. As such, fluid travels proximally through the balloon cavity 2579b thereby proving an additional cooling source to the radiating portion 100. In some embodiments, fluid flow is needed to dissipate heat generated by the radiating portion 100 and to maintain a dielectric buffer.

Inflatable balloon 2579 may be pre-formed to include the balloon lobes 2579b-2579. In some embodiments, the inflatable material 2579a is joined to the radiating portion 100 between each lobe 2579b-2579d.

System 2512 may include pressure regulation to maintain pressure in the inflatable balloon 2579. Maintaining pressure may be required to maintain antenna position and to maintain the passageway between the inflatable balloon and the body lumen. Pressure regulation may be accomplished by regulating the pressure at the outflow port 2542a using a pressure sensor as feedback to the pump or mechanical regulator in the fluid cooling system 40 (See FIG. 7). Pressure regulation may be achieved by maintaining a differential pressure between the inflow port 2542 and the outflow port 2543a with a differential pressure regulator 2534d in the balloon fluid coupler 2545.

In some embodiments, fluid in the inflatable balloon is expelled into the tubular lumen and/or body structure. Inflatable balloon 2579 receives fluid from an inflow fluid passageway 2544a. To maintain pressure in the inflatable balloon 2579 and/or to maintain the shape of inflatable balloon 2579, fluid in the inflatable balloon 2579 escapes through an orifice formed in the inflatable material 2579a. The amount of fluid expelled into the tubular lumen and/or body structure may depend on the length of the procedure and the size of the orifice.

The pressure may also be regulated by performing an anatomical measurement. For example, if used in a vascular system, the pressure in the inflatable balloon 2579 may also be regulated using a pressure sensor 2542e to detect the systolic blood pressure pulses inside the inflatable balloon 2579. Pressure pulses measured inside of the inflatable balloon 2579 would increase as the vascular structure became more occluded by inflation of the inflatable balloon 2579 and decreasing pressure pulses would indicate a less inflated balloon 2579.

Figure 26A:
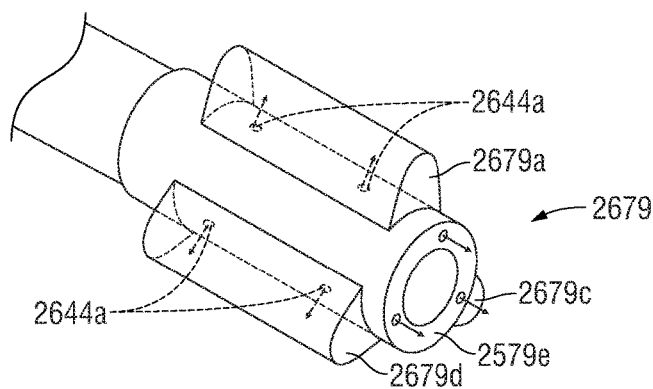
FIG. 26A is a perspective view of an embodiment of an inflatable balloon having a plurality of lobes for centering a radiating portion in a body lumen in accordance with some embodiments of the present disclosure.
Figure 26B:
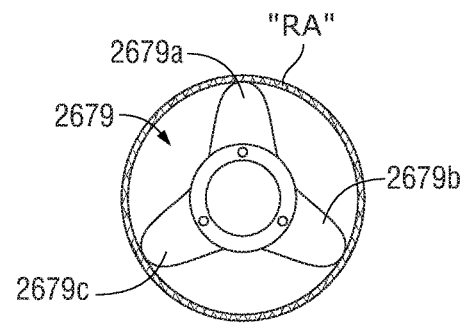
FIG. 26B is a transverse, cross-sectional view of the inflatable balloon of FIG. 26A.
Figure 26C:
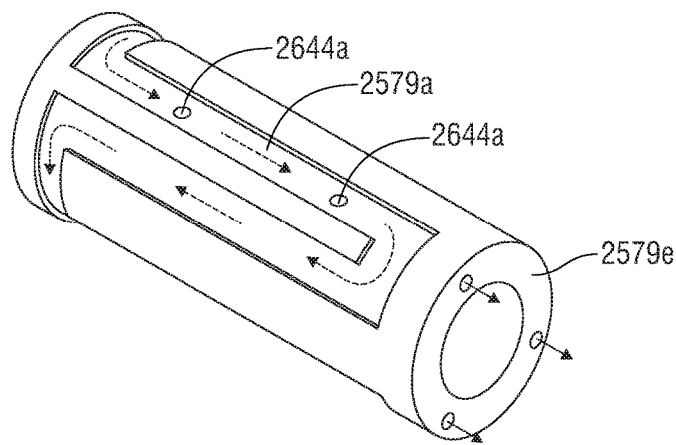
FIG. 26C is a perspective view of the housing of the inflatable balloon of FIG. 26A.

FIGS. 26A-26C illustrate another embodiment of an inflatable balloon 2679 for centering a radiating portion in a body lumen (e.g., renal artery RA). Inflatable balloon 2679 includes first, second, and third lobes 2679b-2679d that are joined to an inflatable balloon housing 2679e. Inflatable balloon housing 2679e forms an internal chamber that houses cooling fluid. Cooling fluid from the inflatable balloon housing 2679e flows to the first, second, and third lobes 2679b-2679d via a plurality of inflow fluid passageways 2644a.

FIGS. 27A-41B illustrate various centering devices that may be used to position a radiating portion according to the present disclosure within a body lumen or body structure. One or more centering device may be connected to any portion of the flexible microwave catheter. In some embodiments the centering devices are connected to a deployable portion wherein in a first undeployed position, the centering device is in a constrained condition, and in a second deployed position, the centering device is in an unconstrained condition, e.g., expanded and configured to center the radiating portion in the body lumen.

Figure 27A:
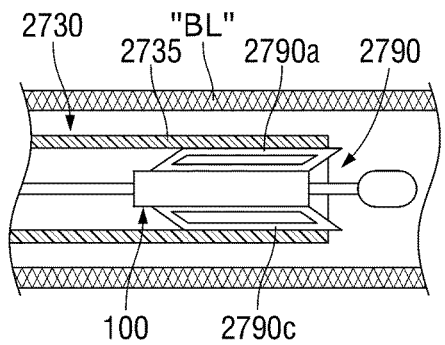
FIGS. 27A-27B are longitudinal and transverse cross-sectional views, respectively, of a centering device housed in the outer sheath of the flexible microwave catheter in accordance with some embodiments of the present disclosure.
Figure 27B:
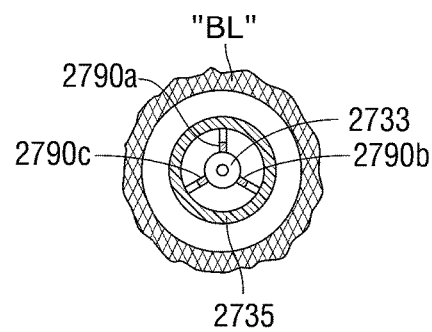

FIGS. 27A-27D illustrate centering fins 2790 for centering a radiating portion 100 in a body lumen BL. Centering fins 2790 include first, second, and third fins 2790a-2790c that connect to a portion of a flexible microwave catheter 2730. FIG. 27A illustrates the centering fins 2790 restrained within the outer sheath 2735. Centering fins 2790 are illustrated distal to the radiating portion 100 however centering fins 2790 may be positioned adjacent or proximal the radiating portion 100. FIG. 27B is a transverse cross-section of FIG. 27A that illustrates each of the fins 2790a-2790c restrained by the outer sheath 2735 and offset by about 120 degrees with respect to each other.

Figure 27C:
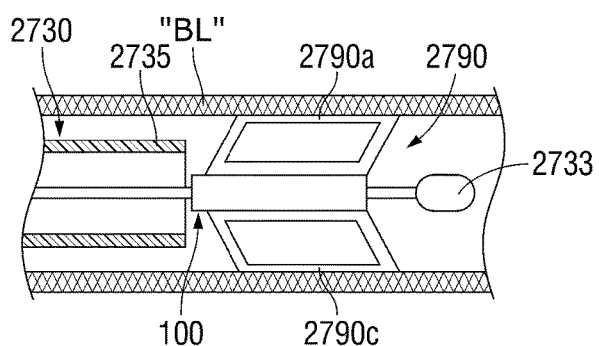
FIG. 27C is a longitudinal cross-sectional view of an embodiment of a centering device deployed from the outer sheath of a flexible microwave catheter in accordance with some embodiments of the present disclosure.
Figure 27D:
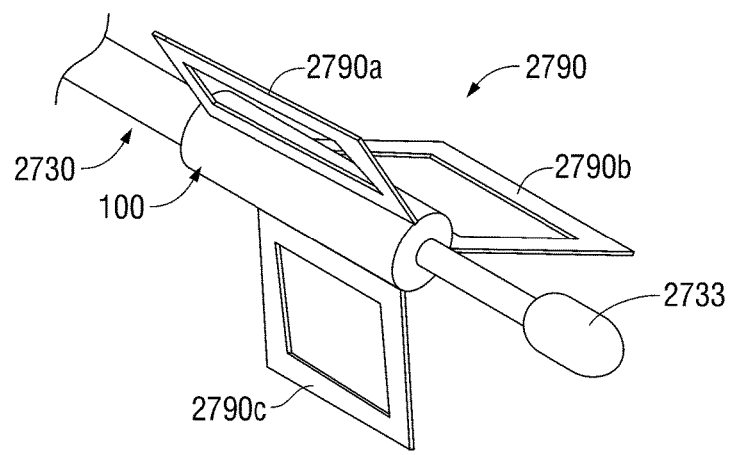
FIG. 27D is a perspective view of the centering device of FIGS. 27A-27C in a deployed position.

In FIGS. 27C-27D the centering fins 2790 and radiating portion 100 are deployed from the outer sheath 2735. Fins 2790a-2790c, when released from the constraints of the outer sheath 2735, center the radiating portion 100 about the center of the body lumen BL. After use, the centering fins 2790 and radiating portion 100 are retracted to a constrained position (see FIG. 27A) within the outer sheath 2735.

As illustrated in FIG. 27C, centering fins 2790 may center the radiating portion 100 by contacting with the body lumen BL. In some embodiments, centering fins 2790 self center the radiating portion 100 via fluid/hydrodynamic, and/or mechanical forces within the body lumen BL thereby ensuring even energy delivery.

In some embodiments, cap 2733 extends distally from the flexible microwave catheter 2730 and longitudinally positions the radiating section 100 adjacent a targeted tissue in a body lumen. For example, cap 2733 may be dimensioned to enter, and/or become lodged in, a branch of the renal artery at the hilum of the kidneys. The distance between the cap 2733 and the radiating portion 100 is dimensioned such that the radiating portion 100 is positioned adjacent a target tissue in the renal artery.

Figure 28:
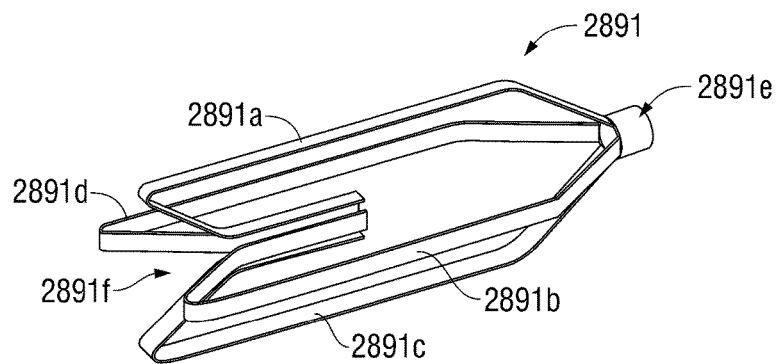
FIG. 28 is a perspective view of an embodiment of a four-prong centering device in accordance with some embodiments of the present disclosure.

FIG. 28 illustrates a four-prong centering device 2891 that includes four prongs 2891a-2891d that connect to a distal receiver 2891e and form a proximal receiver 2891f. Distal receiver 2891e and proximal receiver 2891f are each configured to receive a portion of a flexible coaxial cable (not shown) therethrough.

Figure 29:
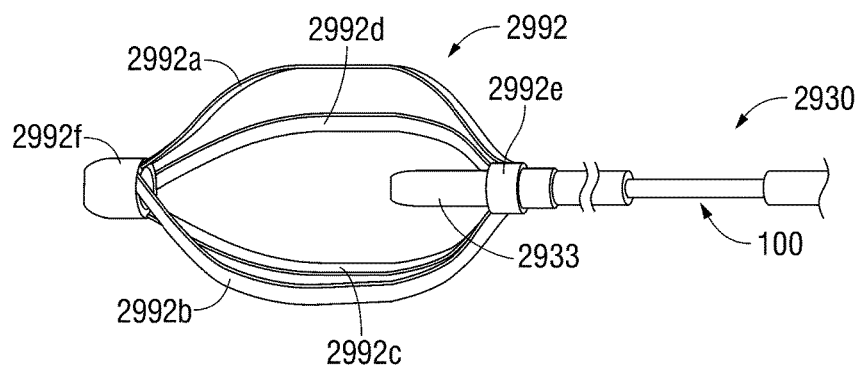
FIG. 29 is perspective view of an embodiment of a centering basket adapted to center a radiating portion of a distal portion of a flexible microwave catheter in accordance with some embodiments of the present disclosure.

FIGS. 29-32 illustrate a centering basket 2992 for centering a radiating portion 100 in a body lumen BL. Each centering basket 2992 include first, second, third, and fourth bands 2992a-2992d that connect to proximal receiver 2992e and distal receiver 2992f. In some embodiments, at least one of the proximal receiver 2992e and the distal receiver 2992f is fastened to a portion of the flexible microwave catheter while the other slides freely of the flexible microwave catheter. As such, in a deployed condition the centering basket 2992 is expanded, as illustrated in FIG. 29. In an undeployed condition (e.g., constrained with an outer sheath or similar device) the bands 2992a-29992d are compressed thereby elongating the centering basket 2992.

In FIG. 29, the proximal receiver 2992e is distal to the radiating portion 100 and connected to the elongated cap 2933. Distal receiver 2992f is unrestrained and extends distally from the elongated cap 2933. In some embodiments, distal end of elongated cap 2933 includes a rounded surface to facilitate insertion and/or navigation of the flexible microwave catheter 2930 to a targeted tissue.

Figure 30:
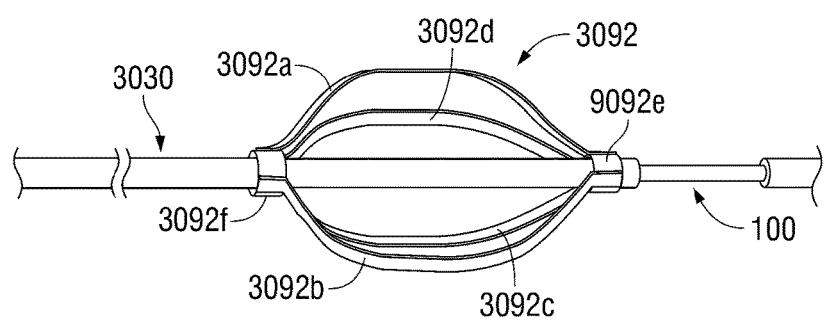
FIG. 30 is perspective view of an embodiment of a centering basket adapted to center a radiating portion of a flexible microwave catheter proximal the radiating portion in accordance with some embodiments of the present disclosure.

In FIG. 30, the centering basket 3092 is positioned proximal the radiating portion 100. The distal receiver 3092e is fastened to the flexible microwave catheter 3030. Proximal receiver 3092f slides freely over the flexible microwave catheter 3030 thereby allowing the centering basket 3092 to be compressed and elongated when constrained within an outer sheath or similar device (not explicitly shown).

Figure 31:
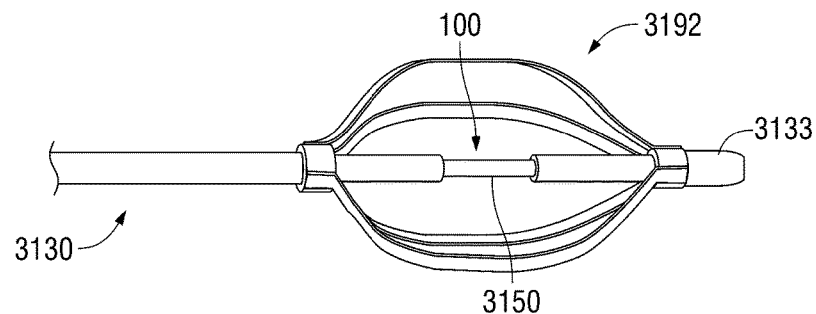
FIG. 31 is perspective view of an embodiment of a centering basket adapted to center a radiating portion in accordance with some embodiments of the present disclosure.

In FIG. 31, the centering basket 3192 is centered about the radiating portion 100 wherein the distal receiver 3192e is fastened to the flexible microwave catheter 3130 between the radiating portion 100 and the cap 3122. The proximal receiver 3192f slides freely over the flexible microwave catheter 3030 proximal the radiating portion 100, thereby allowing the centering basket 3192 to be compressed and elongated when constrained within an outer sheath or similar device.

Figure 32A:
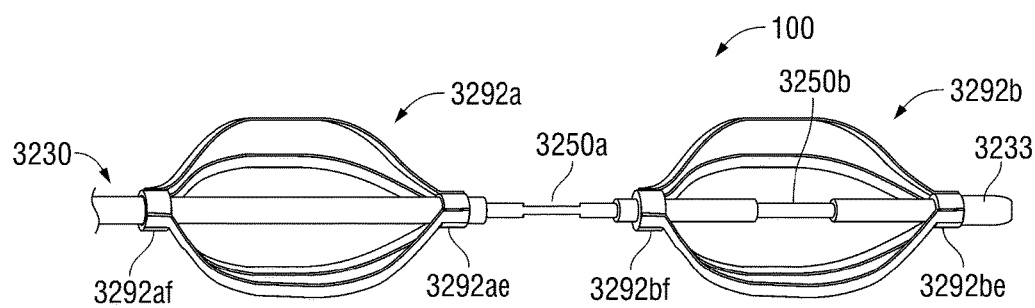
FIG. 32A is a perspective view of an embodiment of a proximal centering basket and a distal centering basket operably coupled to the distal end of a flexible microwave catheter in accordance with some embodiments of the present disclosure.
Figure 32B:
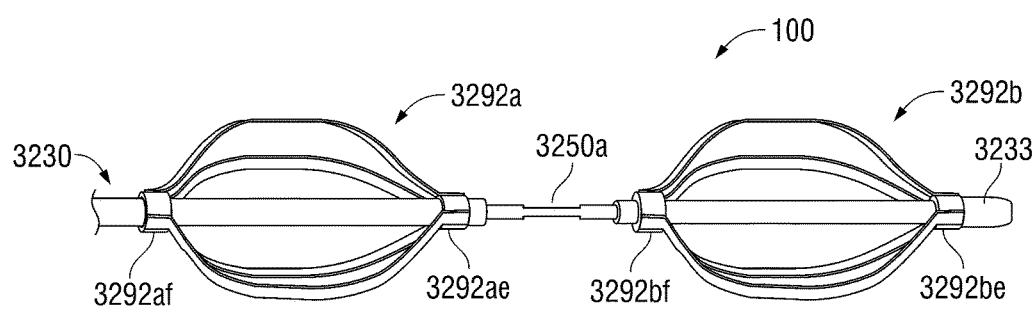
FIG. 32B is a perspective view of an embodiment of a proximal centering basket and a distal centering basket operably coupled to the distal end of a flexible microwave catheter in accordance with some embodiments of the present disclosure.

In FIGS. 32A and 32B, a proximal centering basket 3292a and a distal centering basket 3292b are connected to the flexible microwave catheter 3230. The proximal centering basket 3292a and the distal centering basket 3292b are configured to center the radiating portion 100 that includes a proximal feed gap 3250a and a distal feed gap 3250b in FIG. 32A and a proximal feed gap 3250a in FIG. 32B. The proximal centering basket 3292a is positioned proximal to the proximal feed gap 3250a and the distal receiver 3292ae is fastened to the flexible microwave catheter 3230. Proximal receiver 3292af of the proximal centering basket 3292a slides freely over the flexible microwave catheter 3230, thereby allowing the proximal centering basket 3292a to be compressed and elongated when constrained within an outer sheath or similar device (not explicitly shown).

In FIG. 32B, the distal centering basket 3292b is centered on the distal feed gap 3250b wherein the distal receiver 3292be is fastened to the flexible microwave catheter 3130 between the distal feed gap 3250 and the cap 3233. The proximal receiver 3292bf of the distal centering basket 3292b slides freely over the flexible microwave catheter 3230 proximal the distal feed gap 3250b, thereby allowing the distal centering basket 3292b to be compressed and elongated when constrained with an outer sheath or similar device.

In FIG. 32B, the proximal feed gap 3250a is centered between the proximal centering basket 3292a and the distal centering basket 3292b. In some embodiments, the proximal centering basket 3292a is positioned proximal to the proximal feed gap 3250a and the distal receiver 3292ae is fastened to the flexible microwave catheter 3230 such that the proximal receiver 3292af of the proximal centering basket 3292a slides freely over the flexible microwave catheter 3230. The distal centering basket 3292b is positioned distal to the proximal feed gap 3250a and the distal receiver 3292be is fastened to the flexible microwave catheter 3130 proximal the cap 3233 such that the proximal receiver 3292bf slides freely over the flexible microwave catheter 3230. As such, the proximal and distal centering baskets 3292a, 3292b may be compressed and elongated when constrained with an outer sheath or similar device.

Figure 33:
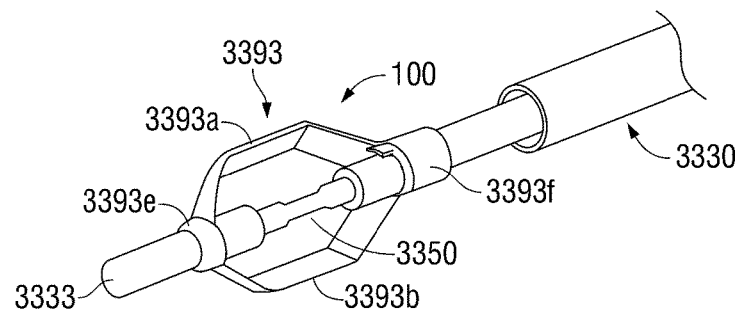
FIG. 33 is a perspective view of an embodiment of a dual-band centering device centered on the radiating portion in accordance with some embodiments of the present disclosure.

In FIG. 33, a dual-band centering device 3393 is centered about the feed gap 3250 of the radiating portion 100. Dual-band centering device 3393 includes a proximal receiver 3393f that is fastened to the flexible microwave catheter 3333, and a distal receiver 3393b that slides freely over the cap 3333 of the flexible microwave catheter 3330.

Dual-band centering device 3393 includes a first and second bands 3393a, 3393b, respectively, that are offset 180 degrees from each other. As such, the dual-band centering device 3393, when expanded in a body lumen BL, elongates the body lumen BL with respect to the first and second bands 3393a, 3393b while drawing the body lumen BL toward the feed gap 3350 of the radiating portion 100 (e.g., along each of the side of the dual-band centering device 3393). In this manner, the dual-band centering device 3393 shapes the body lumen into an oblong shape wherein the portion drawn toward the feed gap 3350 will generate hot spots due to the oblong coaxial arrangement.

Figure 34:
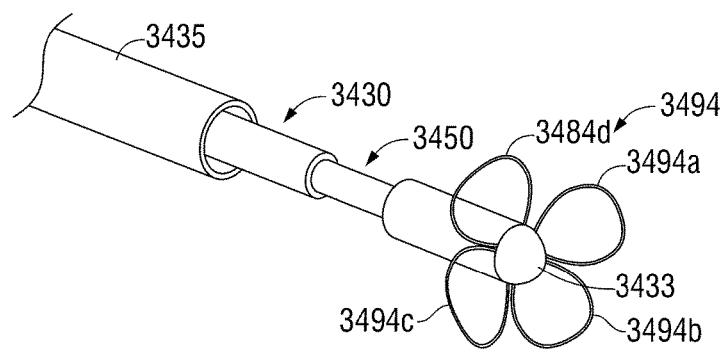
FIG. 34 is a perspective view of an embodiment of a clover-leaf centering device including a plurality of petals for centering a radiating portion in accordance with some embodiments of the present disclosure.

In FIG. 34, a clover-leaf centering device 3494 is connected to the cap 3433 distal to the feed gap 3450 of the radiating portion 100. Clover-leaf centering device 3494 includes a plurality of petals 3494a-3494d equally spaced about the circumference of the flexible microwave catheter 3430. Petals 3494a-3494d may be formed from a shape-memory material, such as nitonal, such that the petals 3494a-3493d expand outward to form the clover-leaf shape after being deployed from the outer sheath 3435.

In some embodiments, a clover-leaf centering device 3494 is electrically isolated from the radiating portion 100. Clover-leaf centering device 3494 may be joined by a dielectric having adhesive properties (e.g., dielectric glue) thereby preventing metal-to-metal contact between the petals 3494a-3494d of the clover-leaf centering device 3494 and/or any metallic portion of the in the radiating portion 100.

Figure 35:
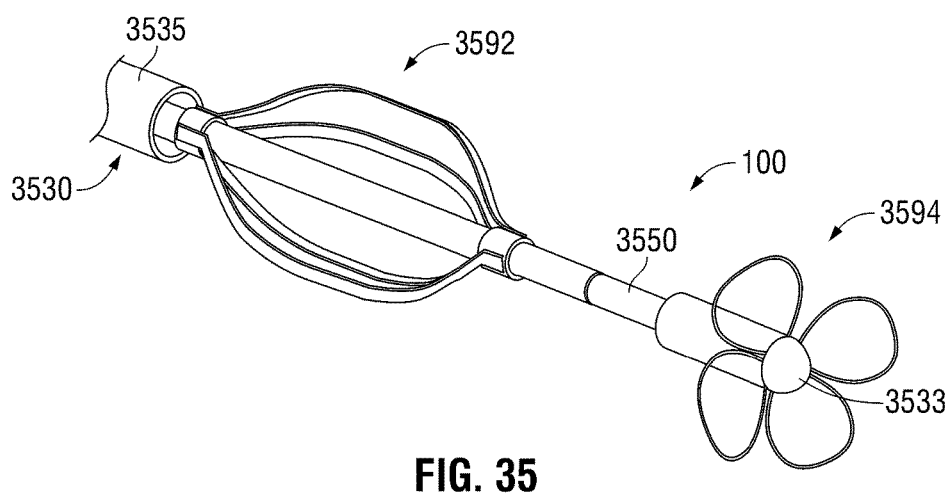
FIG. 35 is a perspective view of an embodiment of the distal end of a flexible microwave catheter including a clover-leaf centering device and a centering basket in accordance with some embodiments of the present disclosure.

In FIG. 35, a flexible microwave catheter 3530 includes a clover-leaf centering device 3594 and a centering basket 3592. Clover-leaf centering device 3594 is joined to the distal cap 3533 and positioned distal the feed gap 3550 of the radiating portion 100. Centering basket 3592 is positioned on a portion of the flexible microwave catheter 3530 proximal to the feed gap 3550.

Figure 36A:
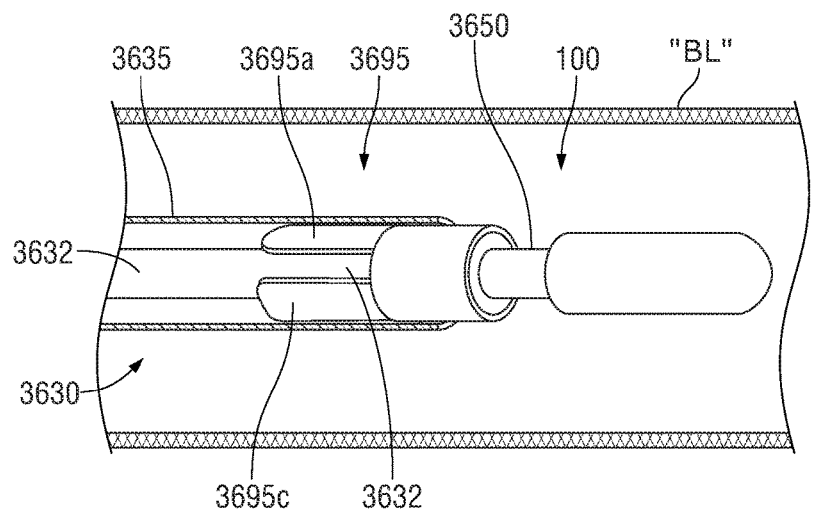
FIGS. 36A and 36B are perspective views of an embodiment of a deployable paddle centering device in accordance with some embodiments of the present disclosure.
Figure 36B:
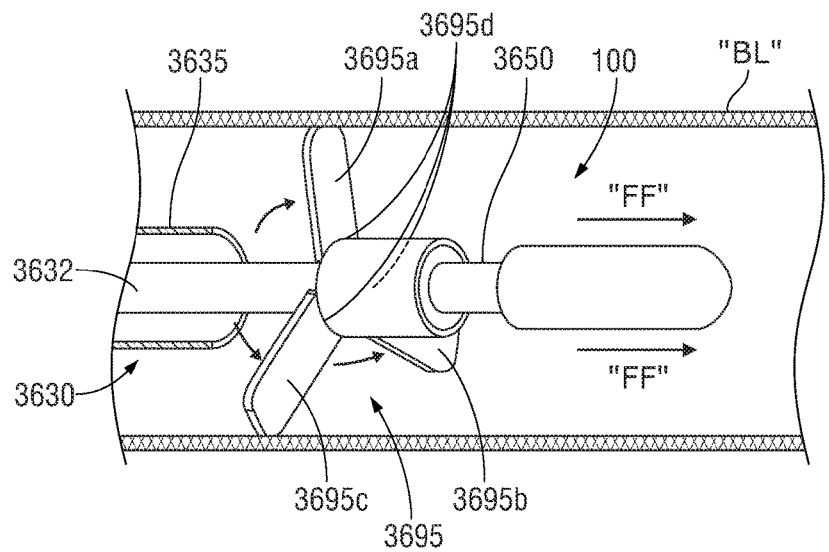

FIGS. 36A and 36B illustrate a paddle centering device 3695 according to some embodiments of the present disclosure. Paddle centering device 3695 includes first, second, and third paddles 3695a-3695c fixed to a portion of the flexible microwave catheter 3650. Paddles 3695a-3695c may be fixed by a hinge-like attachment 3695d that pivotally attaches and/or hingedly attachments each paddle 3695a-3695c to the flexible coaxial cable 3632.

In FIG. 36A, the paddles 3695a-3695c of the paddle centering device 3695 are constrained within the outer sheath 3635 of the flexible microwave catheter 3630. In the constrained condition, the paddles 3695a-3695c are folded inward and positioned adjacent the flexible coaxial cable 3632.

In FIG. 36B, the flexible coaxial cable 3632 and paddles 3695a-3695c are shown deployed from the outer sheath 3635 of the flexible microwave catheter 3630. Paddles 3695a-3695c are opened by moving each paddle about the hinge-like attachment. In the open position, paddles 3695a-3695c are prevented from over-extending by a paddle stop 3695e, and/or motion is limited by the hinge-like connection 3695d. In some embodiments, the paddle stop 3695e is a choke or balun formed on the flexible coaxial cable 3532.

Paddles 3695a-3695c may articulate between a closed condition, as illustrated in FIG. 36A, and an open condition, as illustrated in FIG. 36B. In some embodiments, articulation may be affected by an actuator on the catheter hub 18 (see FIG. 7). In some embodiments, articulation may be affected by the deployment of the flexible coaxial cable 3632 from the outer sheath 3635.

Paddle centering device 3695 may include any number of paddles 3695a-3695c symmetrically positioned (e.g., regularly distributed) about the flexible microwave catheter 3730. In some embodiments, the paddles 3695a-3695c are substantially identical in length and width, although in some embodiments, paddles 3695a-3695c may vary in length and/or width thereof.

Figure 37A:
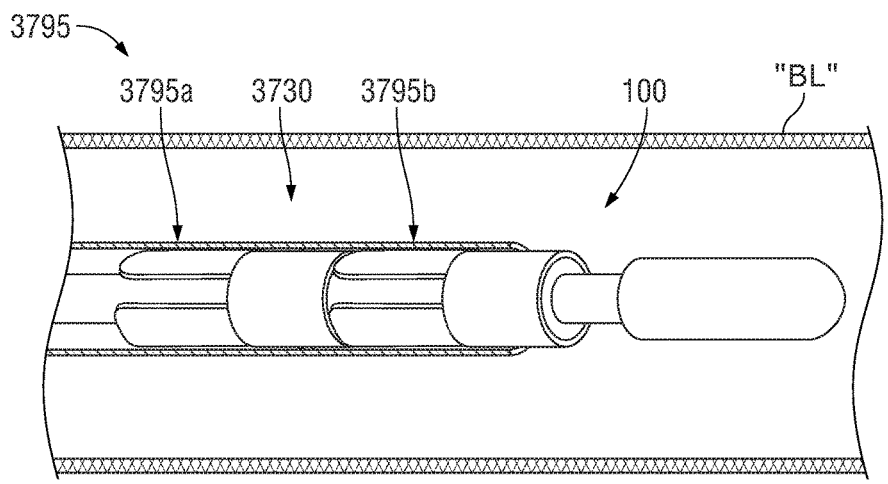
FIGS. 37A and 37B are perspective views of an embodiment of a deployable dual paddle centering device in accordance with some embodiments of the present disclosure.
Figure 37B:
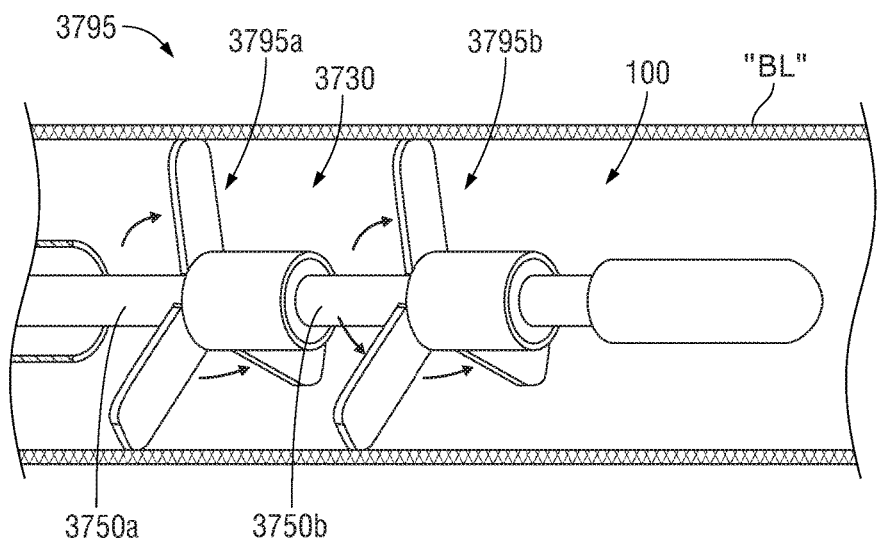

FIGS. 37A and 37B illustrate a dual paddle centering device 3795 according to some embodiments of the present disclosure. Dual paddle centering device 3795 includes a proximal paddle centering device 3795a and a distal paddle centering device 3795b. Proximal paddle centering device 3795a is positioned on the flexible microwave catheter 3730 between the first feed gap 3750a and the second feed gap 3750b. Distal paddle centering device 3795b is positioned on the flexible microwave catheter 3730 between the second feed gap 3750b and the third feed gap 3750c. Proximal paddle centering device 3795a and a distal paddle centering device 3795b center the first feed gap 3750a, second feed gap 3750b, and third feed gap 3750c in the body lumen BL.

Figure 38A:
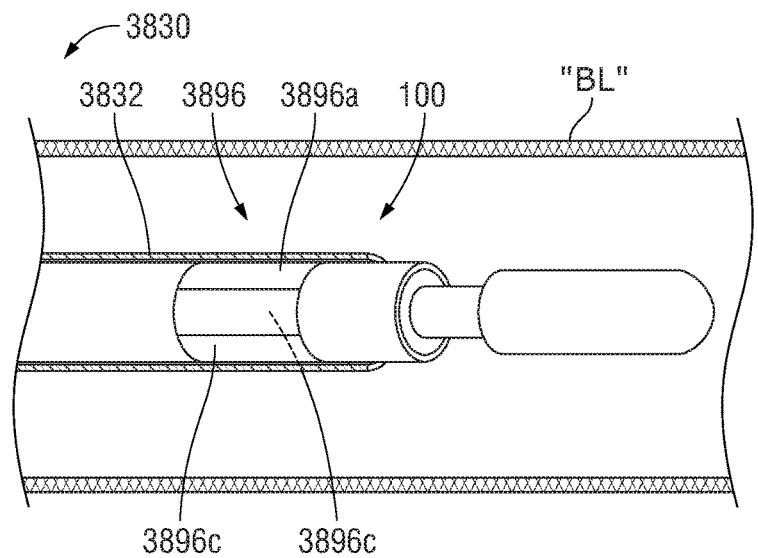
FIGS. 38A and 38B are perspective views of an embodiment of a deployable paddle centering device in accordance with some embodiments of the present disclosure.
Figure 38B:
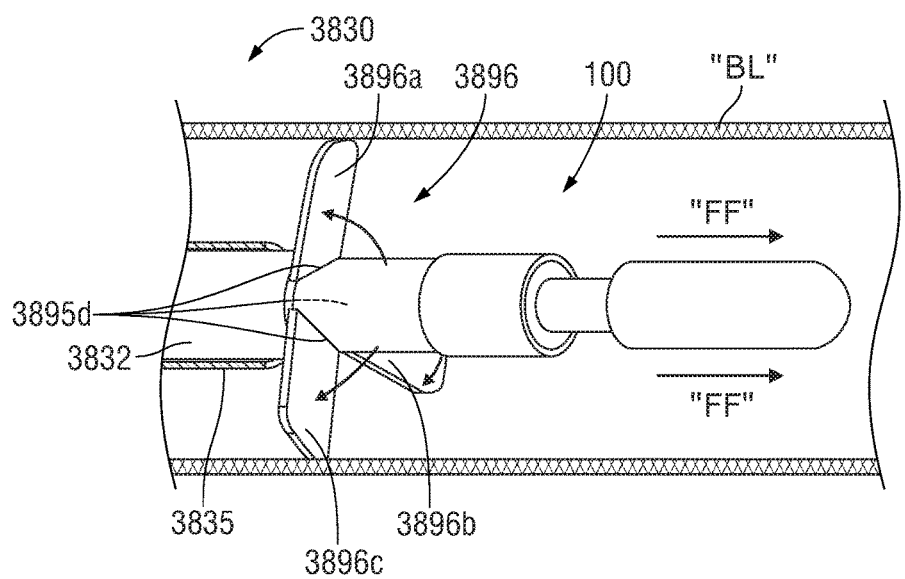

FIGS. 38A and 38B illustrate a paddle centering device 3896 according to some embodiments of the present disclosure. Paddle centering device 3896 includes first, second, and third paddles 3896a-3896c fixed to a portion of the flexible microwave catheter 3830. Paddles 3896a-3896c may be fixed by a hinge-like attachment 3996d that pivotally attaches and/or hingedly attaches each paddle 3896a-3896c to the flexible microwave catheter 3850.

In FIG. 38A, the paddles 3896a-3696c of the paddle centering device 3896 are constrained within the outer sheath 3835 of the flexible microwave catheter 3830. In the constrained condition, the paddles 3896a-3896c are folded inward and positioned adjacent the flexible coaxial cable 3832.

In FIG. 38B, the flexible coaxial cable 3832 and paddles 3896a-3896c are shown deployed from the outer sheath 3835 of the flexible microwave catheter 3830. Paddles 3896a-3896c are opened by moving each paddle about the hinge-like attachment. In the open position paddles 3896a-3896c are prevented from over-extending by a paddle stop (e.g., outer sheath 3835) and/or motion is limited by the hinge-like connection 3896d.

Paddles 3896a-3896c may articulate between a closed condition, as illustrated in FIG. 38A, and an open condition, as illustrated in FIG. 38B. In some embodiments, articulation may be affected by an actuator on the catheter hub 18 (see FIG. 7). In some embodiments, articulation may be affected by the deployment of the flexible coaxial cable 3832 from the outer sheath 3835.

Paddles 3896a-3696c may open in a direction opposite the fluid flow FF, as illustrated in FIG. 38B or paddles 3695a-3695c (see FIGS. 36A-36B) may open in the same direction as the fluid flow FF.

Figure 39A:
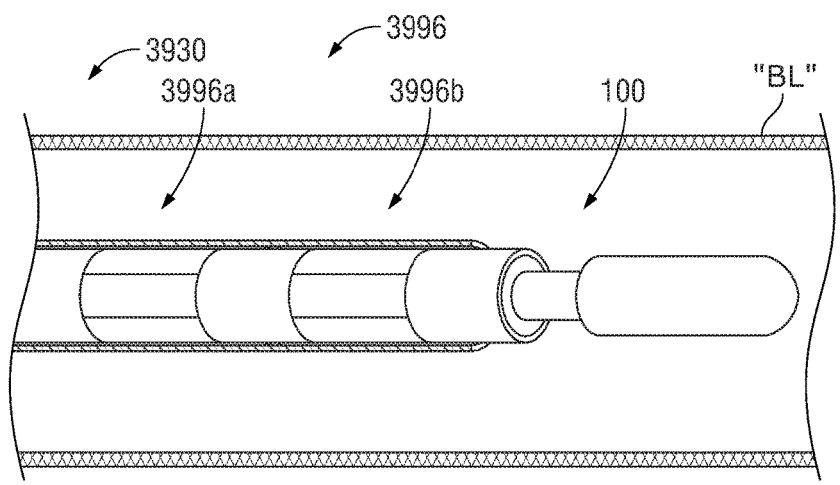
FIGS. 39A and 39B are perspective views of an embodiment of deployable dual paddle centering device in accordance with some embodiments of the present disclosure.
Figure 39B:
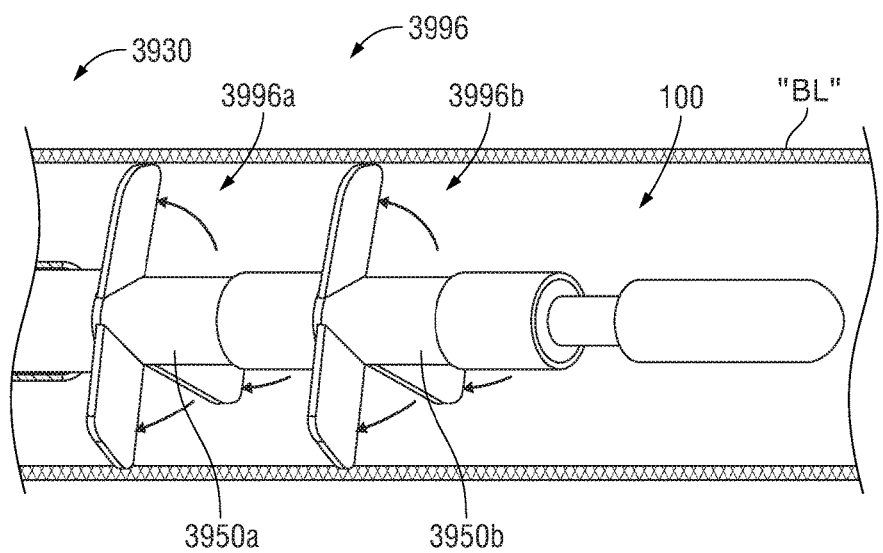

FIGS. 39A and 39B illustrate a dual paddle centering device 3996 according to some embodiments of the present disclosure. Dual paddle centering device 3996 includes a proximal paddle centering device 3996a and a distal paddle centering device 3996b. Proximal paddle centering device 3996a is positioned on the flexible microwave catheter 3930 proximal the first feed gap 3950a. Distal paddle centering device 3996b is positioned on the flexible microwave catheter 3930 between the first feed gap 3950a and the second feed gap 3950b. Proximal paddle centering device 3996a and a distal paddle centering device 3996*b* center the first feed gap 3950*a* and second feed gap 3950*b* in the body lumen BL.

Figure 40A:
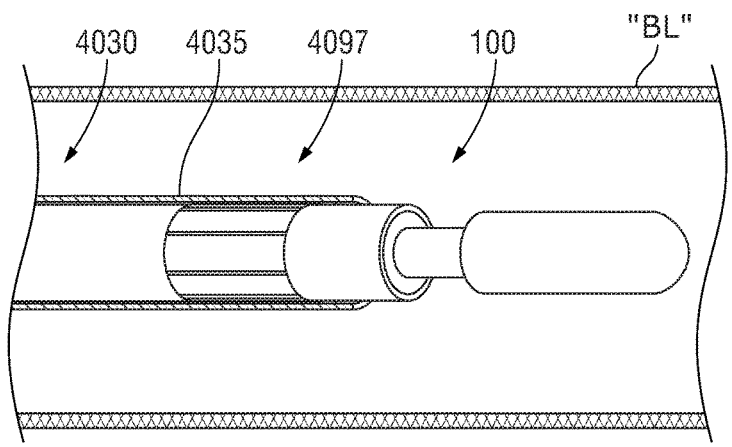
FIGS. 40A and 40B are perspective views of an embodiment of a deployable centering device with a plurality of tines in accordance with some embodiments of the present disclosure.
Figure 40B:
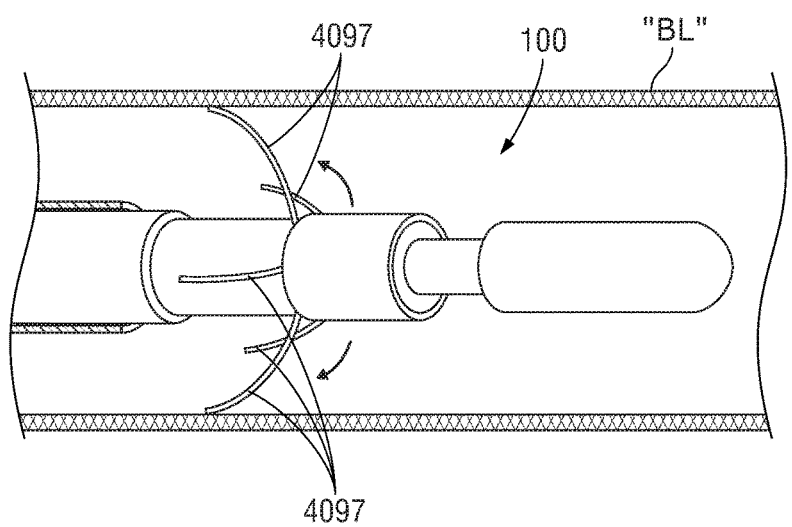

FIGS. 40A and 40B illustrate a deployable centering device that centers the distal radiating portion 100 of a flexible microwave catheter 4030 with a plurality of tines 4097. In an undeployed condition, as illustrated in FIG. 40A, the tines are restrained within the outer sheath 4035 of the flexible microwave catheter 4030. Outer sheath 4035 may retract proximally thereby deploying the radiating portion 100 and tines 4097 from the outer sheath 4035. Alternatively, radiating portion 100 and tines 4097 may deploy distally from the outer sheath 4035. In a deployed condition, as illustrated in FIG. 40B, the tines are attached to, and extend radially outward from, the flexible microwave catheter thereby centering the radiating portion in the renal artery RA.

Figure 41A:
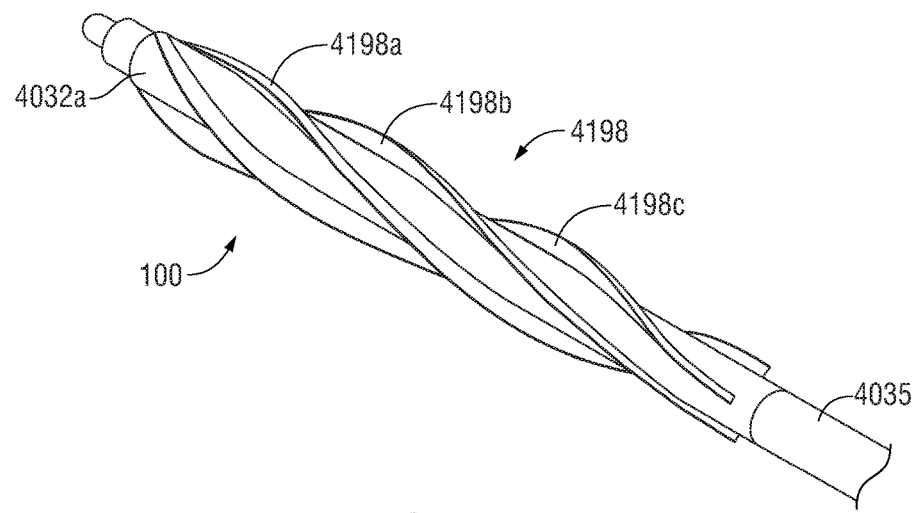
FIGS. 41A and 41B are perspective views of an embodiment of a helical centering devices in accordance with some embodiments of the present disclosure.

FIG. 41A illustrates a helical centering device 4198 that may be used to center the distal radiating portion 100 of a flexible microwave catheter 4030. Helical centering device 4198 includes a plurality of helical ribs 4198*a*-4198*c* that each connect to the outer surface of a distal end of the flexible microwave catheter 4130*a*. In some embodiments, the helical ribs 4198*a*-4198*c* are attached to the outer surface of the flexible coaxial cable 4032*a*. In an undeployed condition, the helical ribs 4198*a*-4198*c* are compressed between the flexible coaxial cable 4032*a* and the inner surface of the outer sheath 4035. As the helical centering devices are deployed from the outer sheath 4025, each of the helical ribs 4198*a*-4198*c* extends radially from the flexible coaxial cable 4032*a* thereby centering the radiating portion 100 within a body lumen.

Figure 41B:
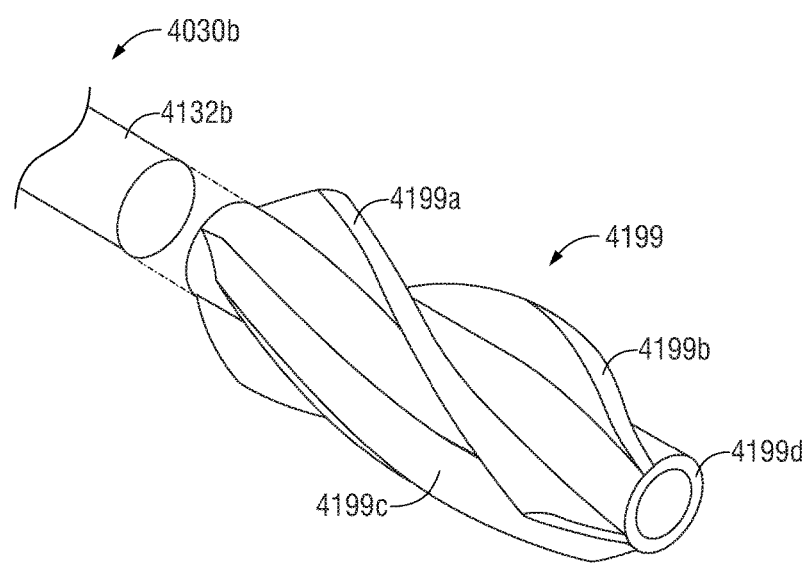

FIG. 41B illustrates a helical centering device 4199 configured to insert over the distal portion of a flexible microwave catheter according to embodiments of the present disclosure. Helical ribs 4199*a*-4199*c* attach to the outer surface of a helical sleeve 4199*d* and the helical sleeve is configured to slidably engage the distal portion of a flexible microwave catheter.

Figure 44:
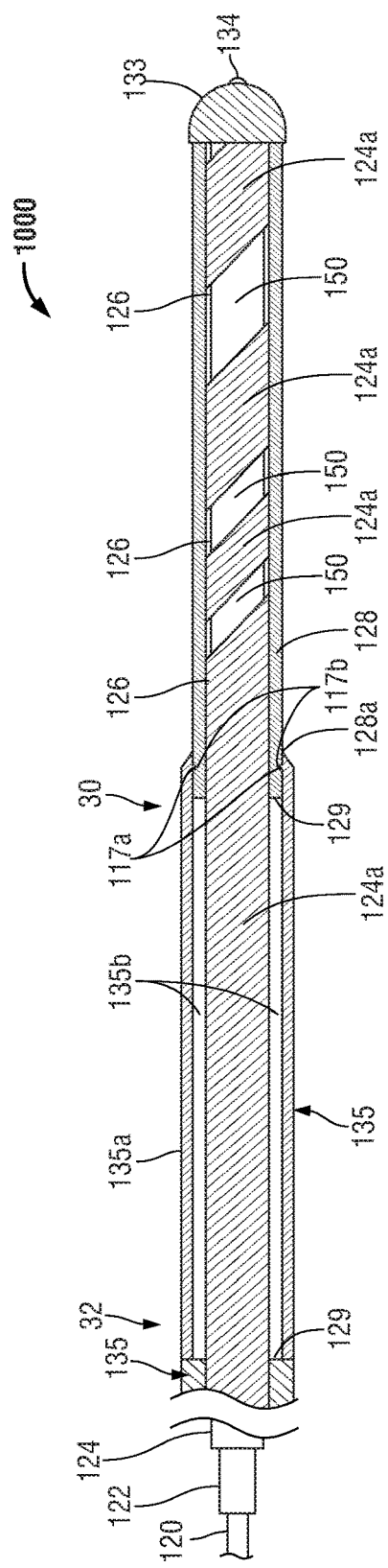
FIG. 44 is a side view of the distal portion of the FIG. 7 embodiment of a microwave energy radiating device having a portion of the outer sheath removed and having a configurable portion in a fully deployed position.

FIGS. 42-44 illustrate a flexible microwave catheter 30 including an outer sheath 135 that forms the outer layer of the flexible microwave catheter 30 and a flexible coaxial cable 32 that slidably engages the inner surface of the outer sheath 135. The proximal portion of the outer sheath 135 includes a first inner diameter D1 that accommodates the outer diameter of the outer conductor 124. A distal-most portion of the outer sheath 135 forms a sliding hub 135*a* that accommodates the radiating portion 100 of the flexible coaxial cable 32. Sliding hub 135*a* includes a second inner diameter D2 that accommodates the outer diameter of the outer dielectric insulating layer 128, wherein the first inner diameter D1 of the outer sheath 135 is less than the second inner diameter D2 of the sliding hub 135*a*. As such, a mechanical stop 129 is formed by the transition of the outer sheath 135 between the first inner diameter D1 and the second inner diameter D2.

In some embodiments, sliding hub 135*a* is less flexible than the proximal portion of the flexible microwave catheter 30. In some embodiments, sliding hub 135*a* is rigid. Flexible microwave catheter 30 may also include a guidance system (not explicitly shown) for manipulating the angle between a proximal, more flexible portion of the flexible microwave catheter 30 and a distal, less-flexible and/or rigid, portion of the flexible microwave catheter (e.g., sliding hub 135*a*).

An outer surface of the outer sheath 135 may include a dielectric coating. In one embodiment, the dielectric coating is a chemically vapor deposited polymer such as the coating sold and manufactured by Parylene Coating Services of Katy, Tex., under the trade name Parylene™. In another embodiment, the dielectric coating includes one or more blood clot reducing properties or components.

FIGS. 42, 43 and 44 illustrate the flexible coaxial cable 32 and the radiating portion 100 on the distal end thereof positioned in various positions, e.g., positioned in a fully retracted position (see FIG. 42), in a partially deployed position (see FIG. 43), and in a fully deployed position (see FIG. 44).

Turning now to FIG. 42, the radiating portion 100 is fully retracted within the sliding hub 135*a* of the outer sheath 135. In a fully retracted condition the proximal end of the outer dielectric insulating layer 128 abuts the mechanical stop 129 of the outer sheath 135 thereby preventing further retraction of the flexible coaxial cable 32 within the outer sheath 135. The proximal end of outer dielectric insulating layer 128 may engage the mechanical stop 129 wherein the engaging surface further prevents retraction of the flexible coaxial cable 32 within the outer sheath 135.

Cap 133 abuts the distal end of the outer sheath 135 and forms a smooth transition between the outer surface of the outer sheath 135 and the outer surface of the cap 133. Cap 133 and outer sheath 135 may be joined together by mechanical engagement, an interference fit, or by soldering, brazing, adhesive and/or laser welding, thereby preventing unintended separation (e.g. deployment) between the cap 133 and outer sheath 135. Cap 133 may prevent further retraction of the flexible coaxial cable 32 within the outer sheath 135. While the embodiments illustrated herein illustrate a blunt distal end that enables the flexible microwave catheter 30 to benignly follow a guiding lumen, in other embodiments, the cap may include a sharpened tip configured for percutaneous insertion into tissue.

In use, a clinician inserts the flexible microwave catheter 30 (e.g., radiating portion 100) into a patient through a channel and maneuvers the flexible microwave catheter 30 to a desired position with the patient. The channel may be a naturally formed body channel and/or lumen (e.g. artery vein, esophagus, bronchial, anus, vagina, urethra, and so forth), a lumen inserted in a naturally formed body channel, a cannula, a shaft or any other suitable insertion needle, device, guide, or system.

During an insertion step, the radiating portion 100 is housed in the sliding hub 135*a* of the outer sheath 135. Sliding hub 135*a* engages outer conductor 124 and prevents any unintended release of energy to patient tissue.

Cap 133 may electrically engage outer sheath 135 thereby forming an electrical pathway (e.g., electrical short) between the inner conductor 120 and the outer conductor 124 via a portion of the outer sheath 135. In a fully retracted position, as illustrated in FIG. 42, the entire radiating portion 100 is contained within the outer sheath and cap 133 thereby minimizing or eliminating, discharge of electrosurgical energy therefrom.

Turning now to FIG. 43, distally advancing the flexible coaxial cable 32 within the outer sheath 135 of the flexible microwave catheter 30 deploys the radiating portion 100 from the sliding hub 135*a*. The length of the radiating portion 100 deployed from the sliding hub 135*a* is selectable by the clinician.

With reference to FIGS. 7, 8C and 42-44, at least a portion of the flexible coaxial cable 32 connects to the actuator 15, 815 in the catheter hub 18. Actuation of the actuator 15, 815 moves the flexible coaxial cable 32 and advances and retracts the flexible coaxial cable 32 within the outer sheath 35. Actuator 15, 815 may be actuated to any desirable position along the actuator slot 15a. The position of the actuator 15, 815 in the actuator slot 15a is related to the position of the radiating portion 100 in the sliding hub 135a and related to the section of the radiating portion 100 that deploys from the sliding hub 135a.

Lock mechanism 817 may be integrated into the body 845a, 854b of the adjustable fluid coupler 845. In some embodiments, the most-proximal position of the lock mechanism 817 includes a lock position that locks the actuator 15, 815 in position to prevent accidental deployment of the radiating portion 100 while positioning the flexible microwave catheter 30 in a guiding lumen. In some embodiments, the lock mechanism 817 and/or the actuator 15, 815 includes a tensioning mechanism, such as a spring (not explicitly shown) that provides a proximal bias on the flexible coaxial cable 32 when the actuator 15, 815 is in the lock position. In some embodiments, the lock position of the actuator 15, 815 includes a take-up mechanism that compensates for any length changes between the flexible coaxial cable 32 and the outer sheath due 35 to bending and/or turning of the outer sheath 35 and flexible coaxial cable 32 while positioning the flexible microwave catheter 30 in a guiding lumen. In some embodiments, actuator 15, 815 includes a lock mechanism 817, a tensioning mechanism, a take-up mechanism or any combination thereof. For example, actuator 15, 815 may include a raised portion 817a that mates with a receiver portion 817b formed on the fluid coupler body 845a and the receiver portion 817b provides a plurality of longitudinal positions to receive the raised portion 817a along its length. Actuator 15, 815 may further include a biasing mechanism, such as a spring or elastic member, or any other suitable tensioning mechanism and/or take-up mechanism.

FIG. 44 illustrates a cross-sectional view of the distal portion of the flexible microwave catheter 30 with the radiating portion fully deployed from the sliding hub 135a. Proximal portion 128a of the outer dielectric insulating layer 128 remains housed within the sliding hub 135a in the fully deployed position. Proximal portion 128a of the outer dielectric insulation layer 128 maintains engagement with the sliding hub 135a thereby facilitating the subsequent retraction of the radiating portion 100 within the sliding hub 135a (see FIGS. 42 and 43). Proximal portion 128a may form a fluid-tight seal 121a with the sliding hub 135a. Fluid-tight seal 121a may prevent body fluid from entering the sliding hub 135a and filling the void 135b within the sliding hub 135a formed by deploying the radiating portion 100.

The transitional dielectric 126 may have dielectric properties related to the dielectric properties of the outer dielectric insulating layer 128. In some embodiments, a dielectric gradient is formed between the transitional dielectric 126, the outer dielectric insulating layer 128 and the anatomical structures with which the radiating portion 100 may be used, e.g., the renal artery or other body lumen/body structure).

The outer surface of the outer dielectric insulating layer 128 and the inner surface of the sliding hub 135a may include interfacing surfaces 117a, 117b that provide a mechanical stop thus preventing the proximal portion 128a of the outer dielectric insulating layer 128 from advancing from the sliding hub 135a. For example, in one embodiment, the inner surface of the sliding hub 135a includes a radially inward protruding tab 117a. At a fully deployed position the radially inward protruding tab 117a engages a mechanical stop 117b formed in the dielectric insulating layer 128 thereby preventing further distal deployment of the radiating portion 100 from sliding hub 135a.

In some embodiments, a choke or balun short (not explicitly shown) is positioned longitudinally proximal to the formation of the helical feed gap 50 and may be fixed to the outer conductor 124 and/or the outer sheath 135. The balun may be formed from a short conductive (e.g., metallic) ring having an inner diameter dimensioned to accept the outer conductor 124 (or the outer sheath 135). Alternatively, the balun may be formed on the inner surface of the outer sheath 135. The balun is electrically bonded (e.g., soldered and/or electrically connected by a suitable conductor) to the outer conductor 124. This balun affects a radiofrequency short which, in turn, may optimize, control, focus, and/or direct the general proximal radiating pattern of the radiating portion antenna, e.g., reduce the propagation of denervation energy beyond the proximal end of the antenna radiating portion and/or the balun.

The balun assembly may include a balun dielectric sleeve, which may be formed from extruded polytetrafluoroethylene (PTFE, e.g., Teflon®). The balun dielectric may be positioned over the radiating portion 100 of the flexible microwave catheter 30 and mated to the balun ring. A length of heat shrink tubing (not explicitly shown), having a conductive material on a surface thereof, preferably an inner surface, may be positioned over the PTFE sleeve to improve the performance of the balun and thus, improve the radiating pattern of denervation energy.

In some embodiments, as discussed in detail hereinbelow and illustrated in FIGS. 42-57, a flexible microwave catheter in accordance with the present disclosure includes a radiating portion having a spiral configuration, wherein the outer conductor of the radiating portion is exposed in a spiral pattern. The width of the spiral opening may optionally be tapered, increasing in width as the spiral winds distally along the radiating portion, in order to radiate energy evenly along the length thereof (see FIGS. 42-49 and 54-57). A spiral sensor lumen or conductor may be interspersed within the spiral feedpoint to operatively couple a sensor disposed at or near the distal region of the probe to a generator or other apparatus located proximally of the probe.

Any number of baskets, centering devices or expandable members, as discussed hereinabove, may be utilized with this spiral structure to selectively ablate tissue in a radial direction away from the centralized structure. This would allow for a procedure which normally requires multiple placements of an ablation device to be simplified by necessitating only one placement providing multiple selectively directed radiating elements. The user may choose to deploy any number of the baskets, centering devices or expandable members, while leaving others collapsed and thus deactivated due to the conductive sheath covering the feed gap.

The deployable structure illustrated in FIGS. 42-44 and described herein, may also be utilized to deploy any of the structures and radiating portion 100 described herein.

As discussed hereinabove with respect to FIGS. 42-44, the radiating portion 100 includes a shielding outer conductor 124a that exposes the inner conductor 120 thereby forming a helical feed gap 50 (e.g., feed point). In one embodiment, the shielding outer conductor 124a is formed by removing a portion of the outer conductor 124 at the helical feed gap 50. The shielding outer conductor 124a that remains on the inner conductor 120 is wrapped helically around the longitudinal axis of the inner conductor 120. A helical and/or spiral feed gap provides uniform distribution of energy along the axial length of the radiation section as well as an ideal impedance match to the coaxial waveguide impedance thereby reducing unwanted heating along the flexible coaxial feedline 32.

In some embodiments, prior to use (e.g., during manufacturing) the outer conductor 124 and inner dielectric insulator are removed from the inner conductor 120 in the radiating portion 100 and a shielding outer conductor 124a and shielding dielectric (not explicitly shown) are positioned on the exposed inner conductor. The shielding outer conductor 124a is wrapped helically around the longitudinal axis of the inner conductor 120. The proximal portion of the shielding outer conductor 124a is electrically connected to the distal portion of the outer conductor 124. The distal portion of the shielding outer conductor 124a is electrically connected to the cap 133. The cap shorts the shielding outer conductor 124a to the inner conductor 120.

Cooling fluid from the fluid cooling system 40 (see FIG. 7) may flow through fluid lumens formed in the shielding outer conductor 124a and connected to the inflow fluid passageway 44a and outflow fluid passageway 44b in the flexible microwave catheter 30 thereby proving fluid pathways for cooling fluid to flow to and from the distal end of the radiating portion 100.

As discussed hereinabove, a transitional dielectric 126 may be disposed in the helical feed gap 150 and may generally and/or geometrically correspond to the dimensions of the helical feed gap 150. The transitional dielectric 126 and the shielding dielectric (not explicitly shown) may be formed from similar materials with similar dielectric properties. In some embodiments, the transitional dielectric 126 and the shielding dielectric may have different dielectric properties. In some embodiments, a single dielectric layer includes the transitional dielectric 126 and the shielding dielectric includes a first geometrical portion having dielectric properties corresponding to the transitional dielectric 126 and a second geometrical portion having dielectric properties corresponding to the shielding dielectric.

As discussed hereinabove, the feed gap 150 is defined by the void formed from the removal of a portion of the outer conductor 124. Similarly, the helical feed gap 150 is defined by the void formed between adjacent windings of the helically wrapped shielding outer conductor 124a (e.g., helically wrapped about the longitudinal axis of the inner conductor 120). The dimensions of the helical feed gap 150 are related to properties and the position of the shielding outer conductor 124a. The helical feed gap 150 may also be defined by the portion of the inner conductor not helically wrapped by the shielding outer conductor 124a. As such, defining the dimensional properties and position of the shielding outer conductor 124c necessarily defines the helical feed gap 150 that varies along the longitudinal length of the radiating portion 100. In one embodiment, the position of the helical feed gap 150 changes circumferentially along the length thereof. In some embodiments, the pitch of the helix (e.g., the width of one complete helix turn, measured parallel to the axis of the helix) varies along the longitudinal length of the radiating portion 100. In some embodiments, the pitch may vary due to a change in the helix angle (e.g., the angle between any helix and an axial line formed perpendicular to the inner conductor). In some embodiments, the pitch may vary due to a change in the width of the helical feed gap 150 (e.g., a varying thickness of the helical feed gap 150 along the longitudinal length thereof). In some embodiments, the pitch may vary due to a change in the helix angle and a change in the width of the helical feed gap 150.

In use, the energy transmitted to tissue by the radiating portion 100 is related to the area and position of the helical feed gap 150. As illustrated in FIGS. 42-44, the area of the helical feed gap 150 increases as the helix winds distally, transitioning from a narrow helical feed gap 150 on the proximal end to a wide helical feed gap 150 on the distal end of the radiating portion 100. The change in area (e.g., increase in area as the helix distally winds) translates in a low coupling factor on the proximal end and a high coupling factor on the distal end. On the proximal end of the radiating portion 100 the coupling factor is 1% and the coupling factor increases in an exponential manner to 100% at the distal end.

Figure 45:
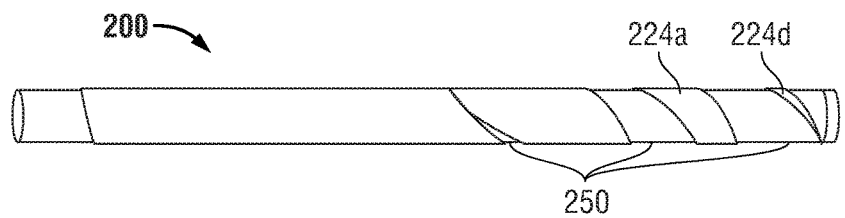
FIG. 45 is a side, perspective view of an embodiment of a microwave energy radiating device having a non-linear wrap pattern in accordance with some embodiments of the present disclosure.
Figure 46:
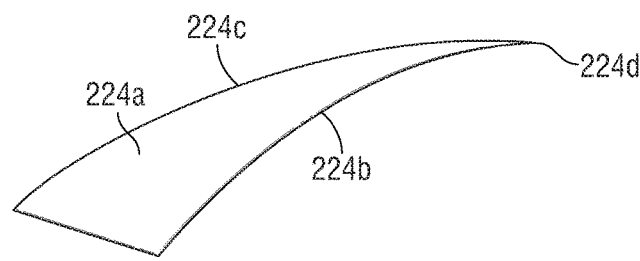
FIG. 46 is a top, perspective view of the outer conductor of the FIG. 45 embodiment having been removed therefrom.

FIGS. 45 and 46 illustrate another embodiment of a non-linear wrap pattern that forms a radiating portion 200 that may be incorporated into any flexible microwave catheter 30 according to some embodiments of the present disclosure. The area of the helical feed gap 250 increases as the helix winds distally with the proximal end providing a narrow feed gap 250 and the distal portion being more substantially exposed. The non-linear change in the area of the helical feed gap 250 at the proximal end of the radiating portion 200 and the area of the helical feed gap 250 at the distal end of the radiating portion 200 is due to the geometry of the shielding outer conductor 224a.

As illustrated in FIG. 46, the shielding outer conductor 224a includes a proximal first non-linear edge 224b, a second distal non-linear edge 224c wherein the first non-linear edge 224b and the second non-linear edge 224c terminate on the distal end 224d thereby forming a substantially pointed distal end 224d.

Figure 47:
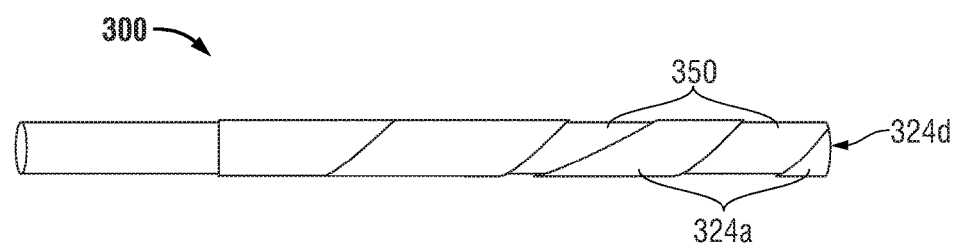
FIG. 47 is a side, perspective view of an embodiment of a microwave energy radiating device having a non-linear wrap pattern according to another embodiment of the present disclosure.
Figure 48:
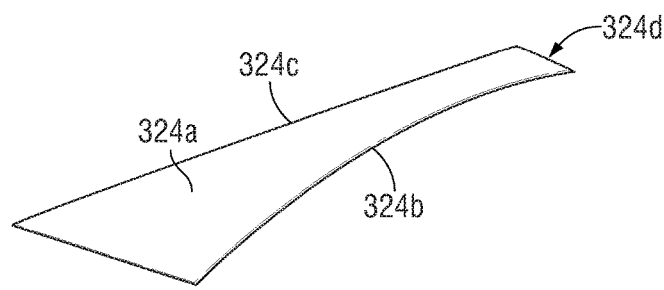
FIG. 48 is a top, perspective view of the outer cover of the FIG. 47 embodiment having been removed therefrom.

FIGS. 47 and 48 illustrate yet another embodiment of a non-linear wrap pattern that forms a radiating portion 300 that may be incorporated into any flexible microwave catheter 30 of the present disclosure. The area of the helical feed gap 350 increases as the helix travels distally with the proximal end providing a narrow feed gap and the distal portion being substantially exposed. The non-linear change in the area of the helical feed gap 350 at the proximal end of the radiating portion 300 and the area of the helical feed gap 350 at the distal end of the radiating portion 300 is due to the geometry of the shielding outer conductor 324a.

As illustrated in FIG. 48, the shielding outer conductor 324a includes a proximal first non-linear edge 324b, and a second distal linear edge 324c that terminates on the distal end thereof. The distal end forms a flat distal edge 324d configured to align with the distal end of the inner conductor (not explicitly shown).

Figure 49:
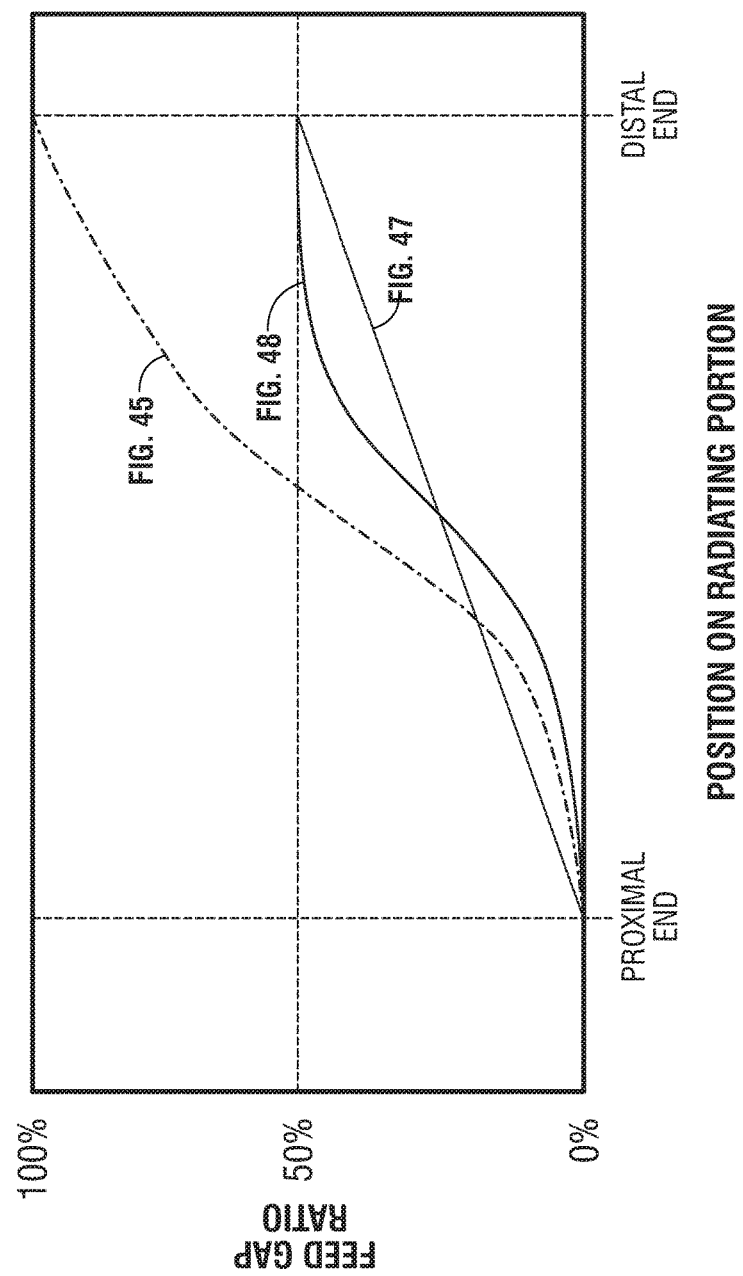
FIG. 49 is a graph illustrating a ratio of a radiating portion to a non-radiating portion of the microwave energy radiating devices of FIGS. 44, 45 and 47.

One measure of the varying helical feed gap 150 is the feed gap ratio, defined herein as the ratio between the cross-sectional circumference of the helical feed gap 150 and the cross-sectional circumference of the shielding outer conductor 124a. FIG. 49 is a graph illustrating the feed gap ratio along the longitudinal length of the radiation portion 1000, 200, 300 of the respective embodiments illustrated in FIGS. 44, 45 and 47. The feed gap ratio of radiating portion 1000 in FIG. 44 varies between 0% and 50% and varies linearly along the longitudinal length between the proximal end and the distal end of the radiating portion 1000. The feed gap ratio of radiation portion 200 in FIG. 45 varies between 0% and 100% and varies non-linearly along the longitudinal length between the proximal end and the distal end of the radiating portion 300. The feed gap ratio of radiation portion 300 in FIG. 47 varies between 0% and 100% and varies non-linearly along the longitudinal length between the proximal end and the distal end of the radiating portion 300. Other geometries that may be used include an exponential taper, a triangular taper and a Klopfenstein logarithmic taper from a stepped Chebyshev transformer where the sections increase to infinite (e.g., analogous to a Taylor distribution).

As discussed hereinabove with respect to FIGS. 6A-6B and 8A-8C, the flexible microwave catheter 30 may include a tubular inflow lumen 37 positioned coaxially between the inner flexible coaxial cable 32 and the outer sheath 135. A clearance between the outer diameter of the flexible coaxial cable 32 and the inner diameter of the inflow lumen 37 defines an inflow fluid passageway 44a. A clearance between the outer diameter of the inflow lumen 37 and an inner diameter of the outer sheath 135 defines an outflow fluid passageway 44b. During use, a coolant, e.g., carbon dioxide, air, saline, water, or other coolant media may be supplied to the radiating portion 100 by the inflow fluid passageway 44a and evacuated from the radiating portion 100 by the outflow fluid passageway 44b.

In some embodiments, the inflow fluid passageway 44a that supplies coolant and is the inner-most fluid conduit and the outflow fluid passageway 44b that evacuates coolant is the outer-most fluid conduit. In other embodiments, the direction of fluid flow may be opposite. One or more longitudinally-oriented fins or struts (not explicitly shown) may be positioned within the inflow fluid pathway and/or the outflow fluid pathway to support and control the position of the inflow lumen with respect to the outer sheath 135 and to support and control the position of the flexible coaxial cable 32 with respect to the inflow lumen 37.

Figure 50:
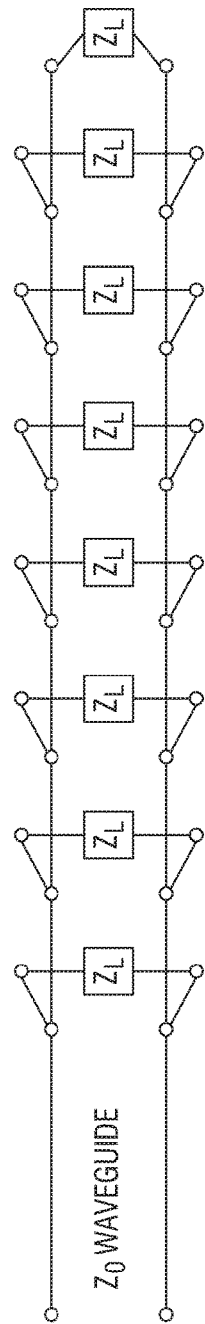
FIG. 50 is an electrical circuit diagram of an embodiment of a leaky waveguide according to the present disclosure.

FIG. 50 is an electrical circuit diagram of a leaky waveguide according to another embodiment of the present disclosure. The leaky waveguide includes a network with an impedance of $Z_O$ wherein all energy is radiated or dissipated in the leaky waveguide. Each $Z_L$ is composed of a radiation resistance, reactive impedance and loss resistance wherein:

$$Z_L = R_R - iR_i + R_1 \quad (1)$$

Although represented by a lumped element, the $Z_L$ components may be a distributed network. As illustrated in FIG. 51, each $Z_L$ component may represent one of the five slots S1-S5 in a coaxial cable.

Figure 52:
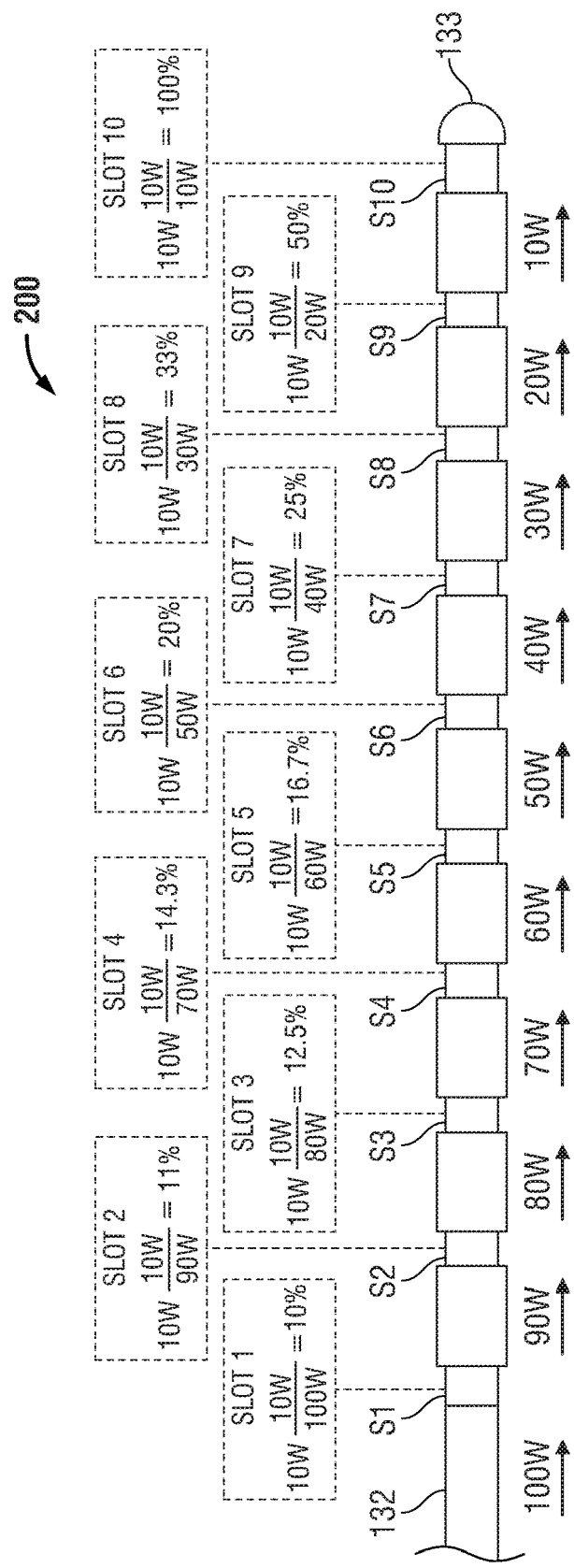
FIG. 52 is an electrical diagram of an embodiment of a ten-slot waveguide in accordance with the present disclosure illustrating the available energy for each slot and the percentage of the available energy transmitted from each slot.

Another waveguide according to the present disclosure may include any number of slots. FIG. 52 illustrates an embodiment having a radiating portion 200 utilizing ten (10) slots. To provide a uniform radiating pattern along the length of the radiating portion, each of the ten (10) slots must radiate approximately 10% of the total available energy provided to the waveguide $Z_O$. Since each slot radiates a portion of the total available energy, the remaining energy available to each subsequent slot is less than the energy provided to the previous slot. As such, a uniform radiating pattern requires each distally positioned slot to radiate a higher percentage of the remaining available energy than each proximally positioned (e.g., prior) slot.

In the example embodiment illustrated in FIG. 52, 100 Watts of energy is provided to the leaky waveguide 200, therefore, slot 1 must transmit about 10% of the total energy provided thereto (e.g., 10% of 100 Watts=10 Watts). Slot 2 is provided with about 90 Watts (100 Watts minus the 10 Watts transmitted by slot 1), therefore, slot 2 must transmit about 11% of the total energy provided thereto (e.g., 11% of 90 Watts=10 Watts). Slot 3 is provided with about 80 Watts (100 W minus the 20 Watts transmitted by slots 1-2), therefore, slot 3 must transmit about 12.5% of the total energy provided thereto (e.g., 12.5% of 80 Watts=10 Watts). Slot 4 is provided with about 70 Watts (100 Watts minus 30 Watts transmitted by slots 1-3), therefore, slot 4 must transmit about 14.3% of the total energy provided thereto (e.g., 14.3% of 70 Watts=10 Watts). Slot 4 is provided with about 70 Watts (100 Watts minus 30 Watts transmitted by slots 1-3), therefore, slot 4 must transmit about 14.3% of the total energy provided thereto (e.g., 14.3% of 70 Watts=10 Watts). Slot 5 is provided with about 60 Watts (100 Watts minus 40 Watts transmitted by slots 1-4), therefore, slot 5 must transmit about 16.7% of the total energy provided thereto (e.g., 16.7% of 60 Watts=10 Watts). Slot 6 is provided with about 50 Watts (100 Watts minus 50 Watts transmitted by slots 1-5), therefore, slot 6 must transmit about 20% of the total energy provided thereto (e.g., 20% of 50 Watts=10 Watts). Slot 7 is provided with about 40 Watts (100 Watts minus 60 Watts transmitted by slots 1-6), therefore, slot 7 must transmit about 25% of the total energy provided thereto (e.g., 25% of 40 Watts=10 Watts). Slot 8 is provided with about 30 Watts (100 Watts minus 70 Watts transmitted by slots 1-7), therefore, slot 8 must transmit about 33% of the total energy provided thereto (e.g., 33% of 30 Watts=10 Watts). Slot 9 is provided with about 20 Watts (100 Watts minus 80 Watts transmitted by slots 1-8), therefore, slot 9 must transmit about 50% of the total energy provided thereto (e.g., 50% of 20 Watts=10 Watts). Slot 10 is provided with about 10 Watts (100 Watts minus 90 Watts transmitted by slots 1-9), therefore, slot 10 must transmit about 100% of the total energy provided thereto (e.g., 100% of 10 Watts=10 Watts).

Moving distally along the waveguide, each slot must progressively transmit a higher percentage of energy available to the individual slot. One method of progressively increasing the percentage of energy transmitted from each slot is to vary the width of each slot as the waveguide progresses distally (increasing the width of each slot moving distally). FIG. 53 illustrates a waveguide wherein each slot progressively increases in width. In some embodiments the increase in width provides an improvement in efficiency thereby resulting in an increase in the percentage of energy transmitted therefrom. The distal-most slot may be regarded as highly efficient slot capable of radiating the total remaining power therefrom (e.g., radiating 100% of the power provided thereto).

The energy radiated from each of the slots is related to the desired efficiency of the slot, the width of the slot and/or the wavelength of the energy provided to waveguide (e.g., each slot). In some embodiments, the width of each slot is related the desired efficiency of the slot. For example, if the desired efficiency of a slot is 20% of the energy provided thereto, the width may be calculated by the microwave signal wavelength and desired efficiency.

In another embodiment, the effective length of the distal-most slot is equal to ½ of the wavelength of microwave signal, and the width of the slots proximal the distal-most slot is related to the desired efficiency of the slots wherein the efficiency of each slot is determined by the energy provided to each individual slot and the desired power output of each slot.

Due to losses in the coaxial waveguide, the amount of energy provided to each slot is equal to the energy provided to the waveguide minus the amount of energy transmitted by the proximal slots and minus any losses in the coaxial cable. As such, the percentage for each progressive slot may be increased and/or the number of slots may be decreased to compensate for the energy losses in the coaxial waveguide.

Using slot 4 in FIG. 52 as an example, and assuming the losses in slots 1-3 to equal 5 Watts, the actual energy provided to slot 4 is 65 Watts (100 Watts minus 30 Watts transmitted by slots 1-3 and less the losses of 5 Watts). Therefore, slot 4 must transmit about 15.4% of the 65 Watts provided to slot 4 (e.g., 15.4% of 65 Watts). As such, losses in the proximal slots may result a reduction in the number of slots in order to provide an even and equal pattern of energy radiation from each slot.

A more distributed approach, as opposed to the segmented approach of individual slots, provides an even and uniform energy distribution pattern. FIG. 54 shows a waveguide wherein the progressively increasing width of each slot, as illustrated in the waveguide of FIG. 53, is arranged as a continuous helical slot 450. In one embodiment, the geometry of the slot (e.g., the helix angle, pitch and slot width) is related to the required efficiency of each section of the helix. In some embodiments, the efficiency of each section of the helix is determined by the energy provided to each section of the helix and the desired power output of each section of the helix. Geometric parameters that may vary include the axial ratio, the number of turns and the width of the feed gap. The helix, which eliminates the individual slots, may also reduce losses generated as a result of having each individual slot.

As the opening widens (e.g., in a proximal to distal direction), due to the change in pitch and/or the change in the helix angle, the slot progressively radiates more energy thereby promoting a uniform energy pattern and resulting in less return loss.

Figure 53:
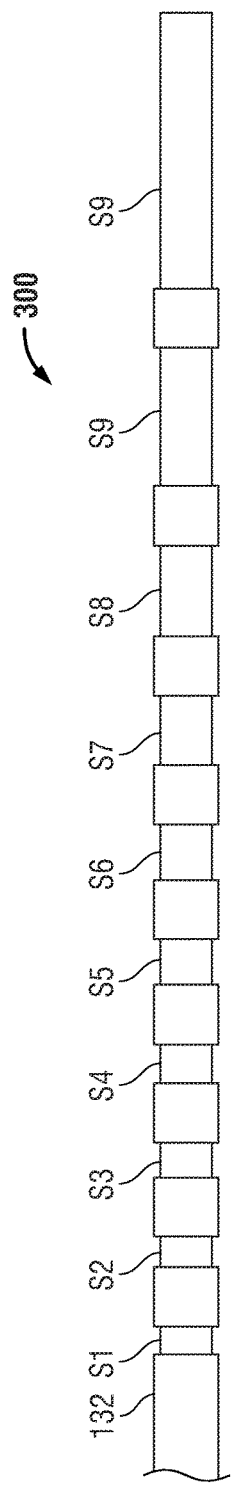
FIG. 53 is a side view of an embodiment of a ten-slot waveguide in accordance with the present disclosure wherein each slot transmits a substantially similar amount of energy.
Figure 54:
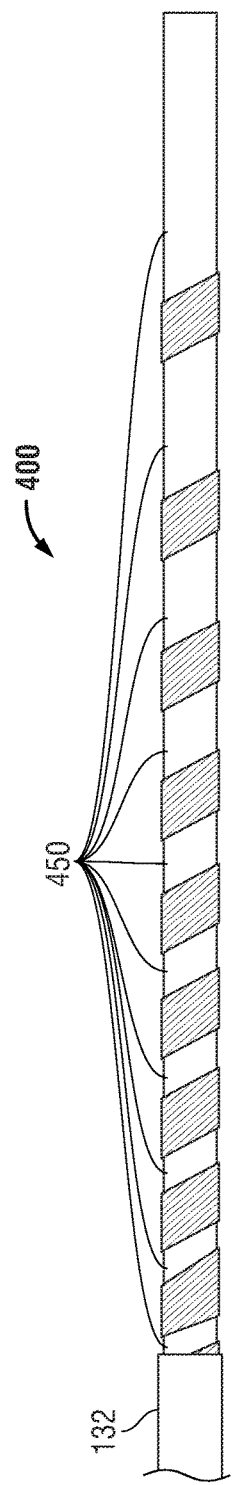
FIG. 54 is a side view of an embodiment of a helix waveguide with ten helix wraps according to embodiments of the present disclosure.
Figure 55:
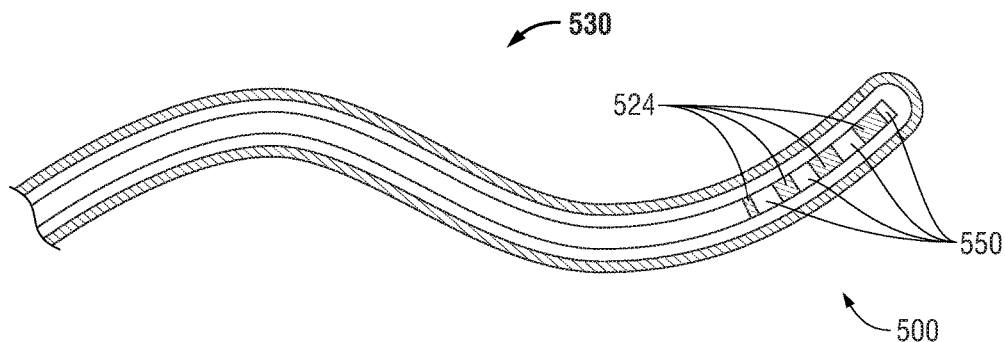
FIG. 55 is a perspective view of a five-slot waveguide according to embodiments of the present disclosure.
Figure 56:
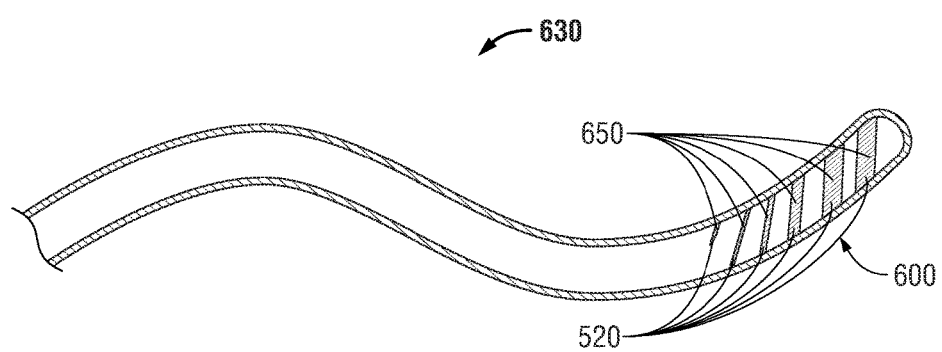
FIG. 56 is a perspective view of a helix waveguide with five helix wraps according to embodiments of the present disclosure.

FIGS. 55 and 56 illustrate flexible microwave catheters 530 and 630 with waveguides 500 and 600 related to the waveguides of FIGS. 53 and 54, respectively. In FIG. 55, the waveguide 500 includes a plurality of progressively spaced slots 550 wherein the width of each distally spaced slot increases to provide the desired power output. In FIG. 56, the waveguide 600 includes a helical feed slot 650 with a varying pitch, slot width and helix angle wherein the progressively increasing slot width, and exposed portion of the radiating inner conductor 520, 620, provides the desired power output along the length of the waveguide 600. The flexible microwave catheters 530 and 630 may include a cooling fluid arrangement as discussed hereinabove.

Figure 57:
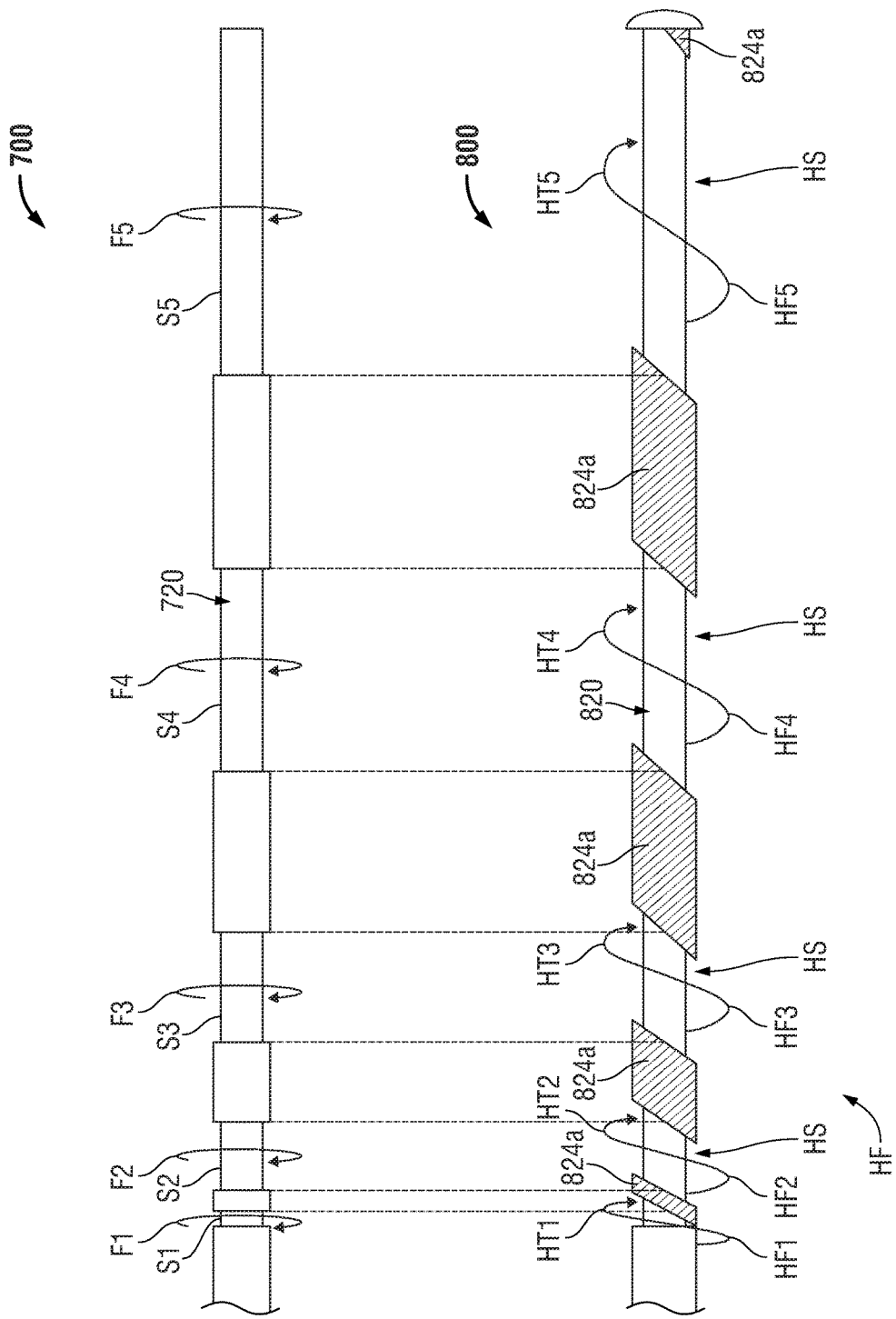
FIG. 57 is a side-by-side comparison of a five-slot waveguide and a helix waveguide with five helix wraps according to embodiments of the present disclosure.

FIG. 57 illustrates waveguides 700 and 800, wherein slotted waveguide 700 includes five (5) slots and helix waveguide 800 includes five turns of a helix. Waveguides 700 and 800 are arranged to provide a comparison/correlation between the slots S1-S5 of the slotted waveguide 700 and the respective helix turns HT1-HT5 of the helix waveguide. Each helix turn HT1-HT5 includes a corresponding position on the helix wherein the width of the helix is related to the width of the corresponding slot S1-S5 and the exposed inner conductor 720. As discussed hereinabove, the shape and position of the helix slot HS is related to, and defined by, the void between the individual wraps of the shielding outer conductor 824a on the inner conductor 820.

As further illustrated in FIG. 57, the slotted waveguide 700 includes five radiation slots S1-S5 with each slot S1-S5 exposing a portion of the inner conductor 720. Slots S1-S5 generate a corresponding electromagnetic field F1-F5, respectively. The electromagnetic fields F1-F5 are distinct and independently generated, although at least a portion of one or more of the electromagnetic fields F1-F5 may overlap and/or combine with an adjacent electromagnetic field F1-F5.

The helix waveguide 800 generates a helical-electromagnetic field HF that extends along the longitudinal length of the helix waveguide 800. The shape of the helical-electromagnetic field HF is related to the shape of the helix slot HS and related to the varying void formed between the individual wraps of the shielding outer conductor.

The shape of the helical-electromagnetic field HF may be represented as a plurality of inter-connected, helically-shaped electromagnetic fields HF1-HF5 with each of the inter-connected helically-shaped electromagnetic field being related to a corresponding slot S1-S5 on the slotted waveguide 700. The helical-electromagnetic field HF may include a plurality of minimum nodes and a plurality of maximum nodes wherein the magnitude of the helical-electromagnetic field at a minimum node is a relative minimum and the magnitude of the helical-electromagnetic field at a maximum node is a relative maximum. In one embodiment, the number of minimum nodes is related to the number of helix turns. The overall shape of the helical-electromagnetic field HF may dynamically change about the helix. In some embodiments, the number of maximum nodes is related to the number of helix turns.

FIG. 58A is a perspective view of a deflated balloon centering device 5872 having a spiral window 5899 formed therein according to some embodiments of the present disclosure. Balloon centering device 5872 includes a balloon membrane 5872a coated with a conductive layer 5872b. As illustrated in the cut-out portion of FIG. 58A, conductive layer 5872b may be formed on the inner surface of balloon membrane 5772a. Alternatively, in some embodiments, the conductive layer 5872b is formed on the outer surface of the balloon membrane 5872a.

The conductive layer 5872b may be formed by any suitable manner of coating or deposition, including without limitation, thin film deposition, plating, application of conductive ink, foil, and the like. In some embodiments, the conductive layer 5872b is formed from conductive silver ink. The conductive layer 5872b may be formed in a pattern, e.g., a spiral pattern, a lattice pattern, a halftone pattern, a gradient pattern, or any pattern that facilitates the elastic inflation and deflation of the balloon centering device 5872 while maintaining conductivity among and between the elements that form the pattern of the conductive layer 5872b.

Spiral window 5899 includes the balloon membrane 5872a and does not include a conductive layer 5872b. Balloon membrane 5872a in the spiral window 5899 area is formed of a material that is transparent to microwave energy thereby exposing the tissue adjacent the spiral window 5899 to an application of denervation energy. The spiral window 5899 may have a maximum width of about 3-5 mils (0.003"-0.005"). By this arrangement, the conductive layer 5872b forms a Faraday cage structure that improves the radiation pattern and facilitates the delivery of denervation energy to the tissue adjacent the spiral window 5899. In some embodiments, the balloon membrane 5872 may be formed from a non-compliant material to ensure the correct geometer is achieved.

In some embodiments, a balloon centering device 5872 in accordance with the present disclosure may include a conductive layer 5872b disposed at the proximal and distal ends thereof, while having little, or no, conductive material in a conductive layer 5872b along the middle portion, thereby forming a conductive gradient between the proximal end and distal ends, and the middle portion. The balloon centering device 5872 may include conductive patterns arranged in accordance with the heretofore described configuration(s) of mesh structures, wherein the conductive layer 5872 is coated on all but a windowed portion 5899 of the balloon centering device 5872. Some embodiments may include multiple balloon centering devices, a single balloon centering device with multiple windows, a rotatable balloon(s) centering device, and so forth.

Fluid ports 5872c form a plurality of lumens through the balloon centering device 5872. The radial position of the fluid ports 5872c may be positioned radially outward to provide cooling for the anatomical structure. In embodiments, fluid ports 5872c may be positioned radially inward to provide cooling to the radiating portion of the flexible microwave catheter 5830.

Figure 58B:
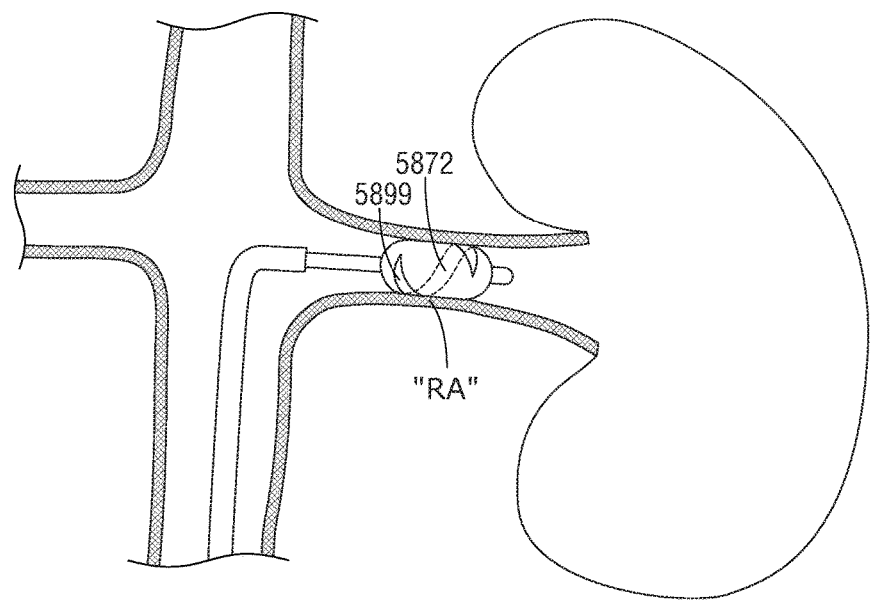
FIG. 58B is a perspective view in partial cross-section of the balloon centering device of FIG. 58A in a fully inflated configuration and positioned in the renal artery via the vascular system.

FIG. 58B is a perspective view of the balloon centering device of FIG. 58A shown fully inflated and positioned within a renal artery RA. The window 5899 extends around about the entire circumference along the longitudinal length of the balloon centering device 5872. When placed in a body lumen, such as the renal artery RA, the energy applied through the window 5899 results in a heating pattern consistent with the shape of the window 5899.

Fully inflated, the spiral window 5899 may radiate energy over 360 degrees along a longitudinal span of about 2 to 3 cm. In other body lumens, the spiral window 5899 may radiate energy over 360 degrees along a longitudinal span of about 3 to 5 cm. In yet other body lumens, the spiral window 5899 may radiate energy over 360 degrees along a longitudinal span of about 5 to 7 cm. In yet other body lumens, the spiral window 5899 may radiate energy over 360 degrees along a longitudinal span of over 7 cm.

Figure 58C:
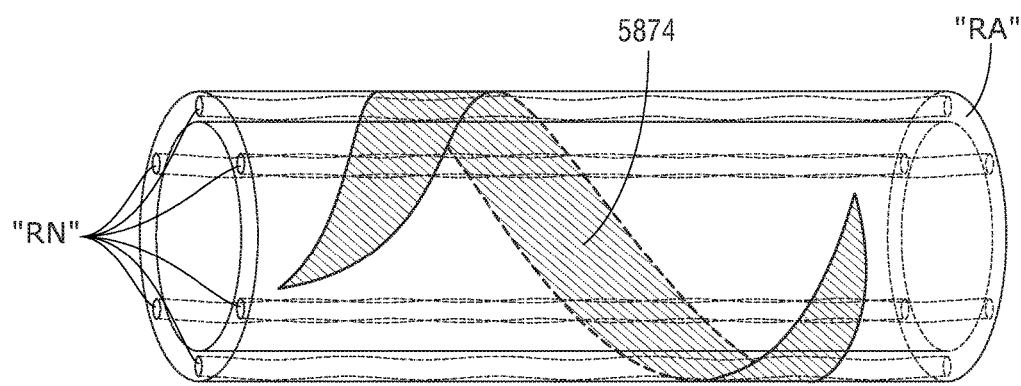
FIG. 58C is a perspective view of a portion of a renal artery after receiving selectively delivered denervation energy from the balloon catheter of FIGS. 58A-58C.

FIG. 58C illustrates a renal artery RA after the application of denervation energy by the device illustrated in FIG. 58A-B. The denervation energy applied to the renal artery RA through the windows 5899 generates a corresponding denervation zone 5874. The 360 degree heating pattern is applied across a portion of the renal artery to derivate the kidney without causing morbidity resulting from vessel wall damage. Other treatment angles that may be utilized include 90 degree heating patterns, 180 degree heating patterns, 180 degree heating patterns and 450 degree heating patterns.

A method for using the embodiments described herein includes the steps of accessing the femoral artery; placing a long sheath for renal artery access into the femoral artery, abdominal aorta and renal artery; placing a flexible microwave catheter 30 according to one embodiment of the present disclosure into the long sheath, and into a portion of the renal artery, delivering microwave energy to the anatomical radiating structure via a flexible coaxial cable, continuing the energy delivery until a sufficient amount of energy has been delivered to damage targeted nerve structures while preserving the critical structure of the renal artery by cooling (e.g. by circulation of blood), and removing the microwave catheter, removing the long sheath, and closing access to the femoral artery. Another step in the method may include the step of monitoring fluid temperature for dangerous temperature elevation via a distally positioned temperature sensor.

Another method for using the embodiments described herein includes the steps of placing a flexible microwave catheter, including one or more embodiments described herein, into the renal artery via an intravascular approach; utilizing a retractable sheath to deploy an electrically conductive mesh (according to an embodiment described herein) about a radiating portion (e.g., feed gap) wherein the conductive mesh enhances microwave energy delivery to the renal nerves (e.g., sympathetic nerves surrounding the renal artery) by generating an anatomical waveguide that resonates microwave signals through tissue. Another step in the method includes providing a location in the electrically conductive mesh having a window characterized by the lack of material thereby generating an ablation region related to the window. Another step in the method may include providing a fluid cooling structure to enhance energy delivery and reduce cable heating of tissues surrounding the access path. Another step may include providing a catheter hub that allows for the flexible coaxial structure to slide longitudinally therethrough.

The described embodiments of the present disclosure are intended to be illustrative rather than restrictive, and are not intended to represent every embodiment of the present disclosure. Further variations of the above-disclosed embodiments and other features and functions, or alternatives thereof, may be made or desirably combined into many other different systems or applications without departing from the spirit or scope of the disclosure as set forth herein and/or in the following claims both literally and in equivalents recognized in law.

What is claimed is:

1. A flexible microwave catheter comprising:
a catheter hub;
an outer sheath extending from the catheter hub, the outer sheath configured to prevent a release of microwave energy therethrough; and
a coaxial feedline disposed within the outer sheath, the coaxial feedline having an inner conductor, an inner dielectric coaxially disposed about the inner conductor, and an outer conductor coaxially disposed about the inner dielectric, wherein the coaxial feedline defines a radiating portion at a distal portion of the coaxial feedline, the radiating portion configured to emit microwave energy; and
wherein the coaxial feedline is slidable within the outer sheath and along a longitudinal axis of the outer sheath such that the radiating portion is selectively deployable from the outer sheath upon distal movement of the coaxial feedline relative to the outer sheath, and wherein the outer sheath includes a first inner diameter along at least a portion of the longitudinal axis and a distal portion of the outer sheath defines a sliding hub having a second inner diameter greater than the first inner diameter.

2. The flexible microwave catheter according to claim 1, wherein a width of the outer conductor of the radiating portion varies according to a longitudinal position thereof along the inner conductor of the radiating portion.

3. The flexible microwave catheter according to claim 1, further comprising a cap operably coupled to a distal end of the inner conductor and the outer conductor and providing an electrical connection therebetween.

4. The flexible microwave catheter according to claim 1, further comprising a temperature sensor disposed at a distal portion of the radiating portion.

5. The flexible microwave catheter according to claim 1, wherein a radiation pattern generated by the radiating portion is related to at least one of a variable width of the outer conductor or a variable helix angle of the outer conductor in the radiating portion.

6. The flexible microwave catheter according to claim 1, wherein the outer conductor in the radiating portion is helically wrapped about the inner conductor in the radiating portion, and wherein the radiating portion further includes a feed gap defined by a void formed between adjacent wraps of the outer conductor.

7. The flexible microwave catheter according to claim 6, wherein a feed gap ratio, defined by the ratio of a feed gap circumference and an outer conductor circumference along a cross section, changes linearly from a proximal end of the outer conductor in the radiating portion to a distal end of the outer conductor in the radiating portion.

8. The flexible microwave catheter according to claim 7, wherein the feed gap ratio varies between 0% at the proximal end of the radiating portion and about 50% at the distal end of the radiating portion.

9. The flexible microwave catheter according to claim 1, further comprising an actuator coupled to the coaxial feedline, the actuator configured to move the coaxial feedline relative to the catheter hub.

10. The flexible microwave catheter according to claim 9, wherein the actuator is configured to move the coaxial feedline relative to the outer sheath.

11. The flexible microwave catheter according to claim 1, wherein the radiating portion further comprises an outer dielectric insulating layer disposed about the outer conductor in the radiating portion, the outer dielectric insulating layer configured to slide along a length of the sliding hub and deploy from the sliding hub.

12. The flexible microwave catheter according to claim 11, wherein an outer surface of the outer dielectric insulating layer is movable along an inner surface of the sliding hub.

13. The flexible microwave catheter according to claim 11, wherein an outer diameter of the outer dielectric insulating layer is greater than the first inner diameter.

* * * * *